United States Patent
Day et al.

(10) Patent No.: US 9,127,016 B2
(45) Date of Patent: Sep. 8, 2015

(54) SMALL MOLECULE INHIBITORS OF DUSP6 AND USES THEREFOR

(75) Inventors: Billy W. Day, Pittsburgh, PA (US); Waikok Michael Tsang, Pittsburgh, PA (US); Vasiliy N. Korotchenko, Rockville, MD (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 943 days.

(21) Appl. No.: 13/256,584

(22) PCT Filed: Mar. 19, 2010

(86) PCT No.: PCT/US2010/027900
§ 371 (c)(1),
(2), (4) Date: Feb. 1, 2012

(87) PCT Pub. No.: WO2010/108058
PCT Pub. Date: Sep. 23, 2010

(65) Prior Publication Data
US 2012/0122992 A1   May 17, 2012

Related U.S. Application Data

(60) Provisional application No. 61/210,643, filed on Mar. 20, 2009.

(51) Int. Cl.
| C07C 211/00 | (2006.01) |
| A01N 33/02 | (2006.01) |
| C07D 495/04 | (2006.01) |

(52) U.S. Cl.
CPC .................... *C07D 495/04* (2013.01)

(58) Field of Classification Search
CPC ..... C07C 211/42; C12N 5/071; A61K 31/135
USPC .......................................... 564/428; 514/648
See application file for complete search history.

(56) References Cited

U.S. PATENT DOCUMENTS

| 6,476,027 B1 | 11/2002 | Villamil et al. |
| 2007/0173527 A1 | 7/2007 | Bressi et al. |

FOREIGN PATENT DOCUMENTS

| JP | 5758663 A | 4/1982 |
| WO | 9965495 A1 | 12/1999 |
| WO | 0138322 A1 | 5/2001 |

OTHER PUBLICATIONS

Testa, B. et al., Lipophilicity in Molecular Modeling, Pharm Res 13, (1996), pp. 335-343.
Traynelis, V. J. et al., Seven-Membered Heterocycles. I. Synthesis of Benzo[b]thiepin 1,1-Dioxide and 1-Phenylsulfonyl-4-phenyl-1,3-butadiene, J Org Chem 26, (1961), pp. 2728-2733.
Villar-Garea, A. et al., Histone deacetylase inhibitors: understanding a new wave of anticancer agents, Int J Cancer 112, (2004), pp. 171-178.
Vogt A. et al., High-content analysis of cancer-cell specific apoptosis and inhibition of in vivo angiogenesis by synthetic (-)-pironetin and analogs, Chem Biol Drug Des. 2009;74(4):358-68.
Yuen, P. S. T. et al., A simplified method for HPLC determination of creatinine in mouse serum, Am J Physiol Renal Physiol. 2004;286(6):F1116-9.
Zhang, L. et al., Cell cycle progression is required for zebrafish somite morphogenesis but not segmentation clock function, Development 135, (2008), pp. 2065-2070.
Abraira et al., Changes in Sef Levels Influence Auditory Brainstem Development and Function, The Journal of Neuroscience, Apr. 18, 2007, pp. 4273-4282, vol. 27, No. 16.
Almo et al., Structural genomics of protein phosphatases, J Struct Funct Genomics, 2007, pp. 121-140, vol. 8.
Atilgan et al., Anisotropy of Fluctuation Dynamics of Proteins with an Elastic Network Model, Biophysical Journal, Jan. 2001, pp. 505-515, vol. 80.
Bahar et al., Intrinsic Enzyme Dynamics in the Unbound State and Relation to Allosteric Regulation, Curr. Opin. Struct Biol, Dec. 2007, pp. 633-640, vol. 17, No. 6.
Bakan et al., Toward a Molecular Understanding of the Interaction of Dual Specificity Phosphatases with Substrates: Insights from Stucture-Based Modeling and High Throughput Screening, Current Medicinal Chemistry, 2008, pp. 2536-2544, vol. 15.
Brown et al., Transcriptional profiling of endogenous germ layer precursor cells identifies dusp4 as an essential gene in zebrafish endoderm specification, Proc Natl Acad Sci, Aug. 26, 2008, pp. 12337-12342, vol. 105, No. 34.
Camps et al., Catalytic Activation of the Phosphatase MKP-3 by ERK2 Mitogen-Activated Protein Kinase, Science, May 22, 1998, pp. 1262-1265, vol. 280.
Chen et al., Discordance between the Binding Affinity of Mitogen-activated Protein Kinase Subfamily Members for MAP Kinase Phosphatase-2 and Their Ability to Activate the Phosphatase Catalytically, The Journal of Biological Chemistry, Aug. 3, 2001, pp. 29440-29449, vol. 276, No. 31.
Chen et al., Zebrafish tinman homolog demarcates the heart field and initiates myocardial differentiation, Development, 1996, pp. 3809-3816, vol. 122.
Chen et al., Genetics of heart development, TIG, Sep. 2000, pp. 383-388, vol. 16, No. 9.
Cole et al., Profiling the Isomerization of Biologically Relevant (E)-(Z) Isomers by Supercritical Fluid Chromatography (SFC), Modern Medicine, Jun. 1, 2009, pp. 1-6.
Dailey et al., Mechanisms underlying differential responses to FGF signaling, Cytokine & Growth Factor Reviews, 2005, pp. 233-247, vol. 16.
Dowd et al., Isolation of the human genes encoding the Pyst1 and Pyst2 phosphatases: characterisation of Pyst2 as a cytosolic dual-specificity MAP kinase phosphatase and its catalytic activation by both MAP and SAP kinases, Journal of Cell Science, 1998, pp. 3389-3399, vol. 111.

(Continued)

*Primary Examiner* — Jafar Parsa
(74) *Attorney, Agent, or Firm* — The Webb Law Firm

(57) ABSTRACT

Compounds that stimulate fibroblast growth factor production, and thus cell growth are provided. Also provided are compositions comprising the compounds and methods of using the compounds. The compounds can be used to treat wounds, to expand cell populations, such as hematopoietic cells, or to grow tissue in vitro, among other uses.

22 Claims, 19 Drawing Sheets

(56) References Cited

OTHER PUBLICATIONS

Ducruet et al., Dual Specificity Protein Phosphatases: Therapeutic Targets for Cancer and Alzheimer's Disease, Annu. Rev. Med., 2005, pp. 725-750, vol. 45.
Ekker et al., Coordinate embryonic expression of three zebrafish engrailed genes, Development, 1992, pp. 1001-1010, vol. 116.
Eyal et al., Anisotropic network model: systematic evaluation and a new web interface, Bioinformatics, 2006, pp. 2619-2627, vol. 22, No. 21.
Fürthauer et al., sprouty4 acts in vivo as a feedback-induced antagonist of FGF signaling in zebrafish, Development, 2001, pp. 2175-2186, vol. 128.
Gurtner et al., Wound repair and regeneration, Nature, May 15, 2008, pp. 314-321, vol. 453.
Hassner et al., The Chemistry of Derivatives of 2-Benzaltralone. II. Absorption Spectra and Stereostructure, J Am Soc Chem, Feb. 20, 1958, pp. 893-900, vol. 80.
Huey et al., A Semiempirical Free Energy Force Field with Charge-Based Desolvation, J Comput Chem, 2007, pp. 1145-1152, vol. 28.
Isin et al., Mechanism of Signal Propagation upon Retinal Isomerization: Insights from Molecular Dynamics Simulations of Rhodopsin Restrained by Normal Modes, Biophysical Journal, Jul. 2008, pp. 789-803, vol. 95.
Jeong et al., Crystal Structure of the Catalytic Domain of Human DUSP5, a Dual Specificity MAP Kinase Protein Phosphatase, Proteins, 2007, pp. 253-258, vol. 66.
Jeong et al., Crystal Structure of the Catalytic Domain of Human MAP Kinase Phosphatase 5: Structural Insight into Constitutively Active Phosphatase, J. Mol. Biol., 2006, pp. 946-955, vol. 360.
Jones et al., Development and Validation of a Genetic Algorithm for Flexible Docking, J. Mol. Biol., 1997, pp. 727-748, vol. 267.
Jones et al., Molecular Recognition of Receptor Sites using a Genetic Alogorithm with a Description of Desolvation, J. Mol. Biol., 1995, pp. 43-53, vol. 245.
Keegan et al., Organization of cardiac chamber progenitors in the zebrafish blastula, Development, 2004, pp. 3081-3091, vol. 131.
Kudoh et al., A Gene Expression Screen in Zebrafish Embryogenesis, Genome Research, 2001 pp. 1979-1987, vol. 11.
Latinkić et al., The Xenopus Brachyury promoter is activated by FGF and low concentrations of activin and suppressed by high concentrations of activin and by paired-type homeodomain proteins, Genes & Development, 1997, pp. 3265-3276, vol. 11.
Lazo et al., Structurally Unique Inhibitors of Human Mitogen-Activated Protein Kinase Phosphatase-1 Identified in a Pyrrole Carboxamide Library, The Journal of Pharmacology and Experimental Therapeutics, 2007, pp. 940-947, vol. 322, No. 3.
Lazo et al., Discovery and Biological Evaluation of a New Family of Potent Inhibitors of the Dual Specificity Protein Phosphatase Cdc25, J. Med. Chem., 2001, pp. 4042-4049, vol. 44.
Lazo et al., Novel benzofuran inhibitors of human mitogen-activated protein kinase phosphatase-1, Bioorganic & Medicinal Chemistry, 2006, pp. 5643-5650, vol. 14.
Lepilina et al., A Dynamic Epicardial Injury Response Supports Progenitor Cell Activity during Zebrafish Heart Regeneration, Cell, Nov. 3, 2006, pp. 607-619, vol. 127.
Li et al., Dusp6(Mkp3) is a negative feedback regulator of FGF stimulated ERK signaling during mouse development, Development, Jan. 2007, pp. 167-176, vol. 134, No. 1.
Liao et al., SCL/Tal-1 transcription factor acts downstream of cloche to specify hematopoietic and vascular progenitors in zebrafish, Genes & Development, 1998, pp. 621-626, vol. 12.
Lovell et al., The Penultimate Rotamer Library, Proteins, 2000, pp. 389-408, vol. 40.
Mackerell et al., All-Atom Empirical Potential for Molecular Modeling and Dynamics Studies of Proteins, J. Phys. Chem. B, 1998, pp. 3586-3616, vol. 102.
Maillet et al., DUSP6 (MKP3) Null Mice Show Enhanced ERK1/2 Phosphorylation at Baseline and Increased Myocyte Proliferation in the Heart Affecting Disease Susceptibility, The Journal of Biological Chemistry, Nov. 7, 2008, pp. 31246-31255, vol. 283, No. 45.
Mandl et al., Specific Inactivation and Nuclear Anchoring of Extracellular Signal-Regulated Kinase 2 by the Inducible Dual-Specificity Protein Phosphatase DUSP5, Molecular and Cellular Biology, Mar. 2005, pp. 1830-1845, vol. 25, No. 5.
Mark et al., Over-expression and refolding of MAP kinase phosphatase 3, Protein Expression & Purification, 2007, pp. 253-260, vol. 54.
Marques et al., Reiterative roles for FGF signaling in the establishment of size and proportion of the zebrafish heart, Dev. Biol, Sep. 15, 2008, pp. 397-406, vol. 321 No. 2.
Martínez et al., Studies on the chemistry of 2-(2-oxo-3-phenylpropyl)-benzaldehydes: novel total synthesis of 3-phenylnaphthalen-2-ols and 2-hydroxy-3-phenyl-1,4-naphthoquinones, Tetrahedron, 2005, pp. 485-492, vol. 61.
Maury et al., Mobile Keto Allyl Systems. VI. Reaction of 3-Bromo-2-benzal-1-indanone with Amines, The Journal of Organic Chemistry, May 1968, pp. 1900-1907, vol. 33, No. 5.
Maves et al., FGF3 and FGF8 mediate a rhombomere 4 signaling activity in the zebrafish hindbrain, Development, 2002, pp. 3825-3837, vol. 129.
Molina et al., Generation of FGF reporter transgenic zebrafish and their utility in chemical screens, BMC Developmental Biology, 2007, pp. 1-14, vol. 7, No. 62.
Morris et al., Automated Docking Using a Lamarckian Genetic Algorithm and an Empirical Binding Free Energy Function, Journal of Computational Chemistry, 1998, pp. 1639-1662, vol. 19, No. 14.
Murray et al., Mobile Keto Allyl Systems. 18. Synthesis and Charge-Transfer Interactions of 2-(alpha Aminobenzyl)-1-indenones, J. Org. Chem., 1976, pp. 3540-3545, vol. 41, No. 22.
North et al., Prostaglandin E2 regulates vertebrate haematopoietic stem cell homeostasis, Nature, Jun. 21, 2007, pp. 1007-1011, vol. 447.
Owens et al., Differential regulation of MAP kinase signalling by dual-specificity protein phosphatases, Oncogene, 2007, pp. 3203-3213, vol. 26.
Oxtoby et al., Cloning of the zebrafish krox-20 gene (krx-20) and its expression during hindbrain development, Nucleic Acids Research, 1993, pp. 1087-1095, vol. 21, No. 5.
Pearson et al., Elimination Reactions of alpha-Halogenated Ketones. IX. A Comparison of the Reactions of 2-Bromo-2-(alpha-bromobenzyl)-1-indanone with Those of 2-Bromo-2-( alpha-bromobenzyl)-3,3-dimethyl-1-indanone, J. Org. Chem., Sep. 1962, pp. 3038-3044, vol. 27.
Peterson et al., Small molecule developmental screens reveal the logic and timing of vertebrate development, Proc Natl Acad Sci USA, Nov. 21, 2000, pp. 12965-12969, vol. 97, No. 24.
Pham et al., Combinatorial function of ETS transcription factors in the developing vasculature, Dev Biol., Mar. 15, 2007, pp. 772-783, vol. 303, No. 2.
Phillips et al., Scalable Molecular Dynamics with NAMD, J Comput Chem., Dec. 2005, pp. 1781-1802, vol. 26, No. 16.
Qian et al., Microarray Analysis of Zebrafish cloche Mutant Using Amplified cDNA and Identification of Potential Downstream Target Genes, Developmental Dynamics, 2005, pp. 1163-1172, vol. 233.
Reifers et al., Fgf8 is mutated in zebrafish acerebellar (ace) mutants and is required for maintenance of midbrain-hindbrain boundary development and somitogenesis, Development, 1998, pp. 2381-2395, vol. 125.
Reifers et al., Induction and differentiation of the zebrafish heart requires fibroblast growth factor 8 (fgf8/acerebellar), Development, 2000, pp. 225-235, vol. 127.
Schoenebeck et al., Vessel and Blood Specification Override Cardiac Potential in Anterior Mesoderm, Developmental Cell, Aug. 2007, pp. 254-267, vol. 13.
Slack et al., Distinct Binding Determinants for ERK2/p38alpha and JNK MAP Kinases Mediate Catalytic Activation and Substrate Selectivity of MAP Kinase Phosphatase-1, The Journal of Biological Chemistry, May 11, 2001, pp. 16491-16500, vol. 276, No. 19.
Stewart et al., Crystal structure of the MAPK phosphatase Pyst1 catalytic domain and implications for regulated activation, Nature Structural Biology, Feb. 1999, pp. 174-181, vol. 6, No. 2.

(56) References Cited

OTHER PUBLICATIONS

Sumanas et al., Identification of novel vascular endothelial-specific genes by the micorarray analysis of the zebrafish cloche mutants, Blood, Jul. 15, 2005, pp. 534-541, vol. 106, No. 2.
Thisse et al., Functions and regulations of fibroblast growth factor signaling during embryonic development, Developmental Biology, 2005, pp. 390-402, vol. 287.
Thisse et al., Fast Release Clones: A High Throughput Expression Analysis, ZFIN Direct Data Submission, 2004, 2 pages.
Treibs et al., Pseudoaromatic compounds from 2-indanones. Justus Liebigs Ann Chem 639, 1961, pp. 204-213.
Tsang et al., Promotion and Attenuation of FGF Signaling Through the Ras-MAPK Pathway, Science's Stke, 2004, pp. 1-5.
Tsang et al., A role for MKP3 in axial patterning of the zebrafish embryo, Development, Mar. 4, 2004, pp. 2769-2779, vol. 131.
Tsang et al., Identification of Sef, a novel modulator of FGF signalling, Nature Cell Biology, Feb. 2002, pp. 165-169, vol. 4.
Urness et al., Expression of ERK signaling inhibitors Dusp6, Dusp7 and Dusp9 during mouse ear development, Dev Dyn., Jan. 2008, pp. 163-169, vol. 237, No. 1.
Vogt et al., Automated image-based phenotypic analysis in zebrafish embryos, Dev Dyn., Mar. 2009, pp. 656-663, vol. 238, No. 3.
Vogt et al., The Benzo[c]phenanthridine Alkaloid, Sanguinarine, Is a Selective, Cell-active Inhibitor of Mitogen-activated Protein Kinase Phosphatase-1, The Journal of Biological Chemistry, May 13, 2005, pp. 19078-19086, vol. 280, No. 19.
Vogt et al., Implementation of high-content assay for inhibitors of mitogen-activated protein kinase phosphatases, Methods, Jul. 2007, pp. 268-277, vol. 42, No. 3.
Vogt et al., Chemical complementation: a definitive phenotypic strategy for identifying small molecule inhibitors of elusive cellular targets, Pharmacology & Therapeutics, 2005, pp. 212-221, vol. 107.
Yelon et al., Restricted Expression of Cardiac Myosin Genes Reveals Regulated Aspects of Heart Tube Assembly in Zebrafish, Developmental Biology 1999, pp. 23-37, vol. 214.
Yelon et al., The bHLH transcription factor Hand2 plays parallel roles in zebrafish heart and pectoral fin development, Development, 2000, pp. 2573-2582, vol. 127.
Yelon, Cardiac Patterning and Morphogenesis in Zebrafish, Developmental Dynamics, 2001, pp. 552-563, vol. 222.
Yu et al., Dorsomorphin inhibits BMP signals required for embryogenesis and iron metabolism, Nat Chem Biol., Jan. 2008, pp. 33-41, vol. 4, No. 1.
Zhou et al., Mapping ERK2-MKP3 Binding Interfaces by Hydrogen/Deuterium Exchange Mass Spectrometry, The Journal of Biological Chemistry, Dec. 15, 2006, pp. 38834-38844, vol. 281, No. 50.
Zon et al., In Vivo Drug Discovery in the Zebrafish, Nature Reviews, Jan. 2005, pp. 35-44, vol. 4.
Andersen, C. L. et al., Normalization of real-time quantitative reverse transcription-PCR data: a model-based variance estimation approach to identify genes suited for normalization, applied to bladder and colon cancer data sets, Cancer Res 64, (2004), pp. 5245-5250.
Anderson, R. J. et al., Retinoic acid regulation of renal tubular epithelial and vascular smooth muscle cell function, J Am Soc Nephrol 9, (1998), pp. 773-781.
Argiles, A. et al., Retinoic acid affects the cell cycle and increases total protein content in epithelial cells, Kidney Int 36, (1989), pp. 954-959.
Bacallo, R. et al., Molecular events in the organization of renal tubular epithelium: from nephrogenesis to regeneration, Am J Physiol 257, (1989), pp. F913-F924.
Balasubramanian, S. et al. Isoform-specific histone deacetylase inhibitors: The next step?, Cancer Lett 280, (2009), pp. 211-221.
Bi, B. et al., Stromal cells protect against acute tubular injury via an endocrine effect, J Am Soc Nephrol. 2007; 18 (9):2486-96.
Bieliauskas, A. V. et al., Isoform-selective histone deacetylase inhibitors, Chem Soc Rev 37, (2008), pp. 1402-1413.
Blumberg, B. et al., An essential role for retinoid signaling in anteroposterior neural patterning, Development 124, (1997), pp. 373-379.
Bolden, J. E. et al., Anticancer activities of histone deacetylase inhibitors, Nat Rev Drug Discov 5, (2006), pp. 769-784.
Boner G. et al., Combination Antihypertensive Therapy in the Treatment of Diabetic Nephropathy, Diabetes Technol Ther 2002;4(3):313-21.
Bradner, J. E. et al., Chemical phylogenetics of histone deacetylases, Nat Chem Biol 6, (2010), pp. 238-243.
Brewster, M.E. et al., Cyclodextrins as pharmaceutical solubilizers, Advanced Drug Delivery Reviews 59:645-666 (2007).
Buchwald, M. et al., HDACi—Targets beyond chromatin, Cancer Lett 280, (2009), pp. 160-167.
Butler, K. V. et al., Chemical Origins of Isoform Selectivity in Histone Deacetylase Inhibitors, Curr Pharm Des 14, (2008), pp. 505-528.
Cartry, J. et al., Retinoic acid signalling is required for specification of pronephric cell fate, Dev Biol 299, (2006), pp. 35-51.
Cianciolo Cosenitino, C. et al., (2010) Intravenous Microinjections of Zebrafish Larvae to Study Acute Kidney Injury, JoVE Aug. 4 (42).
De Groh, E. D. et al., Inhibition of Histone Deacetylase Expands the Renal Pprogenitor Cell Population, J Am Soc Nephrol 21, (2010), pp. 794-802.
Doi K. et al., Animal models of sepsis and sepsis-induced kidney injury, J Clin Invest. 2009; 119(10):2868-78.
Drummond, I. A., Kidney Development and Disease in the Zebrafish, J Am Soc Nephrol 16, (2005), pp. 299-304.
Haggarty, S. J. et al., Domain-selective small-molecule inhibitor of histone deacetylase 6 (HDAC6)-mediated tubulin deacetylation, Proc Natl Acad Sci USA 100, (2003), pp. 4389-4394.
Harris, W. A. et al., Neuronal Determination without Cell Division in Xenopus Embryos, Neuron 6, (1991), pp. 499-515.
Hubbert, C. et al., HDAC6 is a microtubule-associated deacetylase, Nature 417, (2002), pp. 455-458.
Imai, N. et al., Inhibition of Histone Deacetylase Activates Side Population Cells in Kidney and Partially Reverses Chronic Renal Injury, Stem Cells 25, (2007), pp. 2469-2475.
Jacobsen, F. E., et al., The Design of Inhibitors for Medicinally Relevant Metalloproteins, ChemMedChem 2, (2007), pp. 152-171.
Keegan, B. R. et al. Retinoic Acid Signaling Restricts the Cardiac Progenitor Pool, Science 307, (2005), pp. 247-249.
Kennedy, S. E. et al., Murine renal ischaemia-reperfusion injury, Nephrology (Carlton). 2008; 13(5):390-6.
Khan, N. et al Determination of the class and isoform selectivity of small-molecule histone deacetylase inhibitors, Biochem J 409, (2008), pp. 581-589.
Kimmel, C. B. et al., Stages of Embryonic Development of the Zebrafish, Dev Dyn 203(3), (1995), pp. 253-310.
Korotchenko, V. N. et al., In Vivo Structure-Activity Relationship Studies Support Allosteric Targeting of a Dual Specificity Phosphatase, ChemBioChem 15: 1436-1445 and supplemental data (2014).
Lipinski, C. A. et al., Experimental and computational approaches to estimate solubility and permeability in drug discovery and development settings, Adv Drug Deliv Rev 46, (2001), pp. 3-26.
Loftsson, T. et al., Self-Association of Cyclodextrins and Cyclodextrin Complexes, J. Pharm. Sci. 93(5):1091-1099 (2004).
Loftsson, T. et al., Cyclodextrins in Drug Delivery, Expert. Opin. Drug Deliv. 2:335-351 (2005).
Martin, Y. C. et al., Examination of the Utility of the Topliss Schemes for Analog Synthesis, J Med Chem. 1973;16 (5):578-9.
Marumo, T. et al., Epigenetic Regulation of BMP7 in the Regenerative Response to Ischemia, J Am Soc Nephrol 19, (2008), pp. 1311-1320.
Menegola, E. et al., Inhibition of Histone Deacetylase as a New Mechanism of Teratogenesis, Birth Defects Res C Embryo Today 78, (2006), pp. 345-353.
Mitamura, T. et al., Diphtheria Toxin Binds to the Epidermal Growth Factor (EGF)-like Domain of Human Heparin-binding EGF-like Growth Factor/Diphtheria Toxin Receptor and Inhibits Specifically Its Mitogenic Activity, J Biol Chem 270, (1995), pp. 1015-1019.
Molina, G. et al., Zebrafish chemical screening reveals an inhibitor of Dusp6 that expands cardiac cell lineages, Nat Chem Biol 5, (2009), pp. 680-687.

(56) References Cited

OTHER PUBLICATIONS

Mundel, P. et al., Rearrangements of the Cytoskeleton and Cell Contacts Induce Process Formation During Differentiation of Conditionally Immortalized Mouse Podocyte Cell Lines, Exp Cell Res 236, (1997), pp. 248-258.

Noel, E. S. et al., Organ-specific requirements for Hdac1 in liver and pancreas formation, Dev Biol 322, (2008), pp. 237-250.

Picker, A. et al., A novel positive transcriptional feedback loop in midbrain-hindbrain boundary development is revealed through analysis of the zebrafish pax2.1 promoter in transgenic lines, Development 2002 129 (13): pp. 3227-3239.

Pohl, L. R. et al., Electrophilic halogens as potentially toxic metabolites of halogenated compounds, Trends Pharm Sci 5, (1984), pp. 61-64.

Popa-Burke, I. G. et al., Streamlined System for Purifying and Quantifying a Diverse Library of Compounds and the Effect of Compound Concentration Measurements on the Accurate Interpretation of Biological Assay Results, Anal Chem 76, (2004), pp. 7278-7287.

Rasheed, A. et al., Cyclodextrins as Drug Carrier Molecule: A Review, Sci. Pharm. 76:567-598 (2008).

Remington: The Science and Practice of Pharmacy, 21st edition, ed. Paul Beringer et al., Lippincott, Williams & Wilkins, Baltimore, MD, Easton, PA (2005) Chapters 37, 39, 41, 42, and 45.

Ruijter, J. M. et al., Amplification efficiency: linking baseline and bias in the analysis of quantitative PCR data, Nucleic Acids Res 37, e45, (2009), 12 pages.

Sanderson, L. et al., Plasma pharmacokinetics and metabolism of the histone deacetylase inhibitor trichostatin after intraperitoneal administration to mice, Drug Metab Dispos 32, (2004), pp. 1132-1138.

Schwartz, E. J. et al., Human Immunodeficiency Virus-1 Induces Loss of Contact Inhibition in Podocytes, J Am Soc Nephrol 12, (2001), pp. 1677-1684.

Soroldoni, D. et al., Simple and Efficient Transgenesis with Meganuclease Constructs in Zebrafish, Methods Mol Bio 2009; 546: 117-30.

Swanhart, L. M. et al., Characterization of an lhx1a transgenic reporter in zebrafish, Int J Dev Biol 54(4): 731-6 (2010).

Tang, R. et al., Validation of Zebrafish (Danio rerio) Reference Genes for Quantitative Real-time RT-PCR Normalization, Acta Biochim Biophys Sin (Shanghai) 39, (2007), pp. 384-390.

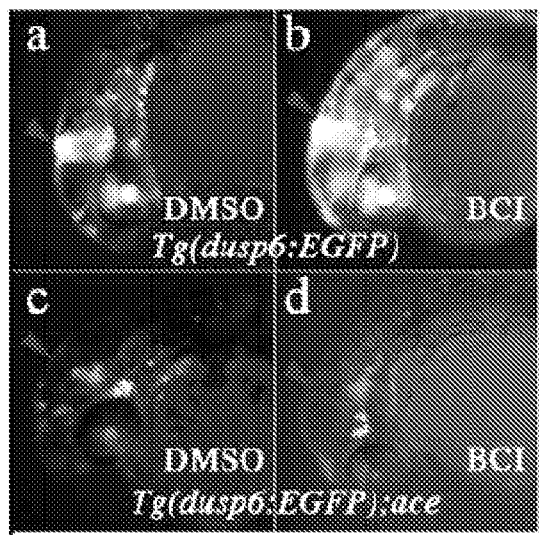
Figs. 8a-d
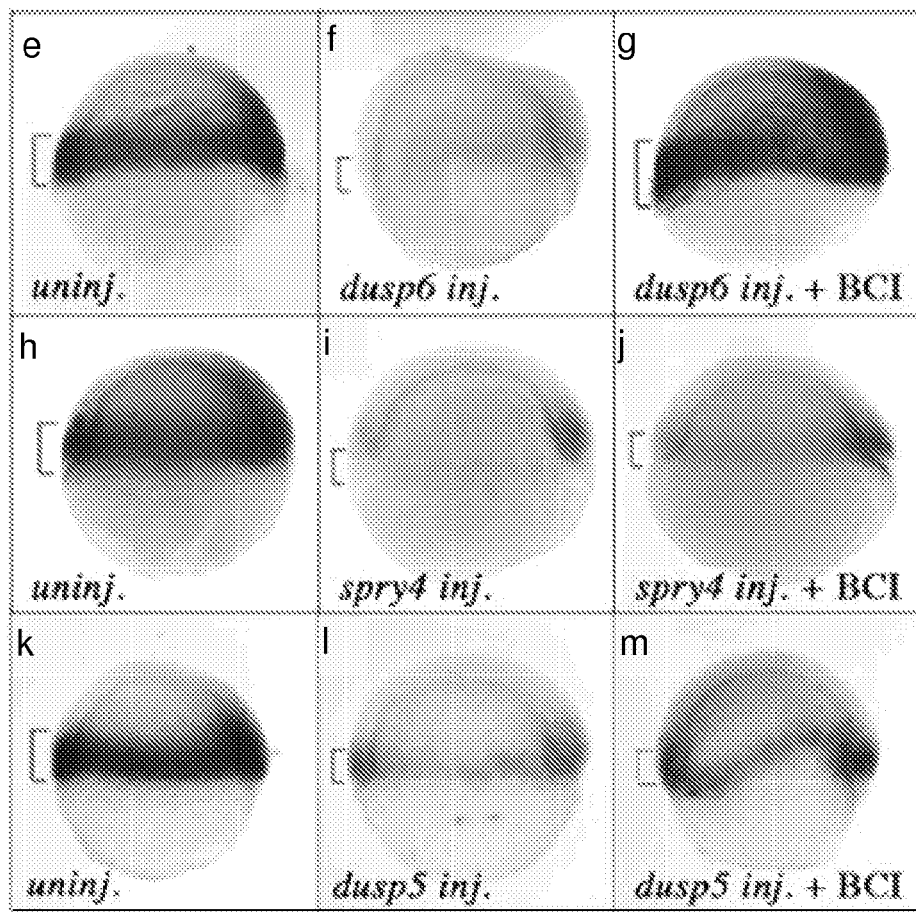
Figs. 8e-m

Figs. 10a-d

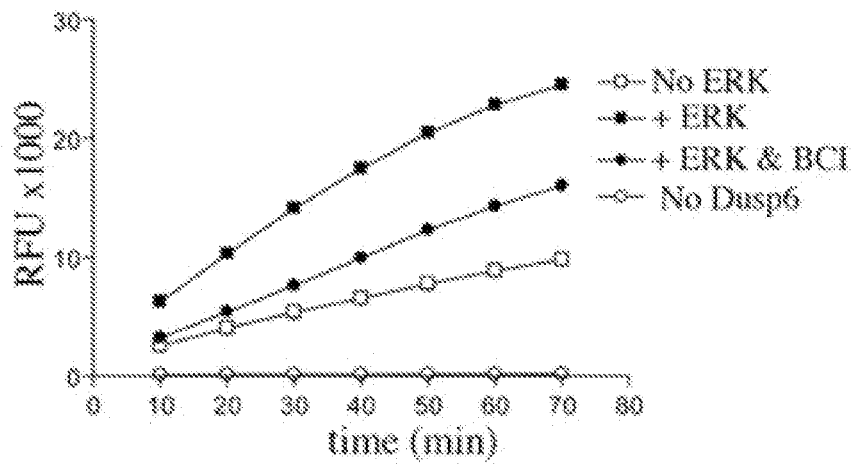
Fig. 13
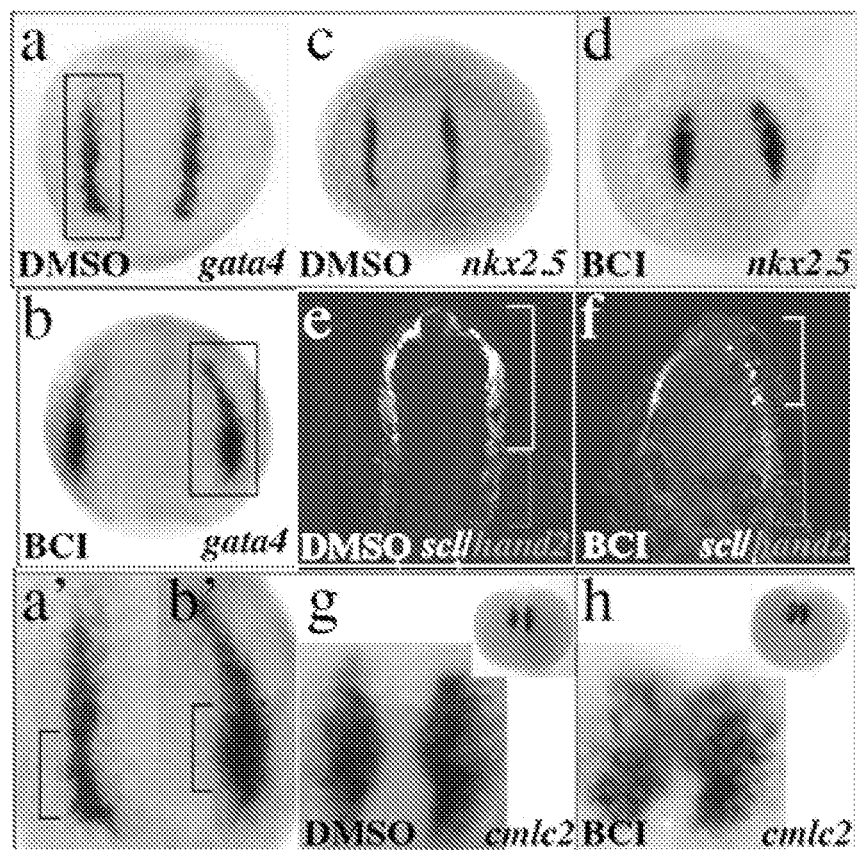
Figs. 14a-h

SMALL MOLECULE INHIBITORS OF DUSP6 AND USES THEREFOR

CROSS REFERENCE TO RELATED APPLICATIONS

This application is a National Stage of International Patent Application No. PCT/US2010/027900, filed Mar. 19, 2010, which claims the benefit of U.S. Provisional Patent Application No. 61/210,643, filed Mar. 20, 2009, which is herein incorporated by reference in its entirety.

This invention was made with government support under Grant Nos. HD053287, HL088016, CA052995, MH074411, CA078039 awarded by the National Institutes of health. The government has certain rights in the invention.

The Sequence Listing associated with this application is filed in electronic format via EFS-Web and is hereby incorporated by reference into the specification in its entirety. The name of the text file containing the Sequence Listing is 113331_ST25.txt. The size of the text file is 2,617 bytes, and the text file was created on May 7, 2015.

Fibroblast Growth Factors (FGFs) are members of a large family of secreted glycoproteins that serve important functions in development, proliferation and cellular homeostasis. These ligands bind to single-pass transmembrane proteins of the receptor tyrosine kinase class to activate multiple signaling pathways including the rat sarcoma homologue (RAS)/mitogen-activated protein kinase (MAPK) cascade. The wide-ranging biological roles of FGFs and the multitude of signaling pathways activated by this family of ligands suggest that FGF signaling must be tightly regulated. Dual specificity phosphatase 6 (Dusp6) (also named MAP Kinase Phosphatase 3), Sproutys (Spry1-4) and Sef (similar expression to FGFs) proteins function as RAS/MAPK pathway feedback attenuators. Through their concerted activities FGF signaling is adjusted to optimal levels in embryogenesis (Thisse, B. et al. *Dev Biol* 287, 390-402 (2005) and Tsang, M. et al. *Sci STKE* 2004, pe17 (2004)). Sef and Spry proteins suppress RAS/MAPK signaling at multiple points within the pathway, while Dusp6 inhibits the pathway only by dephosphorylation of one class of the MAPK family, extracellular signal-regulated kinase (ERK). Sef, Dusp6 and Sprouty depletion in zebrafish or gene knock-out in mice have revealed the requirement for these proteins to limit FGF signaling during development and homeostasis (Thisse, B. et al. *Dev Biol* 287, 390-402 (2005); Abraira, V. E. et al. *J Neurosci* 27, 4273-82 (2007); Li, C., et al. *Development* 134, 167-76 (2007); and Maillet, M. et al. *J Biol Chem* 283, 31246-55 (2008)). The identification of small molecules that can reversibly modulate FGF signaling would provide useful tools to dissect the roles for this pathway in development that are not feasible with current genetic methods.

SUMMARY

The dual specificity phosphatase 6 (Dusp6) functions as a feedback regulator of fibroblast growth factor (FGF) signaling to limit the activity of extracellular signal regulated kinase (ERK) 1 and 2. A small molecule inhibitor of Dusp6, (E)-2-benzylidene-3-(cyclohexylamino)-2,3-dihydro-1H-inden-1-one (BCI), was identified using a transgenic zebrafish chemical screen. BCI treatment blocked Dusp6 activity and enhanced FGF target gene expression in zebrafish embryos. Docking simulations revealed an allosteric binding site for BCI within the phosphatase domain. Studies in vitro supported the model that BCI inhibits Dusp6 catalytic activation by ERK2. A temporal role for Dusp6 in restricting cardiac progenitors and controlling heart organ size was uncovered with BCI treatment at varying developmental stages. Using this in vivo zebrafish chemical screen, several novel compounds were found to target Dusp6, a component of the FGF signaling pathway that has eluded traditional high throughput in vitro screens.

BRIEF DESCRIPTION OF THE DRAWINGS

FIG. 13. Testing in vitro of the allosteric inhibition mechanism. ERK2 stimulated Dusp6 dephosphorylation of OMFP; and this induction was blocked by BCI. RFU, Relative Fluorescent Units were measured at excitation/emission wavelengths of 485/525 nm.

14. Dusp6 and FGFs regulate heart size. (a-h & k-m) Hybridization in situ of treated embryos as indicated. (a, b, a', b') BCI treatment expanded gata4 expression in the caudal ALPM; blue box and brackets mark ALPM and caudal cardiac domain, respectively. (c & d) BCI increased nkx2.5 expression and expanded cardiac progenitor populations. (e & f) Fluorescent double in situ hybridization showing sc/ (green) and hand2 (red) expression in BCI-treated embryos. Reduction of sc/expression with a concomitant expansion of hand2 in BCI-treated embryos (F). Red and green bracket show expression domains. (g & h) cmlc2 expression in 18-somite stage embryos showed an increase in cardiomyocytes in BCItreated embryos. (i & j) Larvae at 56 hpf treated with BCI (from 40% epiboly for 8 hours) exhibited an enlarged heart. Red outline shows heart. These phenotypes correspond to expansion of vmhc (compare l to k and cmlc2 (compare n to m) staining (red arrowheads). (o) Graph showing temporal inhibition of Dusp6 from gastrula to somitogenesis stages resulted in cardiac expansion.

Figure 15:
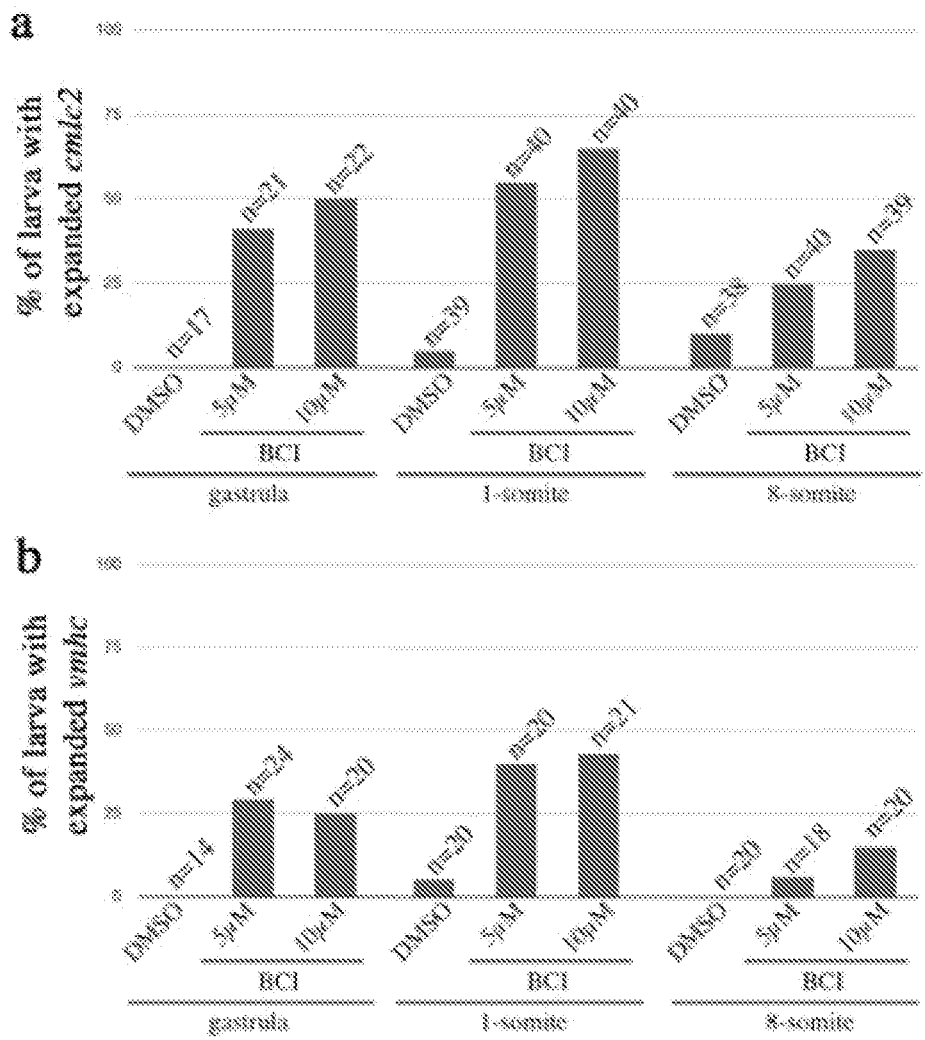

FIG. 15. BCI treatment from gastrula stage onwards resulted in enlarged hearts (a & b) Graph showing BCI treatment resulted in cardiac expansion as measured by cmlc2 and vmhc expression. Note that by the 8-somite stage, the ability of BCI to induce heart expansion was reduced.

Figure 16:
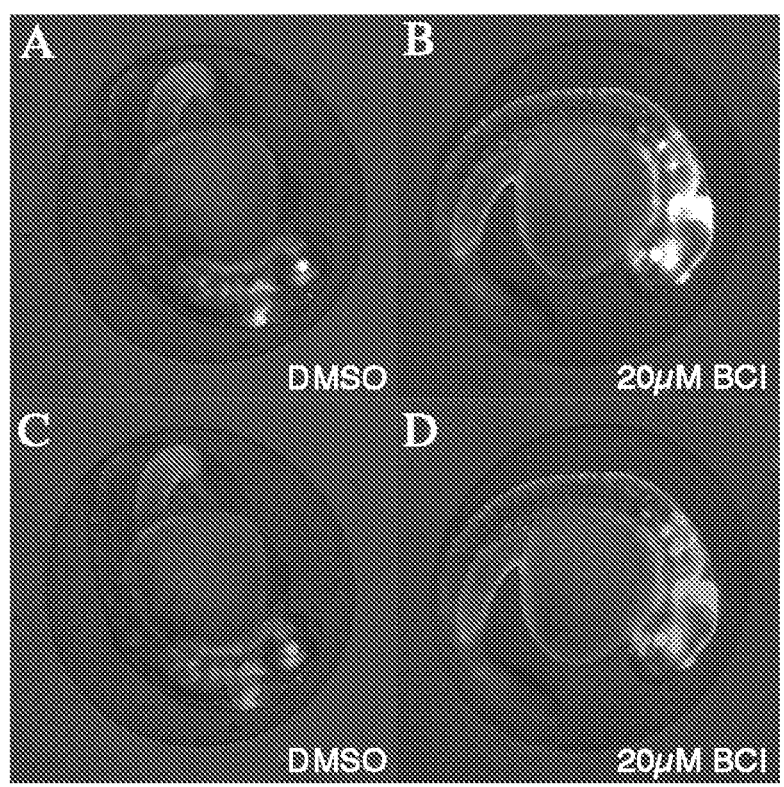

FIG. 16 shows BCI expanded GFP expression in transgenic embryos. The $EC_{50}$ was measured as 11.4 µM.

Figure 17:
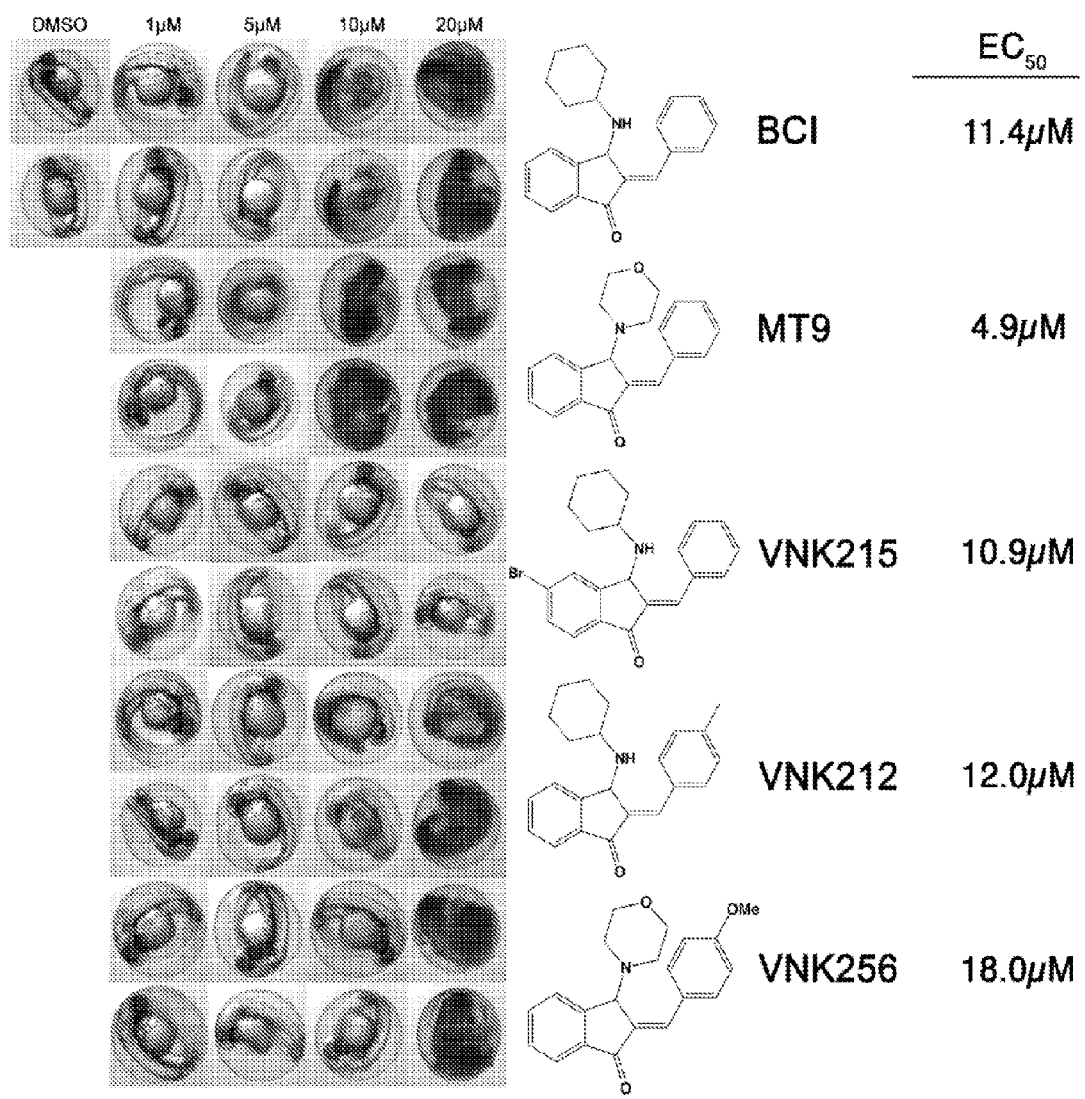

FIG. 17 shows toxicity and $EC_{50}$ for selected BCI analogs in zebrafish.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise" or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the terms "patient" or "subject" refer to members of the animal kingdom including but not limited to human beings.

The dual specificity phosphatase Dusp6 is a mitogen-activated protein kinase (MAPK) phosphatase, also known as MKP3, that functions as a feedback regulator of fibroblast growth factor (FGF) signaling to limit the activities of the extracellular regulated kinase ERK2. A small molecule inhibitor of Dusp6, (E)-2-benzylidene-3-(cyclohexylamino)-2,3-dihydro-1H-inden-1-one (BCI), was identified from a zebrafish chemical screen. Treatment with BCI blocked Dusp6 activity and expanded FOF target gene expression in the embryo as visualized with green fluorescent protein-labeled gene products. Herein, we report the design, synthesis, biological activity and structure-activity relationships (SAR) of BCI analogs. Syntheses of affinity versions of BCI will be disclosed.

The zebrafish embryo is a vertebrate animal model well-suited for high-content small molecule screening (Zon, L. I. et al. Nat Rev Drug Discov 4, 35-44 (2005) and Vogt, A. et al. Dev Dyn 238, 656-663 (2009)). Due to its small size, rapid development and ease of handling it is possible to identify compounds that affect developmental processes and chemical modulators of signaling pathways in vivo (Zon, L. I. et al. Nat Rev Drug Discov 4, 35-44 (2005) and Peterson, R. T., et al. Proc Natl Acad Sci USA 97, 12965-9 (2000)). Previous zebrafish chemical screens have relied on the observations of phenotypes generated by small molecules treatment. In one phenotypic screen, Dorsomorphin was identified as an inhibitor of Bone Morphogenetic Protein (BMP) as embryos exhibited patterning defects upon chemical treatment and subsequent studies utilizing Dorsomorphin in mice have revealed the importance of the BMP pathway in regulating iron metabolism (Yu, P. B. et al. Nat Chem Biol 4, 33-41 (2008)). Another example of the relevance of zebrafish screens was the discovery that Prostaglandin E2 is a key regulator of haematopoietic stem cells (HSC) homeostasis. These studies have shown that this pathway is conserved in vertebrates and provide the potential for using molecules to expand HSC to restore blood deficiencies in patients (North, T. E. et al. *Nature* 447, 1007-11 (2007)).

The generation of transgenic reporter lines in zebrafish offers alternative in vivo tools for chemical screening. Reporters for FGF signaling have been generated and allow for the live visualization of signaling activity during early development. Here, a chemical screen was performed with an FGF reporter transgenic line and identified a small molecule, (E)-2-benzylidene-3-(cyclohexylamino)-2,3-dihydro-1H-inden-1-one (BCI), that hyperactivated FGF signaling. Further analyses revealed that BCI blocked Dusp6 activity in zebrafish embryos and in cultured cells. Molecular modeling predicted an energetically favorable site for BCI binding on Dusp6 phosphatase domain and suggested a plausible allosteric mechanism of action, which was supported by in vitro assays. In one non-limiting example, described below, using BCI as a chemical probe, it was revealed that inhibition of Dusp6 activity during somitogenesis expanded cardiac progenitors at the expense of endothelial lineages. This example suggests that Dusp6 functions, at least in one instance, as an attenuator of FGF signaling in the cardiac field to regulate heart organ size. Further studies, also described below, indicate that a number of analogs of BCI have equal or better activity.

Thus, provided herein are compounds having the general formula:

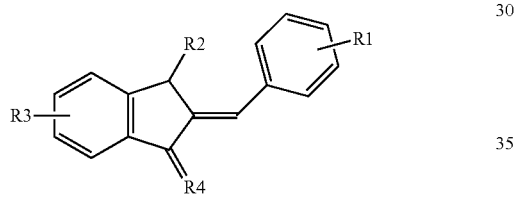

where R1 and R3 represent one or more independently of H, halo, $C_{1-3}$ alkyl, $C_{1-3}$ alkoxyl or —CN; R2 is a primary or secondary amine (—NRH or —NRR', forming, when incorporated into the compound, a secondary or tertiary amine); and R4 is =O or —OH. In one embodiment, when R1 and R3 are H (that is, the aryl rings containing R1 and R3 contain only hydrogens) and R4 is =O, R2 is not cyclohexylamine, cyclophenylamine, piperidine or morpholine. In one example, the compound has the formula:

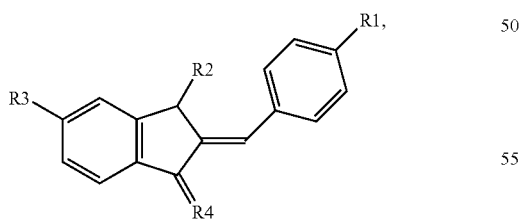

with R1, R2, R3 and R4 defined as indicated above.

Examples of such compounds are depicted in Table 1, below. In one example, R3 is halo, that is, the ring to which R3 is attached may comprise one or more, independently, halo groups, e.g., F, Cl, Br and I. In one example, R3 is Br (a single Br). In another example, R2 is a $C_{4-10}$ cycloalkylamine, including cyclobutylamine, cyclopentylamine, cyclohexylamine, cycloheptylamine, cyclooctylamine, cyclononylamine, and cyclodecylamine, for example, R2 may be cyclopentylamine or cycloheptylamine, or R1 is H, R2 is one of cyclopentylamine, cyclohexylamine, and cycloheptylamine, and R3 is Br. In one non-limiting embodiment, R1 is halo or dihalo, for example, 4-chloro or 3,4-dichloro.

TABLE 1

BCI analogs

TABLE 1-continued
BCI analogs
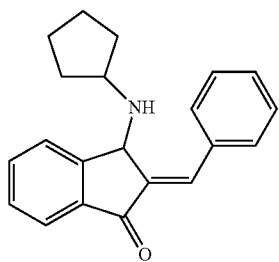
VNK-I-164
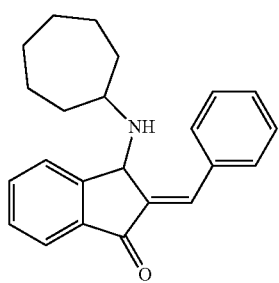
VNK-I-165
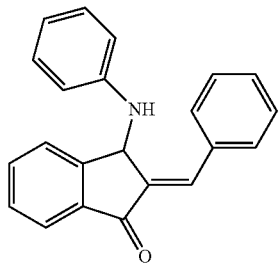
VNK-I-149
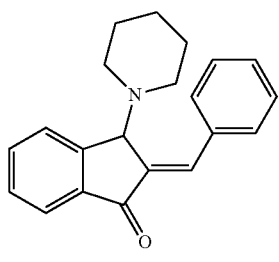
VNK-I-147
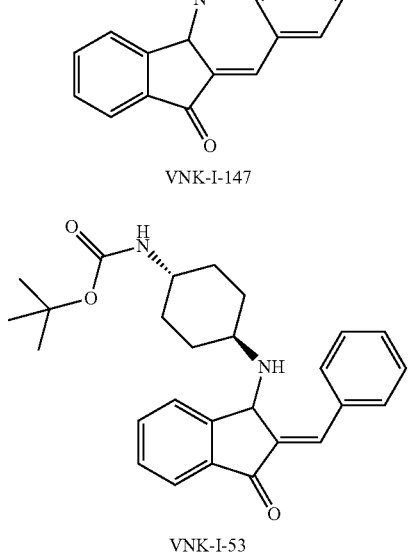
VNK-I-53
TABLE 1-continued
BCI analogs
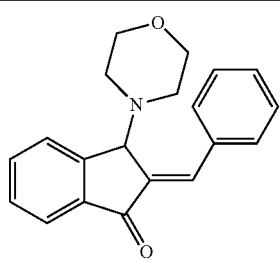
VNK-I-148
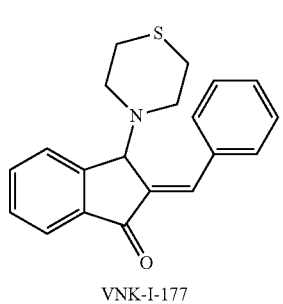
VNK-I-177
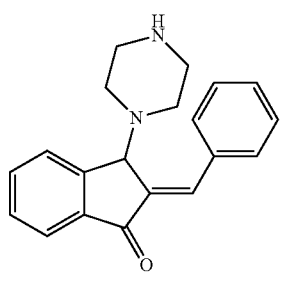
VNK-I-187
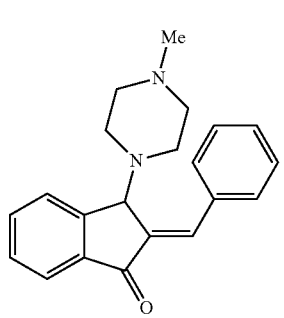
VNK-I-178
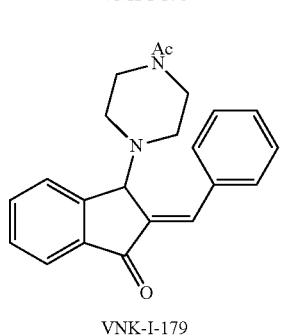
VNK-I-179

TABLE 1-continued
BCI analogs
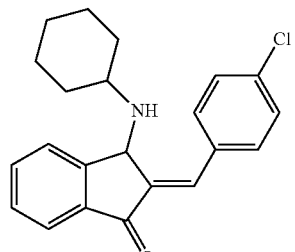
VNK-I-183  14
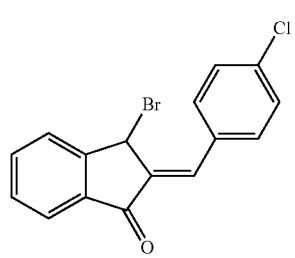 [SMILES: O=C1/C(=C/c2ccc(Cl)cc2)C(Br)c2ccccc21]
14a
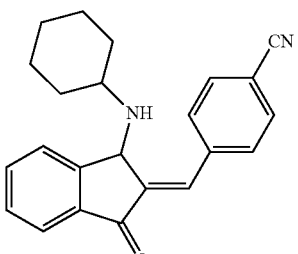
VNK-I-137  15
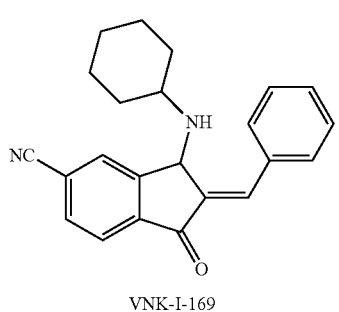 [SMILES: N#Cc1ccc2c(c1)C(NC1CCCCC1)/C(=C\c1ccccc1)C2=O]
VNK-I-132  15a
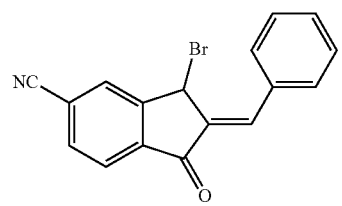 [SMILES: N#Cc1ccc2c(c1)C(Br)/C(=C\c1ccccc1)C2=O]
VNK-I-169  16
TABLE 1-continued
BCI analogs
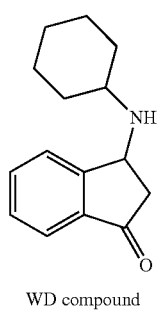 [SMILES: O=C1CC(NC2CCCCC2)c2ccccc21]
16a
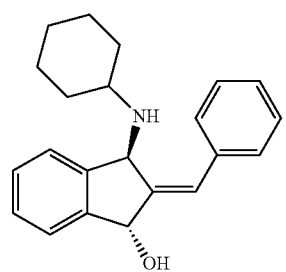
WD compound  17
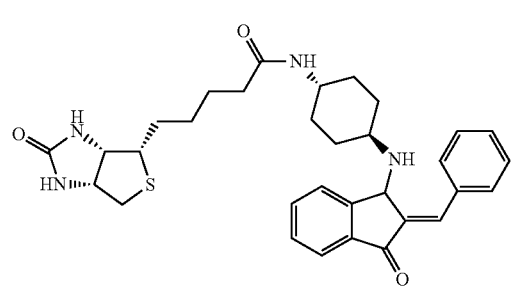
VNK-I-146  18
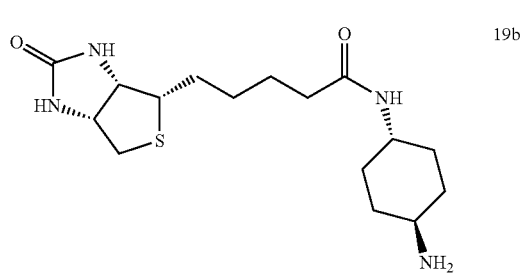
VNK-I-107  19
19b TABLE 1-continued BCI analogs

20 VNK-I-211B CSA

20a VNK-I-211A CSA

21 VNK-I-212 KG-17-C2

21a

22 VNK-I-215 KTD

22a

23 VNK-I-216 KTD

23a VNK-I-216a KTD

24 VNK-I-217 CSA

25a

25b

TABLE 1-continued

BCI analogs (Structures 25–32, 28a, 28b, 31a shown)

The compound may be an enantiopure preparation consisting essentially of an (−) or (+) enantiomer of the compound, for example (−) BCI or (+)BCI, or may be a mixture of enantiomers in either equal (racemic) or unequal proportions.

In one non-limiting embodiment of the compounds, R4 is =O. Additional examples of R2 include: t-Boc-cyclohexylamine, thiamorpholine, piperazine, methyl piperazine, acetyl piperazine, cyclopentylamine, cycloheptylamine and di-$C_{1-4}$-alkylamine.

A compound consisting of a (−) enantiomer of a compound having the formula:

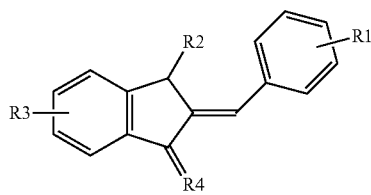

in which R1 represents one or more independently of H, halo, $C_{1-3}$ alkyl, $C_{1-3}$ alkoxyl or —CN; R2 is a primary or secondary amine; R3 is one or more independently of H, halo, $C_{1-3}$ alkyl, $C_{1-3}$ alkoxyl or —CN; and R4 is =O or —OH.

As used herein, a ring structure showing a bond/group that is not attached to any single carbon atom, for example and without limitation, depicted as

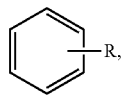

can be substituted at any position with one or more groups designated "R", and, unless indicated otherwise, each instance of R on the ring can be (independently) the same or different from other R moieties on the ring. Thus, if R is H, the group contains nothing but H groups. If R is "halo", it is a single halo (e.g., F, Cl, Br and I) group. If R is one or more independently of halo and CN, the ring may comprise one, two, three, four, halo or CN groups, such as, for example and without limitation: 2, 3, 4, or 5 chloro; 2, 3, 4, or 5 bromo; 2,3- or 3,4- or 4,5- or 2,4-dichloro; 3-bromo-4-chloro; 3-bromo-4-cyano, and any other possible permutation of the listed groups. Unless otherwise indicated, the described compounds include all stereoisomers or enantiomers and include preparations comprising one enantiomer (enantiopure compositions) and mixtures of enantiomers, such as racemic mixtures.

Also provided is a composition comprising one or more compounds of any one of claims 1-15 and a solvent or carrier, such as a pharmaceutically acceptable excipient. The compounds may be compounded or otherwise manufactured into a suitable composition for use, such as a pharmaceutical dosage form or drug product in which the compound or compounds are an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution. In one embodiment, the composition is an injectable solution or gel, which is injected at a site in which cell growth is desired, such as at the site of a wound or defect. The composition may be a topical composition, such as a lotion, cream or ointment for use in wound healing, where the topical composition is applied to a wound, such as a cut or burn.

The compounds include pharmaceutically acceptable salts. Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from the described compounds by any useful method, as are well known in the chemistry and pharmaceutical arts.

Also provided is a method of stimulating (e.g., inducing, increasing, up-regulating, etc.) cell growth in a population of cells—that is, in a culture of one or more cells, in a tissue, in an in vitro or ex vivo cell preparation obtained from a patient and optionally for replacement in the patient opr in another patient, in an organ, in an organism, etc. The method comprises contacting the cell population with a compound described herein in an amount effective to increase FGF secretion by the cell. In one embodiment, the method comprises applying the compound to a tissue in an organism, e.g., of a patient. In one embodiment, the tissue of the organism is damaged or deficient (e.g., is a wound or congenital defect). In another embodiment, the method can be used to expand a cell population or grow a tissue of a patient. For example, the method comprises obtaining cells from a patient and contacting the cells in vitro with the compound to expand the population of cells.

Figure 1:
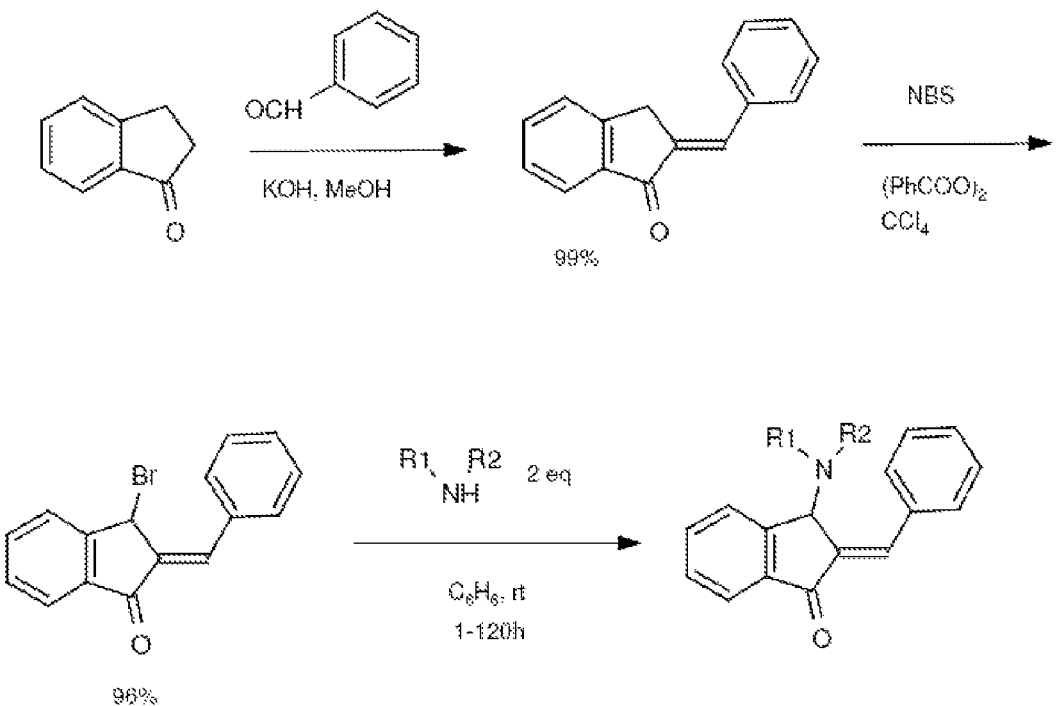
FIG. 1 shows a scheme for preparation of BCI and its analogs containing different amines.

The compounds described herein can be readily synthesized by those of ordinary skill. The BCI molecule has four distinct sites of modification (R1, R2 and R3, and the carbonyl group, R4). BCI and its analogs containing different amines were synthesized following the general procedure depicted in FIG. 1. Briefly, condensation of 1-indanone with benzaldehyde is followed by bromination of benzylideneindanone (compound 1) provides 3-bromo-2-benzyliden-1-indanone (compound 2), a general precursor for the family of analogs. Treatment of compound 2 with 2 eq of primary or secondary amines provided analogs 3-13 in high yield.

Figure 2A:
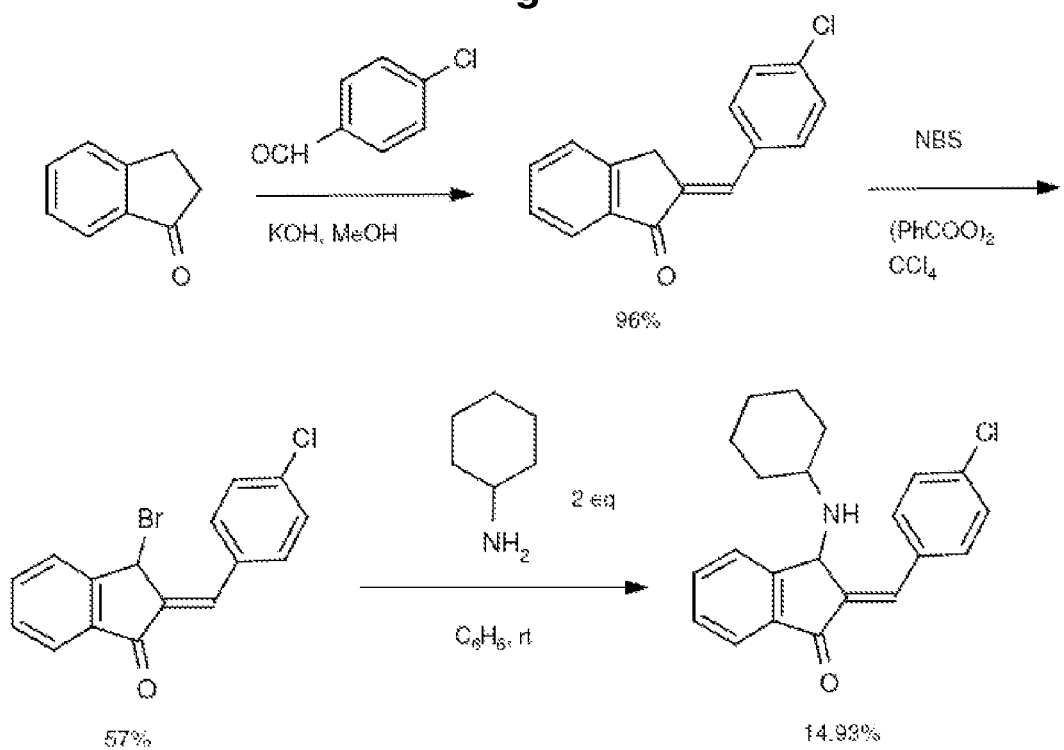
FIGS. 2A-2C depict schemes for synthesis of compounds 14-16.
Figure 2B:
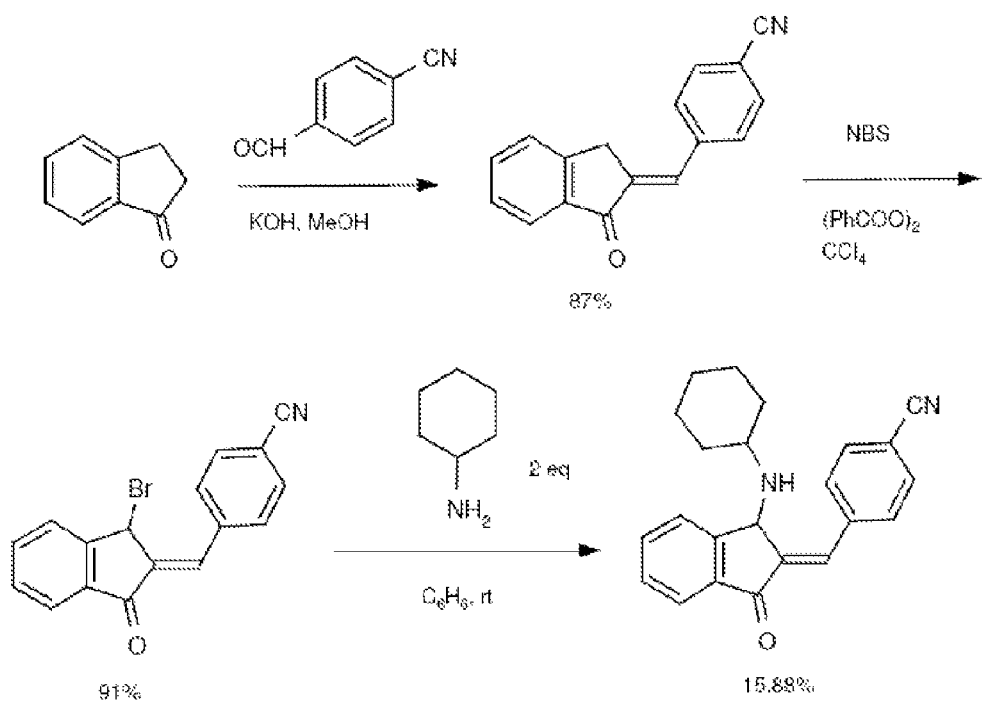
Figure 2C:
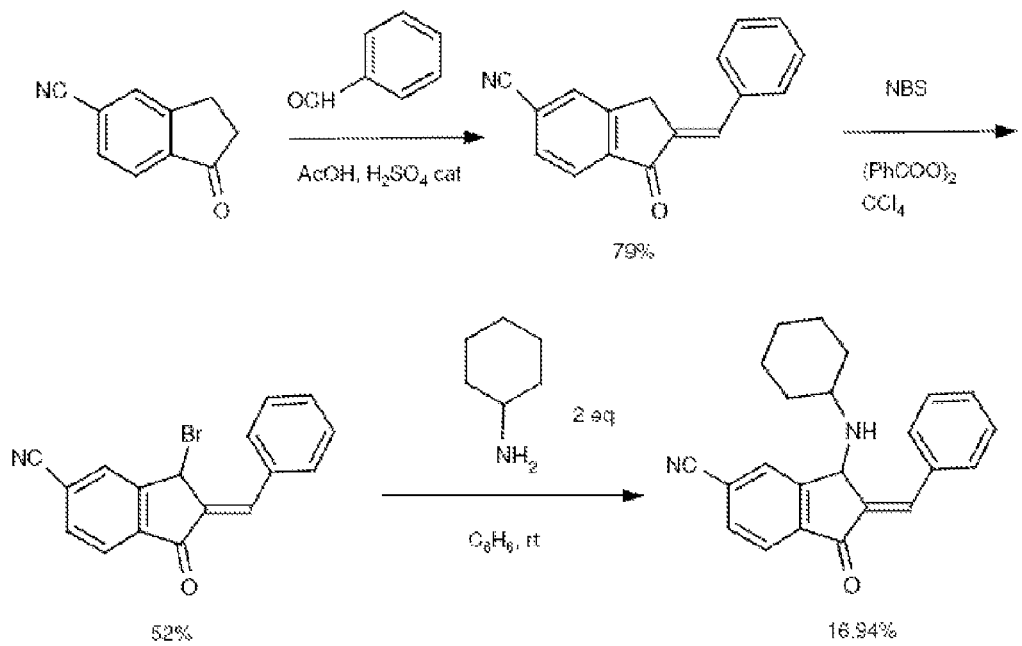
Figure 3:
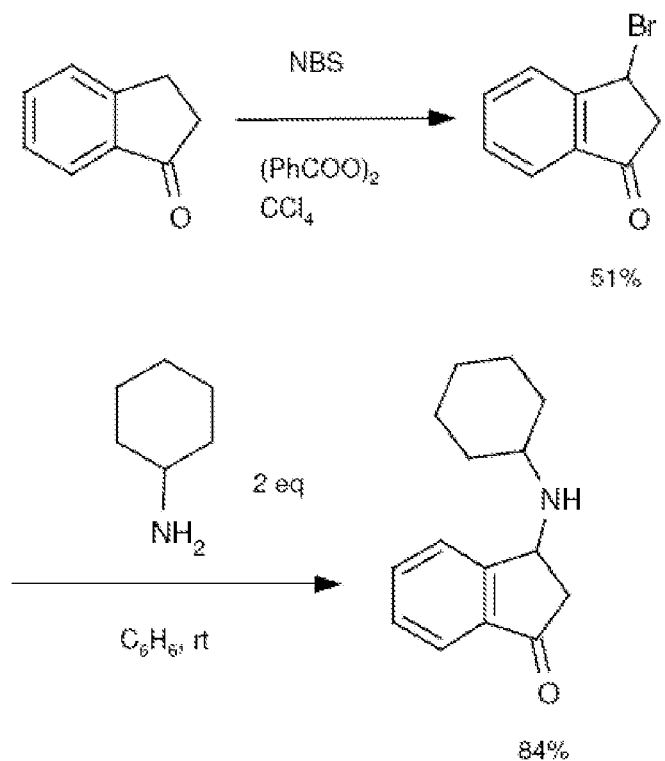
FIG. 3 depicts a scheme for synthesis of compound 17.
Figure 4:
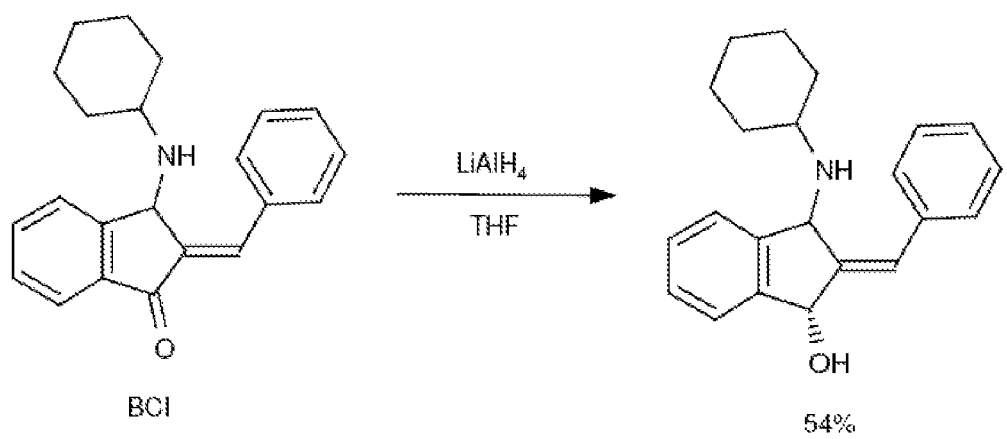
FIG. 4 depicts a scheme for synthesis of compound 18.
Figure 5:
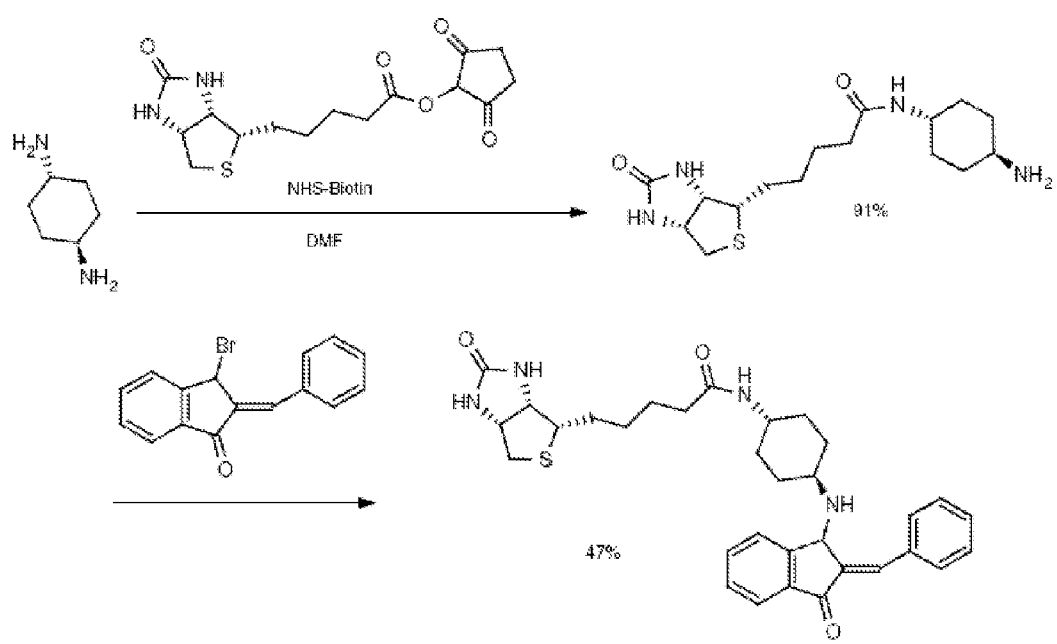
FIG. 5 depicts a scheme for synthesis of compound 19.

Variations using substituted indanones or benzaldehydes provided easy access to other BCI analogs, such as compounds 14, 15 and 16 (See, FIGS. 2A-2C). Bromination of 1-indanone and treatment of bromoindanone with cyclohexylamine provided analog 17 (ICD), which lacks the benzylidene group (see FIG. 3). LAH reduction of BCI resulted in formation of amino alcohol 18 with a trans relationship between the amine and hydroxy groups (see FIG. 4). Compound 19, which contained biotin linked to ring A, was prepared from compound 2 and the easily available monobiotinylated diaminocyclohexane (see FIG. 5). Additional synthesis schemes are described in the Examples.

EXAMPLE 1

(E)-2-benzylidene-3-(cyclohexylamino)-2,3-dihydro-1H-inden-1-one (BCI) enhances FGF Signaling Zebrafish Chemical Screens.

Tg(dusp6:d2EGFP)pt6 embryos were obtained by natural crossings and incubated at 28.5° C. until they reached 24 hpf. Five transgenic embryos were placed into each well from a 96-well plate in 200 μl of E3, and a 0.5% DMSO solution was added along with compound from each library at 10 μM. The NCI diversity set (NCI/NIH), the Natural Products library (MicroSource Discovery Systems Inc.) and Phosphatase targeted set (Chembridge) were screened in this study. (E)-2-Benzylidene-3-(cyclohexylamino)-2,3-dihydro-1H-inden-1-one (BCI; also known as NSC150117) was identified as a compound that enhanced fluorescence in treated transgenic embryos. Treated embryos were photographed under the same settings for exposure, gain and magnification for each picture using a MZFLIII (Leica) microscrope and fluorescent illumination for GFP using endow cube (Chroma Technology Corp., Rockingham, Vt.). Qimaging software and the Retiga Exi camera (Qimaging, Burnaby, BC Canada) were used to capture the images. Each experiment was repeated three times to show reproducibility of the assay and at least four of the five treated embryos exhibited the same phenotype.

Zebrafish RNA Microinjection dusp6 and XFD mRNA for microinjection studies were generated as previously described (Tsang, M. et al. *Development* 131, 2769-79 (2004)). Both Dusp5 and Spry4 ORFs were amplified by RT-PCR from 24 hpf zebrafish with the following primers:

```
Dusp5 Forward:
                                        (SEQ ID NO: 1)
5'-AACTCGAGGCCATGAAGGTCTCCAGCATAGATTGCCG-3'

Dusp5 Reverse:
                                        (SEQ ID NO: 2)
5'-AATCTAGATTAAGGCAGCGCAGTTATTGGACTC-3'

Spry4 Forward:
                                        (SEQ ID NO: 3)
5'-ACTCGAGCCATGGAGTCAAGGGTTCCTCACCACATTC-3'

Spry4 Reverse:
                                        (SEQ ID NO: 4)
5'-AATCTAGATCATGAGGCTTGTTTTTCTGGCTGAC-3'
```

Amplified PCR products were subcloned into pCS2+, sequenced verified and mRNAs were synthesized as described previously. Embryos were injected with 500 pg mRNA at the 1-2 cell stage, treated with 5 μM BCI at the 1000-cell stage and fixed at shield stage for in situ hybridization.

Chemical Complementation Assays in HeLa Cells.

These experiments were carried out essentially as described26. HeLa cells were obtained from ATCC (Manassas, Va.) and maintained in a humidified atmosphere of 5% $CO_2$ at 37° C., Dulbecco's Minimum Essential Medium (DMEM) supplemented with 10% fetal bovine serum (FBS, HyClone, Logan, Utah), and 1% penicillin-streptomycin (Life Technologies, Inc., Rockville, Md.). c-Myc-Dusp6 and c-Myc-Dusp1 (also known as CL100) (kindly provided by Dr. Stephen Keyse, University of Dundee) were subcloned into pcDNA3.1 for ectopic expression in mammalian cells50. HeLa cells (2,000) were plated in the wells of a collagen-coated 384-well plate (Falcon Biocoat) in the presence of FuGene 6 (Roche Biosciences) and c-Myc-Dusp6 or c-Myc-Dusp1 as described26. After 20 h in culture, cells were treated in quadruplicate wells for 15 min with ten two-fold concentration gradients of BCI or phenylarsine oxide (PAO) and stimulated for 15 min. with TPA (500 ng/ml). Cells were fixed and stained with Hoechst 33342 in 4% formaldehyde, permeabilized, and immunostained with a mixture of anti-pERK (1:200 dilution, Cell Signaling Technology) and anti-c-Myc (1:100 dilution, Santa Cruz Biotechnology) antibodies. Positive pERK and c-Myc-DUSP signals were visualized with AlexaFluor-594 (pERK) and Alexa-488 (c-Myc) conjugated secondary antibodies, respectively. Plates were analyzed by three-channel multiparametric analysis for p-ERK and c-Myc-DUSP intensities in an area defined by nuclear staining using the Compartmental Analysis Bioapplication on an ArrayScan II high-content reader (Cellomics, Pittsburgh, Pa.). Restoration of ERK phosphorylation by BCI in Dusp6 overexpressing cells was quantified by Kolmogorov-Smirnov (KS) statistics as described previously using DUSP-transfected and vehicle treated control wells26. One thousand individual cells were gated for Dusp-Myc expression based on c-Myc immunostaining and analyzed for ERK phosphorylation. A pERK cumulative distribution function (cdf) was established for each condition and compared to a reference cdf from Dusp-Myc expressing and vehicle-treated cells. High KS values denote large differences in ERK phosphorylation levels compared with vehicle control and indicate suppression of Dusp activity. To quantify restoration of Erk phosphorylation in the Dusp expressing cells after compound treatment, KS values for each condition were normalized to the average KS value from four wells transfected with Dusp1 or Dusp6 and treated with vehicle. Detail material and methods on in vitro phosphatase assays and chemical synthesis of BCI and related analogs are listed in Supplementary Methods online.

RT-PCR

Zebrafish embryos were treated at 24 hpf for 6 hours with BCI at 10 μM and 20 μM followed by total RNA extraction with Trizol (Invitrogen). cDNA synthesis with SuperScript II Reverse Transcriptase (Invitrogen) was performed as described by manufacture's protocol and by Tsang et al. 17. For PCR reaction, HotMasterTaq (Eppendorf) was used with the following primers:

```
Dusp6:
                                        (SEQ ID NO: 5)
For 5'-CGTTCAGAGGGGTTGTCCG-3'

Dusp6:
                                        (SEQ ID NO: 6)
Rev 5'-CTTCCCTGAACAGGAGACCC-3'

Spry4:
                                        (SEQ ID NO: 7)
For 5'-GCGGAGCAGCCCAAGATACT-3'

Spry4:
                                        (SEQ ID NO: 8)
Rev 5'-CAGGCAGGGCAAAACCAATGAG-3'

Sef:
                                        (SEQ ID NO: 9)
For 5'-CCAGTCAGGACGCGGGTTCAT-3'

Sef:
                                        (SEQ ID NO: 10)
Rev 5'-GTTAAAGTGGCGCTGCGAGTGGAG-3'
```

-continued

```
Histone H4:
                                          (SEQ ID NO: 11)
For 5'-CACGAAACCCGCCATCCGTCG-3'

Histone H4:
                                          (SEQ ID NO: 12)
Rev 5'-GTACAGAGTGCGTCCCTGCCG-3'
```

Cycle conditions were: 94° C. 30 sec, 55° C. 45 sec, 72° C. 40 sec, for 25 cycles. PCR products were resolved on 3% agarose gels.

Whole Mount In Situ Hybridization

In situ hybridization experiments were carried out as described previously (Kudoh, T. et al. *Genome Res* 11, 1979-87 (2001)). The probes eng3, krox20, sef, dusp6, gata4, nkx2.5, cmlc2, vmhc, scl, etsrp and hand2 were generated with a RNA labeling kit (Roche) (Tsang, M. et al. *Development* 131, 2769-79 (2004); Chen, J. N. et al. *Development* 122, 3809-16 (1996); Ekker, M., et al. *Development* 116, 1001-10 (1992); Liao, E. C. et al. *Genes Dev* 12, 621-6 (1998); Oxtoby, E. et al. *Nucleic Acids Res* 21, 1087-95 (1993); Pham, V. N. et al. *Dev Biol* 303, 772-83 (2007); Tsang, M., et al. *Nat Cell Biol* 4, 165-9 (2002); Yelon, D., et al. *Dev Biol* 214, 23-37 (1999); and Yelon, D. et al. *Development* 127, 2573-82 (2000)). The double fluorescent in situ hybridization protocol was described by Schoenbeck et al. (*Dev Cell* 13, 254-67 (2007)). Fluorescent in situ hybridizations were visualized by confocal microscopy. Single optical sections and z-series of flat-mounted stained embryos were collected with a confocal laser scan head (SP5, Leica Microsystems, Inc.) mounted on an inverted compound microscope (DM16000, Leica Microsystems, Inc.). Images were scanned and compiled with NIH ImageJ software (rsb.info.nih.gov/ij/).

Phosphatase Assays In Vitro.

ERK dephosphorylation assays were performed as described previously with several modifications (Lazo, J. S. et al. *J Pharmacol Exp Ther* 322, 940-7 (2007)). Briefly, recombinant His-tagged Dusp6 (1.5 ng) was incubated for 20 minutes at 25° C. in the presence of 100 µM BCI, 100 µM ICD or 1 mM sodium orthovanadate. Tyrosine and threonine phosphorylated ERK2 (New England Biolabs; 10 ng) was added and reaction mixture (30 mM Tris-HCl, pH 7.0, 75 mM NaCl, 0.67 mM EDTA, 1 mM DTT and 0.033% bovine serum albumin) was incubated at 25° C. for a further 60 min. ERK desphosphorylation was determined by Western blotting using 10% Tris-glycine gels and a monoclonal phospho-p44/42 MAPK antibody (Cell Signaling) at 1:1000 dilution. Total ERK was measured as a loading control using an anti-ERK antibody (Cell Signaling).

Cdc25B, PTP1B and VHR Assays In Vitro

Enzyme activities in the presence or absence of BCI were measured using the artificial substrate 3-O-methylfluorescein (OMFP) at concentrations equal to the Km of each enzyme (Cdc25B, PTP1B & Dusp3/VHR) and at optimal pH for individual enzyme activity in a 96-well microtiter plate assay based on previously described methods by Lazo et al. (*J Med Chem* 44, 4042-9 (2001) and Lazo, J. S. et al. *Bioorg Med Chem* 14, 5643-50 (2006)). Briefly, the standard assay conditions contained 0.02 mg/ml OMFP in assay buffer (30 mM Tris-HCl (pH8.0), 75 mM NaCl, 1 mM EDTA, 0.33% BSA and 1 mM DTT). Fluorescence emission was measured after a sixty-minute incubation period at ambient temperature using a multiwell plate reader (SpectraMax m5, Applied Biosystems; excitation 485 nm, emission 525 nm). Sodium orthovanadate (100 µM) was used as a positive control for full phosphatase inhibition. IC50 concentrations were determined from three experiments using 10 concentrations of BCI ranging from 300 µM to 15.2 nM and GraphPad Prism 5.0 software.

For OMFP based ERK2 induced activation of Dusp6, recombinant His-tagged Dusp6 was expressed from a bacterial expression vector and 250 ng were incubated with the indicated concentrations of NSC95397 or BCI. OMFP was added at its apparent Km (100 µM) (Vogt, A. et al. *J Biol Chem* 280, 19078-86 (2005)). The final reaction volume was 15 µl. After 1 h at RT, OMF fluorescence was measured on an M5 multimode reader (Molecular Devices) at excitation/emission wavelengths of 485/525 nm. To assay activated Dusp6, 210 ng or 2.1 µg of recombinant ERK2 (Cell signaling) were added to Dusp6(210 ng)/BCI(100 µM) mixtures to measure activation at 1:1 and 1:10 ratio of substrate to enzyme. OMFP was immediately added and fluorescence (ex485/em525 nm) was read every 10 min for 130 min. Fold activation was calculated at 60 mins in each experiment.

Docking Simulations

A two-step process was adopted for predicting the optimal binding poses of BCI and assessing the potential mechanism of inhibition. First, unbiased docking simulations were performed where the target protein (Dusp6) was assumed to be rigid either in the low-activity state or the high-activity state. These simulations permitted us to build two hypotheses, one of which was supported by more detailed flexible docking simulations. The method and results from the two successive steps are described in more details.

Results

Figure 6:
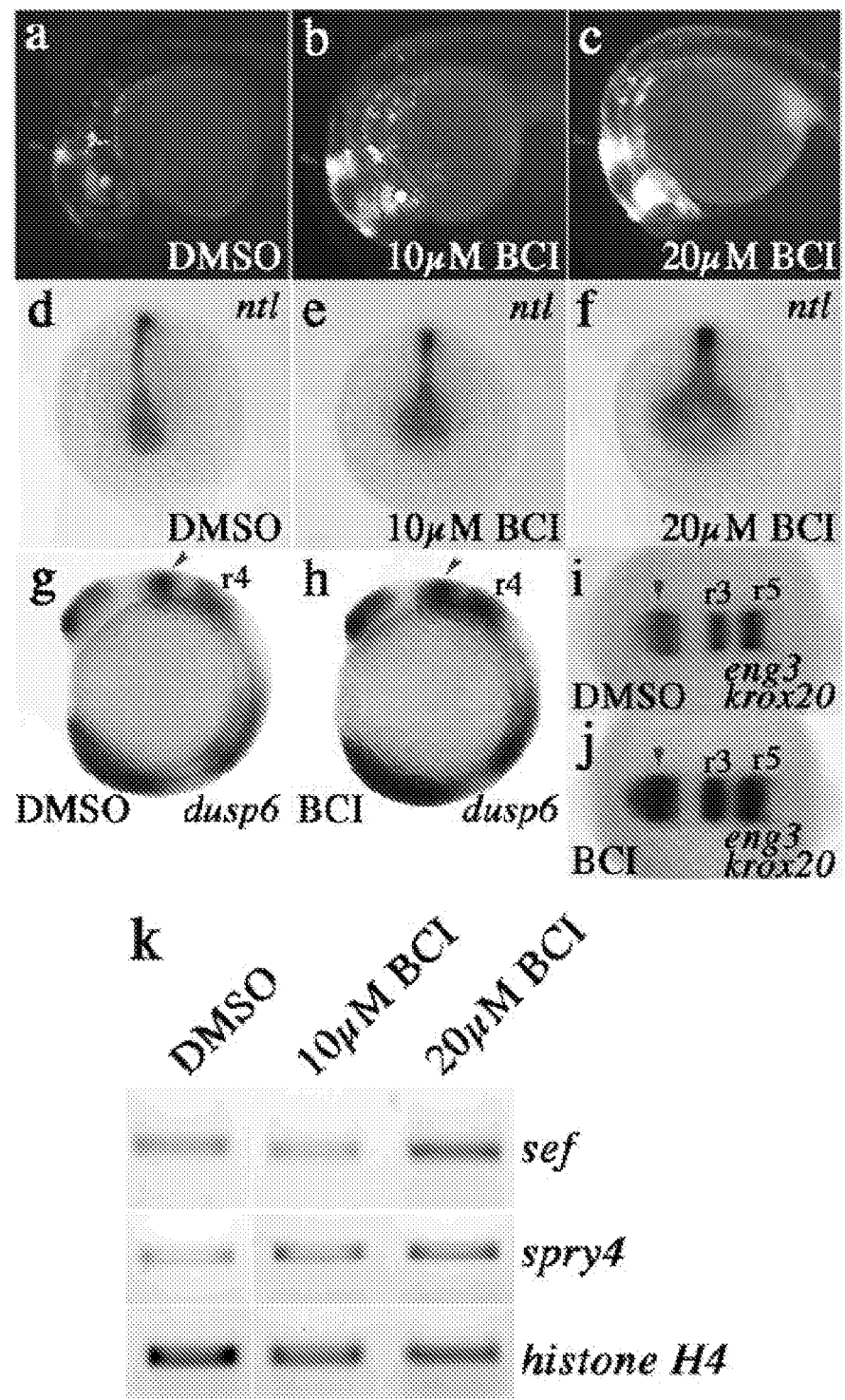
FIG. 6. Identification of a small molecule that activates FGF signaling in zebrafish. (a-c) Tg(Dusp6:d2EFP)pt6 embryos treated with BCI (b & b) exhibited increased d2EGFP fluorescence as compared to DMSO (a). (d-f) Embryos treated with BCI during gastrulation had expanded ntl expression at the 6-somite stage (e & f). (g & h) dusp6 mRNA was increased in BCI treated embryos. Note that the MHB, r4 and somites showed stronger dusp6 staining (h) than in DMSO treated (g). Red arrowheads demarcate the MHB. (i & j) BCI treatment during somitogenesis stages expanded the MHB and r3 and r5, as marked by eng3 and krox20 expression, respectively (j). (k) BCI treatment induced expression of the FGF target genes sef and spry4 as measured by RT-PCR. Histone H4 served as RNA loading control. (1) The chemical structure of BCI.

A Transgenic Zebrafish Screen Identifies a Small Molecule Activator of FGF Signaling We previously described the generation of a transgenic zebrafish line, (Tg(Dusp6:d2EGFP)pt6) that expresses destabilized green fluorescent protein (d2EGFP) under the control of FGF signaling (Molina, G. A., et al. *BMC Dev Biol* 7, 62 (2007)). Using Tg(Dusp6:d2EGFP) embryos as a biosensor for FGF signaling, we screened over 5000 diverse compounds assembled from chemical libraries for small molecule modulators of this pathway. Five transgenic embryos at 24 hours post fertilization (hpf) were arrayed into each well of a 96-well plate containing test compounds at 10 µM. d2EGFP intensity in treated embryos was visually analyzed and compared to vehicle control (0.5% DMSO) after 6-8 hours. BCI enhanced d2EGFP fluorescence in a concentration-dependent manner and was detected as early as 2 hours post treatment (FIG. 6a-c). To confirm that BCI hyperactivated FGF signaling, we treated embryos prior to gastrulation (5 hpf), and we analyzed by whole mount in situ hybridization, the expression of ntl (zebrafish brachyury), a known FGF target gene (Latinkic, B. V. et al. *Genes Dev* 11, 3265-76 (1997)). The expression of ntl was greatly expanded within the notochord and the tailbud at the 6-somite stage in BCI-treated embryos (FIG. 6d-f). Similarly, BCI treatment from the 1- to 10-somite stage resulted in a marked increase in expression of another FGF target gene, dusp6, as shown by the expansion of prospective mid-hindbrain boundary (MHB), rhombomere4 (r4) and the tailbud (FIGS. 6g & h). The expanded brain structures were confirmed as BCI increased expression of engrailed3 (eng3), which labels MHB, and krox20, which demarcates r3 and r5 identity, consistent with previous observations from FGF bead implantation studies (FIGS. 6i & j) (Maves, L., et al. *Development* 129, 3825-37 (2002)). To further demonstrate that BCI treatment hyperactivated FGF signaling, we measured an increase in the expression of sef and spry4 by semi-quantitative RT-PCR (FIG. 6k; n=3 for each gene) (Furthauer, M., et al. *Development* 128, 2175-86

Figure 7:
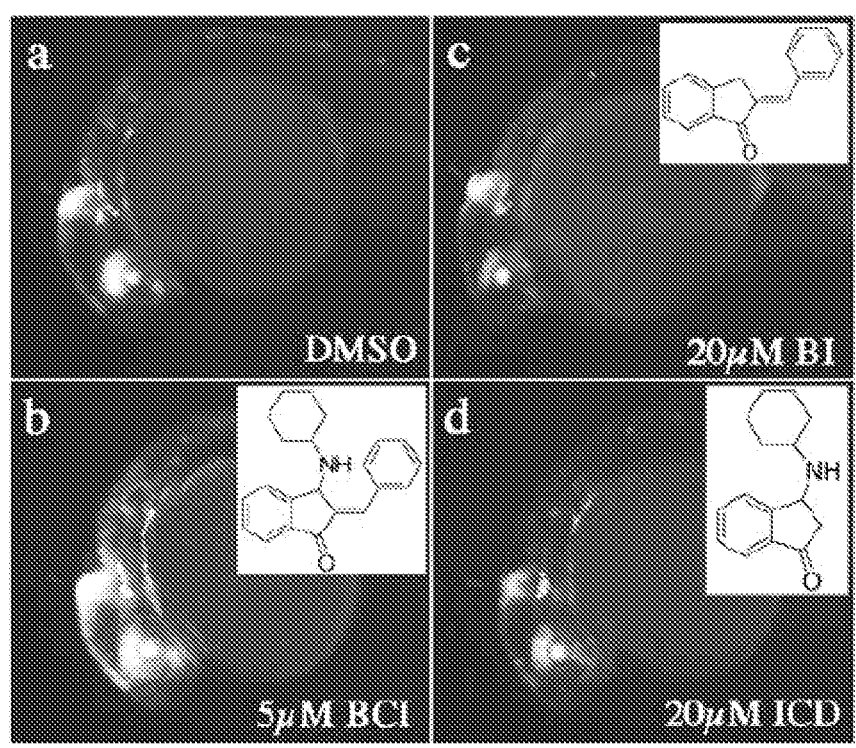
FIG. 7. BCI structure-activity relationship studies. (a-d) Lateral views of 30 hpf embryos treated with the compounds shown. d2EGFP fluorescence was enhanced in BCI-treated embryos (b), while related analogs, shown in inner panels, had no effect, even at four-fold higher concentrations (c & d). Red arrowheads label the MHB.

(2001); Tsang, M., et al. *Nat Cell Biol* 4, 165-9 (2002); and Tsang, M. et al. *Development* 131, 2769-79 (2004)). These results confirmed that BCI enhanced FGF signaling in the zebrafish embryo, resulting in the increased transcription of several FGF target genes. We next determined the BCI structural features required to enhance FGF signaling. Two analogs, (E)-2-benzylidene-2,3-dihydro-1H-inden-1-one (BI) lacking the cyclohexylamino group, and 3-(cyclohexylamino)-2,3-dihydro-1H-inden-1-one (ICD) lacking the benzylidene group were synthesized). The cyclohexylamino and benzylidene substituents were both required in enhancing d2EGFP fluorescence, as analogs lacking either group were inactive (FIG. 7).

BCI inhibits Dusp6

Figure 8N:
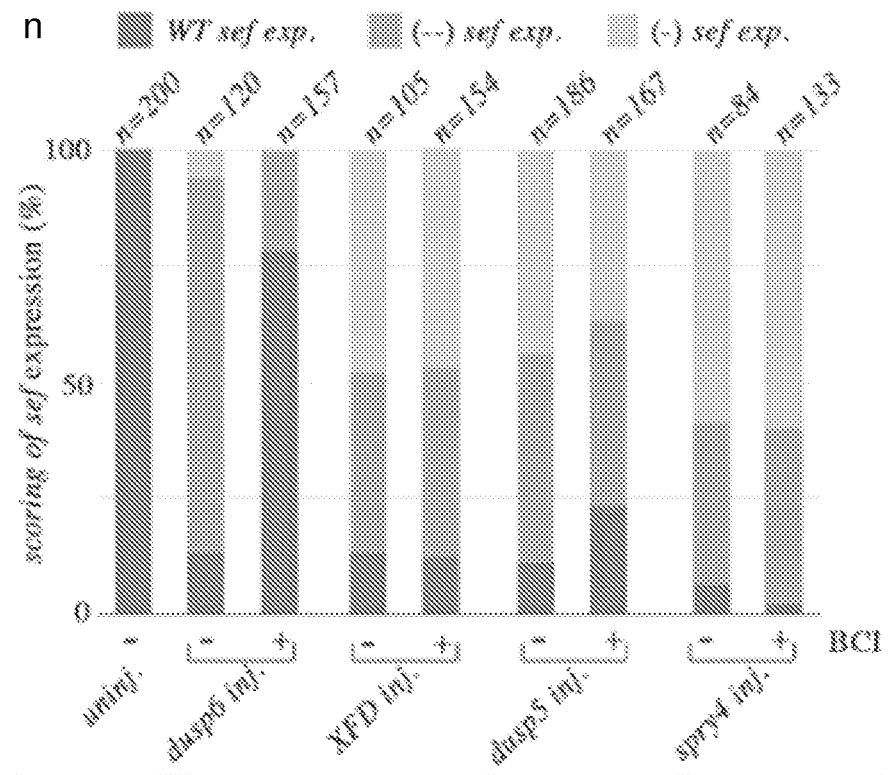
FIG. 8. BCI does not hyperactivate FGF signaling in the absence of ligand and suppresses dusp6 over-expression. (8a-8d) Lateral views of 24 hpf embryos. Tg(Dusp6:d2EGFP)pt6 embryos (8a and 8b) or Tg(Dusp6:d2EGFP)pt6; ace (8c and 8d) were treated with BCI (10 µM). The ace mutants do not show induction of d2EGFP within the MHB (red arrows) where FGF ligands are not present (3d). (3e-3m) Lateral views of shield stage embryos showing sef expression by in situ hybridization. Red brackets demarcate sef expression domain. Injection of dusp6, spry4 or dusp5 reduced sef expression (3f, 3i and 3l). BCI treatment restored sef expression in dusp6-injected embryos (i), but not in embryos injected with spry4 or dusp5 (8j and 8m). (8n) Graph depicting injection and BCI treatment results. Sef expression in mRNA-injected embryos is represented by color bars that denote normal (WT) expression in blue, weaker (-) expression in yellow and absent (--) expression in green.
Figure 9:
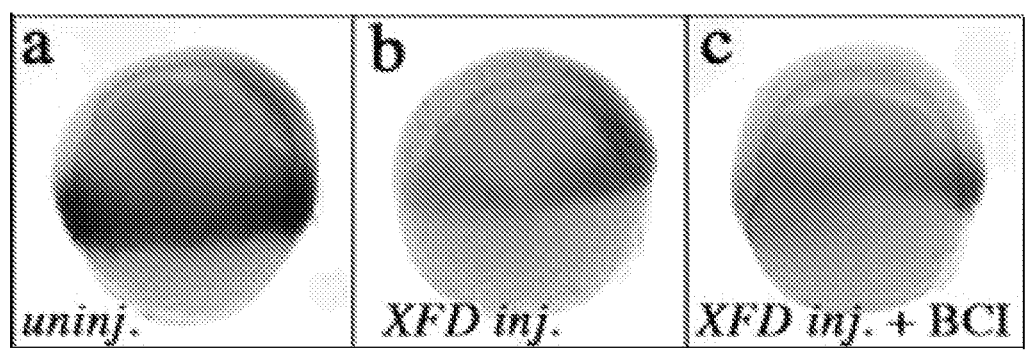
FIG. 9. Ectopic expression of XFD blocks FGF signaling that is not reversed by BCI (a-c) Lateral view of Shield stage embryos stained showing sef expression as a marker for FGF activity. (a) uninjected control. (b) Embryo injected with XFD mRNA shows a marked reduction of sef expression. (c) Embryo injected with XFD, followed by incubation with 5 µM BCI did not restore sef expression.
Figure 10E:
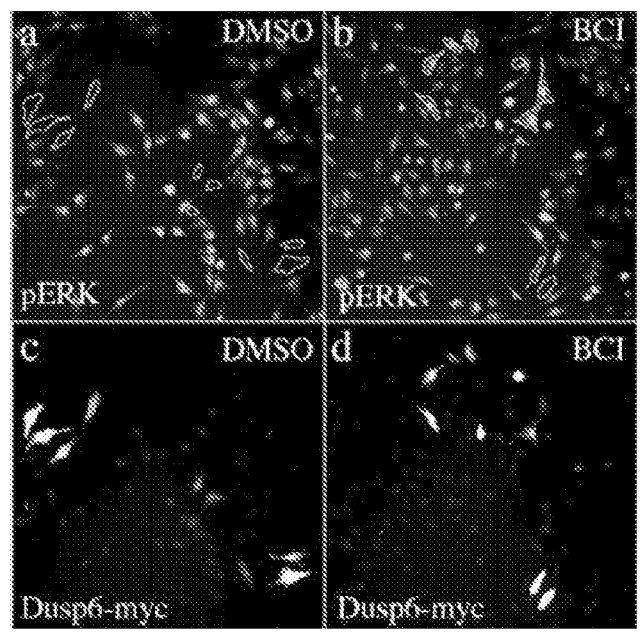
FIG. 10. BCI directly inhibits Dusp6 in both chemical complementation and in pERK2 dephosphorylation assays. (a-d) Cell-based chemical complementation assay. TPA stimulation of HeLa cells induced ERK phosphorylation (red cells in a & b). In cells overexpressing Dusp6-Myc (green cells in c), p-ERK was abolished (green cells in c & d are outlined yellow cells in a & b). In the presence of BCI, pERK levels remained high (red cells in b), even in cells expressing high levels of Dusp6-Myc (outlined yellow cells in b). (e) Quantification of pERK levels in Dusp expressing cells. Cells expressing high levels of Dusp6 (upper panel) or Dusp1 (lower panel) were identified based on c-Myc immunostaining and analyzed for ERK phosphorylation using Kolmogorov-Smirnov (KS) statistics as described in Materials and Methods. pERK levels were normalized to Dusp transfected and vehicle treated cells. BCI inhibited Dusp6 and Dusp1 with IC50 values of 16.0 µM and 11.2 µM, respectively. Data are the averages ±SD of quadruplicates from a single experiment that was repeated six times with similar results. (f) p-ERK2 in vitro dephosphorylation assay shows BCI (100 µM) specifically suppressed Dusp6 activity (lane 4) while a related analog, ICD (100 µM) did not (lane 5).
Figure 10E:
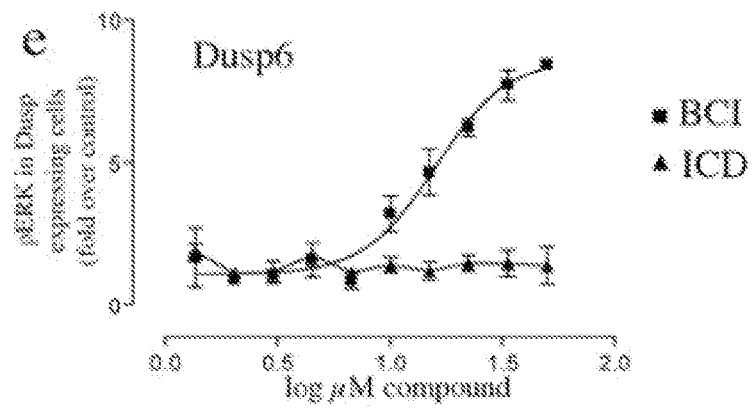
Figure 10E:
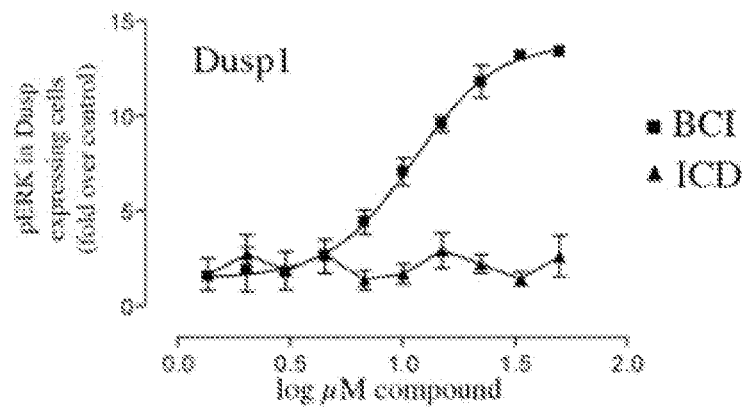

To determine the mechanism for BCI's activity and to identify a potential target, we probed where this compound acts within the RAS/MAPK pathway. In BCI-treated transgenic embryos, increased d2EGFP expression was restricted to embryonic regions where FGFs are expressed (FIGS. 1b & c). Furthermore, BCI treatment did not induce d2EGFP expression in the MHB of Tg(Dusp6:d2EGFP); ace mutant embryos, which are deficient in Fgf8 signaling (FIG. 8d) (Reifers, F. et al. *Development* 125, 2381-95 (1998)). Thus BCI did not enhance FGF signaling in the absence of ligand. We reasoned that BCI could block a feedback attenuator of the FGF pathway, thereby resulting in a net increase in transcription of target genes. To test this model, we determined if BCI could rescue phenotypes generated by ectopic expression of FGF inhibitors, Spry4, Dusp6 and a dominant negative receptor, XFD in zebrafish (Furthauer, M., et al. *Development* 128, 2175-86 (2001) and Tsang, M. et al. *Development* 131, 2769-79 (2004)). Injection of mRNA encoding dusp6, spry4, or XFD into 1-cell stage zebrafish embryos decreased sef expression (FIGS. 8f, 8k, and 8n and FIG. 9B). The addition of 5 μM BCI to dusp6-injected embryos rescued sef expression to control levels or higher (FIGS. 8g & 8n). In contrast, BCI treatment did not reverse the effects of spry4 or XFD mRNA, suggesting that BCI directly inactivated Dusp6 (FIGS. 8j and 8n and FIG. 9c). To determine if BCI could inhibit other Dusps, we first characterized zebrafish dusp5 and asked whether it could suppress FGF signaling similar to dusp6 (Qian, F. et al. *Dev Dyn* 233, 1163-72 (2005) and Sumanas, S., et al. *Blood* 106, 534-41 (2005)). Dusp5 has been shown to dephosphorylate activated ERK (p-ERK) and ectopic expression of zebrafish dusp5 inhibited sef transcription (FIGS. 8k and 8n) (Mandl, M., et al. *Mol Cell Biol* 25, 1830-45 (2005)). In contrast to observations with Dusp6 mRNA microinjections, BCI had little or no effect in reversing the phenotype caused by Dusp5 overexpression (FIGS. 8l & 8n). These observations indicated that BCI was specific for Dusp6. Although both Dusp6 and Dusp5 can dephosphorylate p-ERK and are highly conserved, their catalytic activities are quite different. Dusp6 phosphatase activity is subject to substrate binding and can be catalytically stimulated by ERK interaction (Mandl, M., et al. *Mol Cell Biol* 25, 1830-45 (2005) and Camps, M. et al. *Science* 280, 1262-5 (1998)). This substrate-induced catalytic activity has been described for several members of the Dusp family including Dusp1 (which is sensitive to BCI, as shown below), and Dusp422-24. In contrast, Dusp5 is constitutively activated and substrate binding has little consequence on catalytic rate. Thus the difference we noted with the ability of BCI to rescue Dusp6 but not Dusp5 over-expression in vivo suggested that BCI might suppress the activation of Dusp6 associated with substrate binding. Since Dusp6 directly dephosphorylates p-ERK, BCI should restore p-ERK levels in Dusp6 overexpressing cells. We tested this hypothesis in a cell-based chemical complementation assay25,26 in which HeLa cells were transiently transfected with Myc tagged human Dusp6 (Dusp6-Myc), stimulated with 12-O-tetradecanoylphorbol-13-acetate (TPA), and immunostained with anti-c-Myc (FIGS. 10c and d, green) and anti-p-ERK antibodies (FIGS. 10a and b, red), respectively. Upon TPA treatment, the RAS/MAPK pathway was activated leading to strong p-ERK staining in non-transfected cells, while in cells expressing Dusp6-Myc (FIG. 10c), p-ERK staining was abolished (FIG. 10a, Dusp6-Myc cells traced in yellow). BCI treatment of Dusp6-Myc transfected cells restored p-ERK levels after TPA addition, suggesting that BCI directly suppressed Dusp6-Myc function (FIG. 10b, Dusp6-Myc traced in yellow). In this assay, BCI also inhibited human Dusp1, whose catalytic activity, like Dusp6, is induced by substrate binding (FIG. 10e). IC50 values for DUSP6 and DUSP1 inhibition were consistent with hyperactivation of FGF signaling and d2EGFP expression at these concentrations in the zebrafish embryo (FIG. 10e). In contrast, treatment with ICD did not block Dusp6 or Dusp1 activity in the chemical complementation assays (FIG. 10e). Taken together, we have shown in biological systems BCI specifically inhibited Dusp1 and Dusp6, but not Dusp5.

Figure 10F:
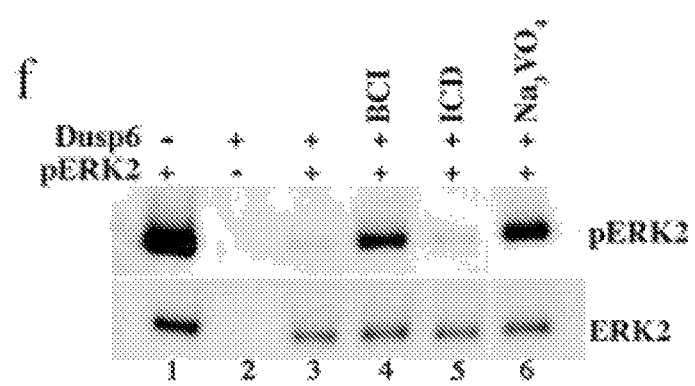
Figure 11A:
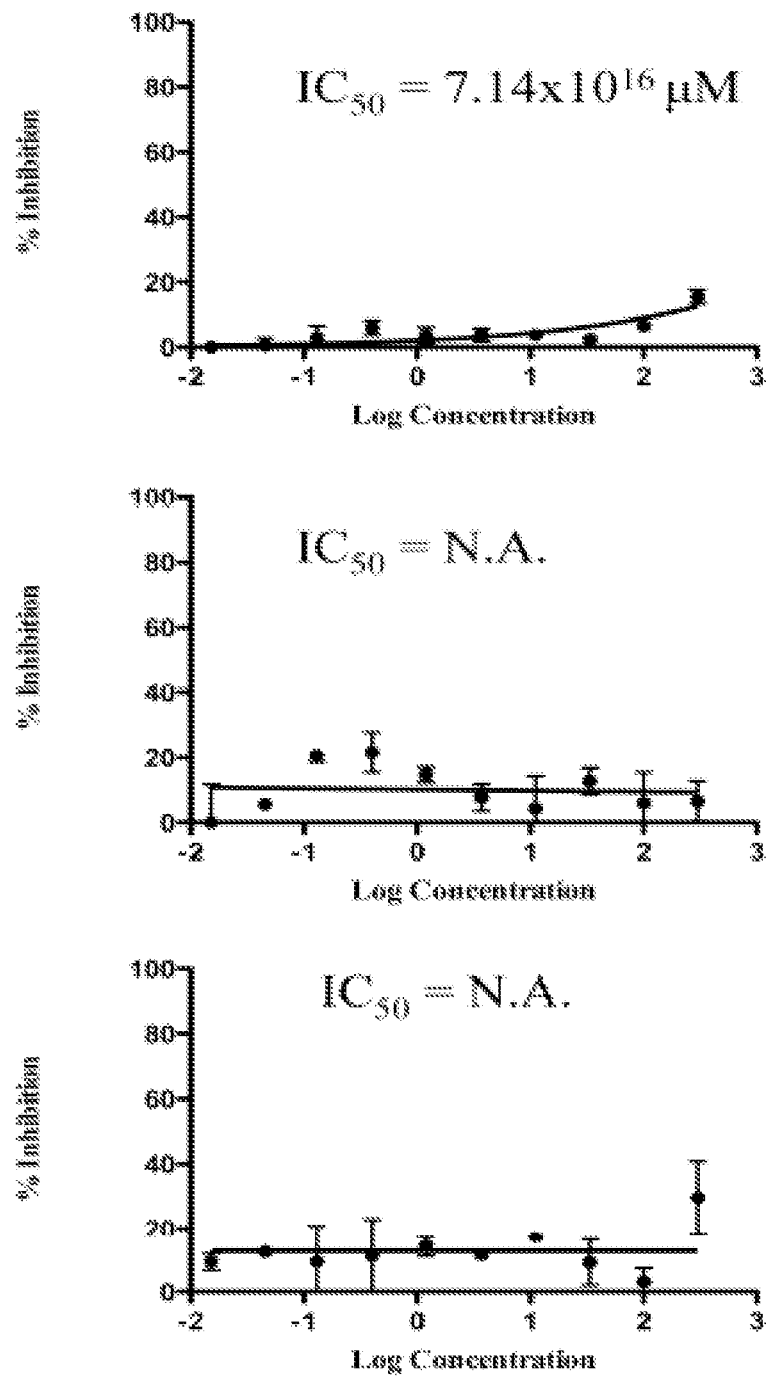
FIG. 11. BCI does not inhibit Cdc25B (11A), PTP1B (11B) or Dusp3NHR (11C). Recombinant enzymes were incubated with OMFP in the presence of increasing concentration of BCI (15.2 nM-300 µM). BCI exhibited no activity in suppressing phophatase activity by these enzymes. Assays were performed in triplicates (individual graph represents a single experiment) for each phosphatase. Sodium orthovanadate (100 µM) completely inhibited all three phosphatases and represented 100% inhibition.
Figure 11B:
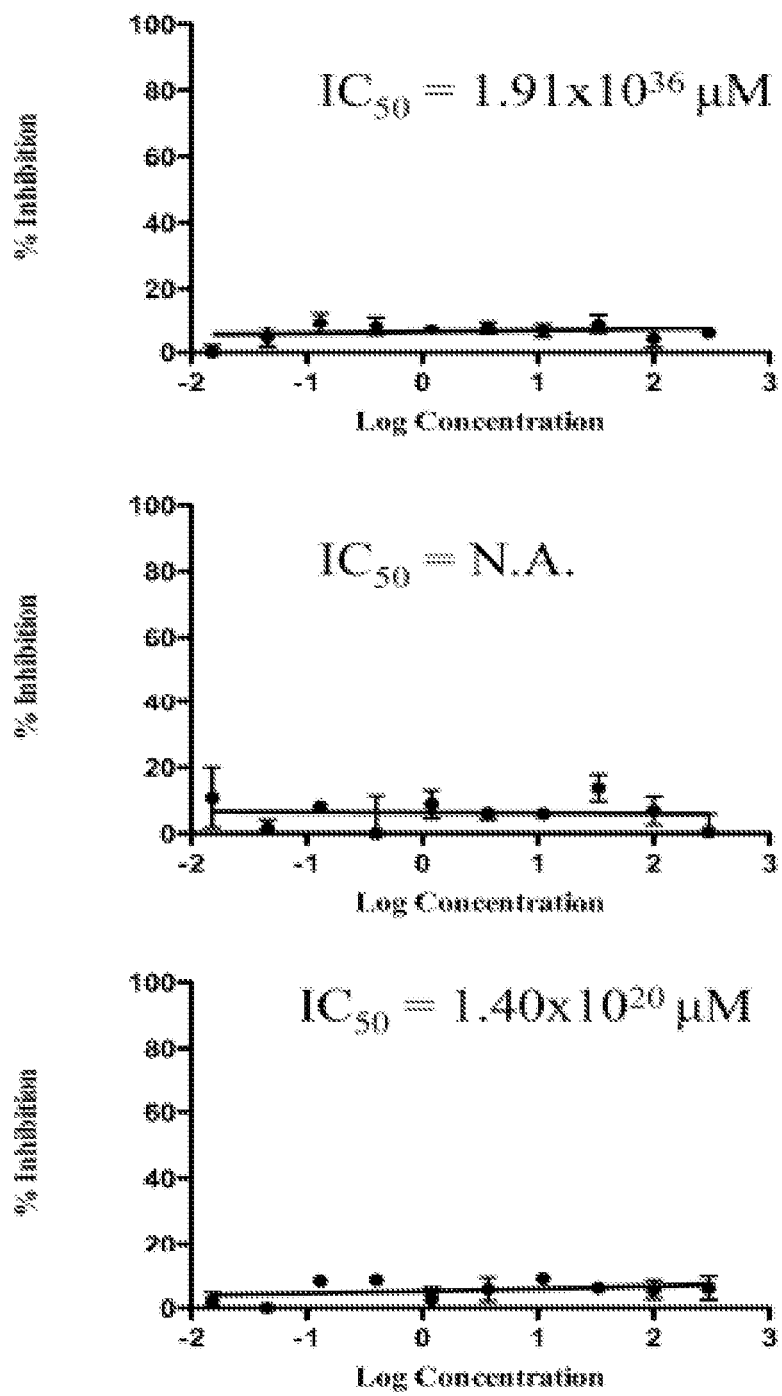
Figure 11C:
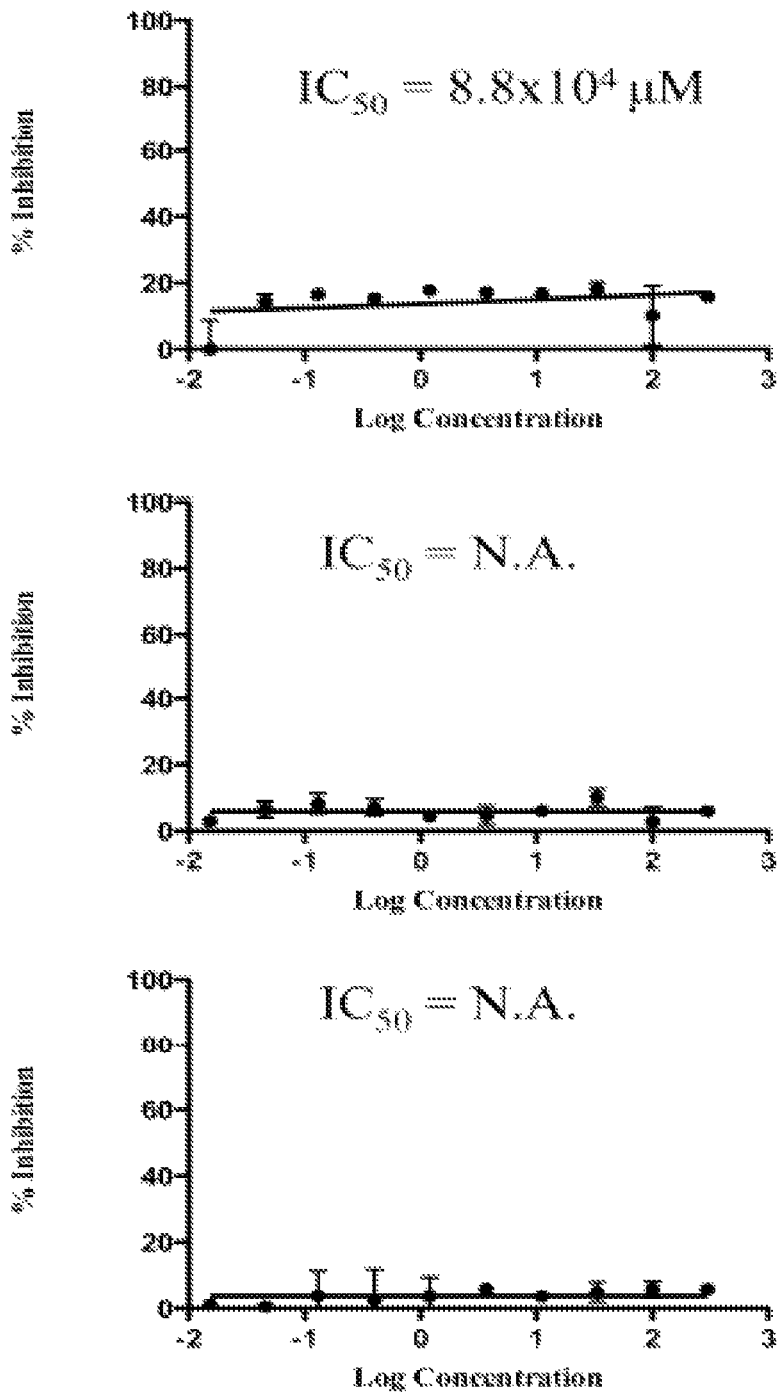

We next addressed if BCI could directly inhibit Dusp6 activity in an in vitro pERK2 dephosphorylation assay. Recombinant Dusp6 completely dephosphorylated pERK2 in vitro as determined by immunoblotting with pERK specific antibodies (FIG. 10f, Lane 3). Addition of BCI prevented Dusp6-mediated pERK2 dephosphorylation as effectively as the generic tyrosine phosphatase inhibitor sodium orthovanadate (FIG. 10f, Lane 4 and 6, respectively). ICD did not block Dusp6 activity supporting the conclusion that BCI directly inhibited Dusp6 (FIG. 10f, Lane 5). Since many known small molecule phosphatase inhibitors exhibit low selectivity we determined whether BCI could suppress phosphatase activity from several related phosphatases. BCI did not block Cdc25B (Cell division cycle 25B), PTP1B (Protein Tyrosine Phosphatase 1B) or Dusp3/VHR activity implicating specificity of BCI is limited to a set of MAP Kinase Phosphatases (FIGS. 11A-11C). The mean in vitro values (μM n=3) for BCI against of recombinant human phosphatases Cdc25B, PTP1B and VHR were >300 for each phosphatase.

Computational Modeling Reveals a Putative BCI Binding Site Within Dusp6

Crystal structures of several Dusp catalytic domains have been determined (Almo, S. C. et al. *J Struct Funct Genomics* 8, 121-40 (2007); Jeong, D. G. et al. *Proteins* 66, 253-8 (2007); Jeong, D. G. et al. *J Mol Biol* 360, 946-55 (2006); and Stewart, A. E., et al. *Nat Struct Biol* 6, 174-81 (1999)). In each case, the phosphatase domain encompasses a five/six-stranded β-sheet surrounded by five α-helices. These structures enabled us to perform unbiased docking simulations to identify potential BCI binding sites.

BCI was docked onto two different conformations of Dusp6 (MKP3): the low-activity form determined by X-ray crystallography (PDB ID: 1MKP) and the high-activity form obtained by homology modeling using ORCHESTRAR (Tripos, Inc., St. Louis, Mo.). From cluster analysis of the resulting BCI-bound conformations, we identified a number of potential binding sites on the low-activity form. The most favorable site among them was further assessed by flexible docking using multiple Dusp6 conformations generated by anisotropic network model (ANM) analysis and homology modeling. BCI was predicted to preferentially fit within a crevice between the general acid loop and helix α7, rather than interacting directly with the catalytic residues Asp262, Cys293, or Arg299. At this putative binding site, a close interaction of BCI with the backbone of the general acid loop and the sidechains of Trp264, Asn335 and Phe336 was predicted. Further docking simulations showed that BCI-Dusp1 interactions were comparable to those with Dusp6 rationalizing our observed activity data (FIG. 10e).

In further detail,

1. Unbiased Docking Simulations

BCI was docked onto two different conformations of Dusp6 (MKP3): the low-activity form determined by X-ray crystallography (PDB ID: 1MKP) (Stewart, A. E., et al. *Nat Struct Biol* 6, 174-81 (1999)) and the high-activity form obtained by homology modeling using ORCHESTRAR (Tripos, Inc., St. Louis, Mo.). We used as templates the structures of Dusp9 (MKP4; PDB ID: 2HXP; 80% sequence identity), Dusp10 (MKP5; PDB ID: 1ZZW; 47% sequence identity), and Dusp5 (VH3; PDB ID: 2G6Z; 44% sequence identity) in the high-activity state (Almo, S. C. et al. *J Struct Funct Genomics* 8, 121-40 (2007); Jeong, D. G. et al. *Proteins* 66, 253-8 (2007); and Jeong, D. G. et al. *J Mol Biol* 360, 946-55 (2006)). For BCI, 400 docking poses (200 per enantiomer) were generated using AutoDock4 for each conformation (see, Huey, R., et al. *Journal of Computational Chemistry* 28, 1145-1152 (2007) and Morris, G. M. et al. *Journal of Computational Chemistry* 19, 1639-1662 (1998)). Genetic algorithm population size was set to 250. Each docking pose was selected based on the energetic evaluation of up to $5\times10^6$ alternative conformations. The analysis of the resulting poses using an agglomerative clustering scheme revealed the clustering of a subset of binding poses in the vicinity of the active site in both conformations. In the low-activity state, the binding site was a crevice known to close upon catalytic activation of the enzyme. In the high-activity state this crevice is not accessible. Instead, a relatively more hydrophobic patch in the neighborhood of the active site was predicted to serve as an alternative binding site for the inhibitor (see, Lazo, J. S. et al. *J Pharmacol Exp Ther* 322, 940-7 (2007)). Based on these observations two potential inhibition mechanisms were hypothesized:

(i) BCI binds the low-activity form of Dusp6 and restricts the mobility of the general acid loop so as to prevent ERK2 from inducing the conformational changes that lead to Dusp6 catalytic activation. This restricts ERK2 dephosphorylation to a basal catalytic rate.

(ii) BCI binds the ERK-actived Dusp6, and prevents ERK2 from optimally orienting itself, which leads to the inhibition of ERK2 dephosphorylation. In either case, BCI was not expected to prevent Dusp6-ERK2 complex formation due to the large surface area of interaction distributed over two domains of Dusp68.

2. Flexible Docking

Toward an assessment of the more likely inhibition mechanism among those hypothesized above, we further explored the binding properties of BCI by allowing the protein to undergo structural fluctuations in the neighborhood of the two above-defined states. Backbone flexibility was deduced from normal mode analysis and homology modeling calculations. Conformations accessible near the basal-activity state were sampled by using the anisotropic network model (ANM) in combination with all-atom energy minimization (Atilgan, A. R. et al. *Biophys J* 80, 505-15 (2001)). Third, fourth, and fifth ANM slow modes were found to set in motion the catalytic Asp262 close to the catalytic cavity (Eyal, E., et al. *Bioinformatics* 22, 2619-27 (2006)). The general acid loop was also observed to have a tendency to move towards the catalytic cavity in 10 ns long unbiased molecular dynamics simulations, in line with AMN calculations. NAMD software and the Charmm force field were used for energy minimization (MacKerell Jr., et al. *J. Phys. Chem.* 102, 3586-3616 (1998) and Phillips, J. C. et al. *J Comput Chem* 26, 1781-802 (2005)). For each $\alpha$-carbon, harmonic restraints with a force constant of 40 kcal/mole/A2 were defined to drive the motions along the selected ANM modes at steps of size <0.2 Å, similar to recently introduced ANM-steered simulations (Isin, B., et al. *Biophys J* 95, 789-803 (2008)). A total of twenty conformations were sampled along the selected modes by jointly optimizing backbone and side-chain conformations (Lovell, S. C., et al. *Proteins* 40, 389-408 (2000)). As for the high-activity state, multiple models generated with MODELLER were used as targets (Jones, G., Willett, et al. *J Mol Biol* 267, 727-48 (1997)). Asp262, Trp264, and Asn335 side chains were allowed to sample rotameric states from Penultimate library (Lovell, S. C., et al. *Proteins* 40, 389-408 (2000)).

At least 1000 docking poses for the basal and activated state were generated using GOLD and cluster analysis was performed (Jones, G., Willett, et al. *J Mol Biol* 267, 727-48 (1997)). Docking poses were scored using GoldScore, which is a weighted sum of van der Waals energy and hydrogen bond energy that implicitly accounts for charged interactions (Jones, G., et al. *J Mol Biol* 245, 45-53 (1995)). The most populated and energetically favorable clusters were examined to identify the most favorable docking solution. The most favorable cluster of BCI docking poses was located in the low-activity conformation. The corresponding GoldScore averaged over all binding poses for this cluster was found to be 47.2±2.1, in favor of the hypothesis (i). Finally, as a further verification, docking simulations were performed to compare the binding properties of BCI against Dusp5, Dusp1 and Dusp6. BCI was docked onto to the crystal structure of Dusp5 (PDB ID: 2G6Z) and a model of Dusp1 based on Dusp6 structure using the same procedure as described above for Dusp6. Docking to the Dusp5 crystal structure yielded much lower docking scores (27.9±1.4) due to lack of the crevice observed in Dusp6, explaining lack of activity against this constitutively active homolog. Docking of BCI to the Dusp1 model resulted in comparable interaction but lower Goldscores (37.4±2.9). The Dusp6 movies (not shown) were generated using energy minimization with harmonic constraints based on ANM modes, implemented following the procedure described in Isin, B., et al. (*Biophys J* 95, 789-803 (2008)). Movie 1, which shows intrinsic flexibility of the general acid loop was generated using 3rd, 4th, and 5th slow modes. Movie 2, which shows the catalytic activation of Dusp6 was generated using 5% of the entire spectrum of modes in the low frequency regime.

In the zebrafish microinjection assays, BCI inhibited ectopic expression of dusp6 but not dusp5, exhibiting specificity toward certain members of this phosphatase family (FIG. 8). To understand how BCI can block Dusp6 but not Dusp5, we compared the two phosphatase crystal structures. Structural superposition of Dusp5 and Dusp6 displayed that the particular crevice in Dusp6 that accommodates BCI binding that is not accessible in Dusp5. As a result, docking of BCI onto the same region of Dusp5 phosphatase domain resulted in energetically less favorable interactions. The relative positions of Asp262 and Asp232 in the respective phosphatases Dusp6 and Dusp5 differ by 5 Å after optimal superposition of the two structures, suggesting that their basal activities are determined by the relative location of these catalytic residues (Jeong, D. G. et al. *Proteins* 66, 253-8 (2007)). It was postulated that substrate binding to Dusp6 induces a conformational shift that reorients Asp262 towards the phosphatase loop, thereby creating a high activity enzyme (Owens, D. M. et al. *Oncogene* 26, 3203-13 (2007)). In support of this model, mutation of Asp262 to asparagine did not abolish basal phosphatase activity, but suppressed catalytic activation upon ERK binding (Stewart, A. E., et al. *Nat Struct Biol* 6, 174-81 (1999)). To further understand BCI action on Dusp6 mechanistically, we explored Dusp6 dynamics by particularly focusing on the ANM modes that induce conformational changes at the general acid loop. Our analysis showed that Dusp6 possesses an intrinsic, structure induced tendency to suitably reorient its general acid loop to position Asp262 closer to the phosphatase loop. Therefore, without any intent to be bound by this theory, we proposed that BCI binding to the accessible crevice in the low-activity form effectively blocks the flexibility of this loop, thereby preventing the interaction of Asp262 with the other catalytic residues. Such constraints on functional motions are likely to inhibit Dusp6 activation induced by ERK binding.

BCI is an Allosteric Inhibitor of Dusp6

Figure 12A:
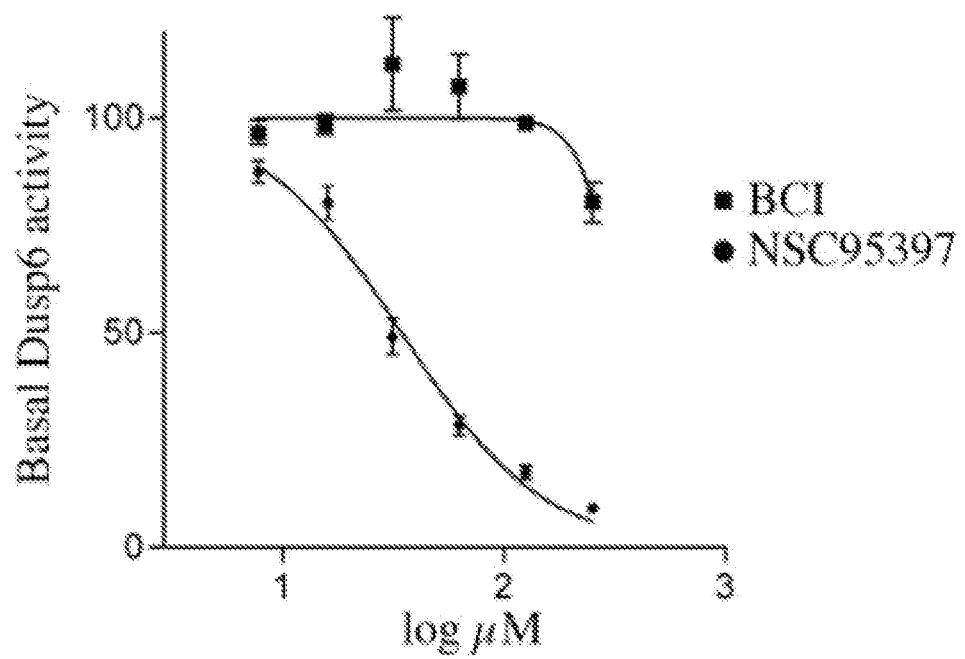
FIG. 12. BCI does not inhibit dephosphorylation of OMFP by Dusp6 (a) BCI did not suppress Dusp6 basal phosphatase activity toward OMFP. NSC95397 (2,3-bis(2-hydroxyethylthio)naphthalene-1,4-dione), a broad spectrum dual specificity phosphatase inhibitor, blocked basal Dusp6 activity toward OMFP. (b) A 10-fold excess of ERK2 (2.1 µg) stimulated (210 ng) Dusp6 dephosphorylation of OMFP by 6.5-fold and this induction was blocked by BCI. RFU, Relative Fluorescent Units were measured at excitation/emission wavelengths of 485/525 nm.
Figure 12B:
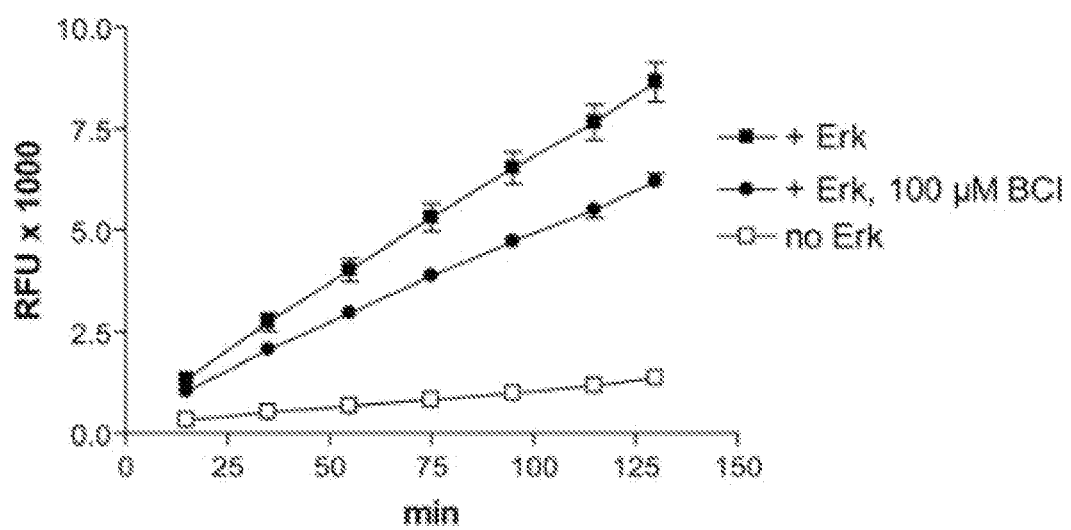

We measured the dephosphorylation of a small molecule phosphatase substrate, 3-O-methylfluorescein phosphate (OMFP), by Dusp6 in the presence or absence of ERK2. Docking simulations predicted that BCI and OMFP could simultaneously bind within the phosphatase active site with OMFP interfacing with the core catalytic residues. This suggests that BCI would not block basal Dusp6 phosphatase activity toward OMFP. Indeed, at a concentration that inhibited ERK dephosphorylation in vitro (100 µM), BCI did not inhibit basal Dusp6 activity (FIG. 12a). Addition of ERK2 protein stimulated Dusp6 dephosphorylation of OMFP threefold and this enhancement was significantly inhibited in the presence of BCI (57% inhibition) (FIG. 13). Increasing the ratio of ERK2 to Dusp6 (10:1) in the activation assay resulted in a 7-fold enhancement that was also suppressed by the addition of BCI (30% inhibition) (FIG. 12b). These data support the modeling predictions that BCI is a specific allosteric inhibitor of Dusp6 that prevents the catalytic stimulation of phosphatase activity induced by substrate binding.

The Role of Dusp6 and FGF in Regulating Heart Size

Figure 14O:
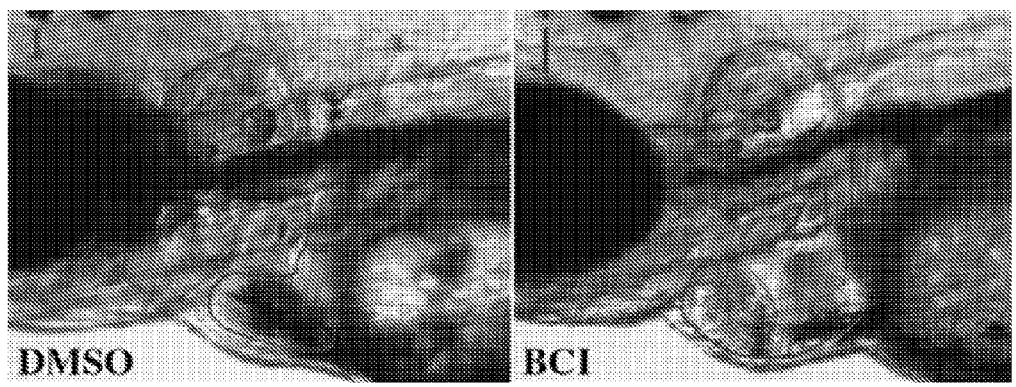
Figure 14O:
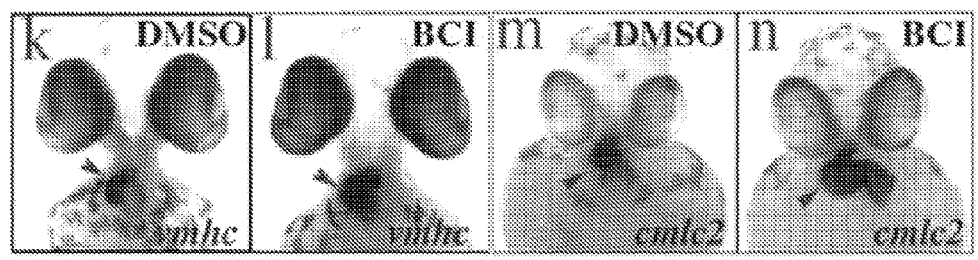
Figure 14O:
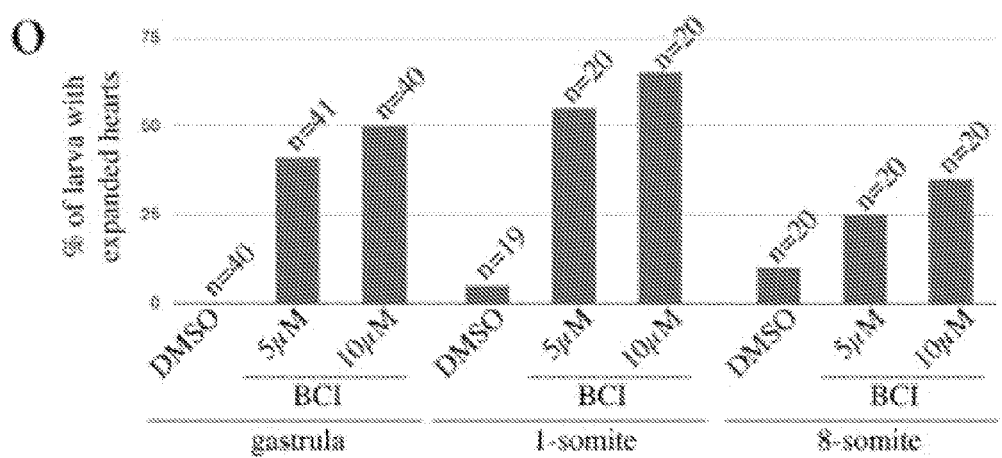

The identification of a small molecule that blocks the biologically relevant activity of Dusp6 and Dusp1 allowed us to probe the requirement for these enzymes in later developmental processes. Given that BCI could potentially block related members of the Dusp family, we examined the expression of other dusps in zebrafish. Detailed expression analyses of several dusps have been described and include dusp4, dusp1, dusp7, dusp5, and dusp22a (Qian, F. et al. *Dev Dyn* 233, 1163-72 (2005); Sumanas, S., et al. *Blood* 106, 534-41 (2005); Brown, J. L. et al. *Proc Natl Acad Sci USA* 105, 12337-42 (2008); Kudoh, T. et al. *Genome Res* 11, 1979-87 (2001); and Thisse, B. et al. Fast Release Clones: A High Throughput Expression Analysis. ZFIN Direct Data Submission (zfin.org) (2004)). Of these only Dusp6 functions as a feedback regulator of FGF/MAPK/ERK signaling and is expressed within the anterior lateral plate mesoderm, supporting the idea that this phosphatase plays a role in heart development. In early embryogenesis, Dusp6 is an important regulator of FGF signaling; knock-down with antisense morpholinos results in embryo polarity defects, which precludes the study of Dusp6's role in later development (Tsang, M. et al. *Development* 131, 2769-79 (2004)). In contrast, small molecules permit the analysis at later stages of development due to rapid and transient perturbation of their biological targets. Using BCI as a chemical probe, we asked how inhibiting Dusp6 activity would alter patterning and formation of the heart. The zebrafish heart develops from a small group of cardiac progenitor cells that can be identified by 5 hpf within the mesodermal layer of the blastula stage embryo. During gastrulation, cardiac progenitor cells undergo cellular migration to form two bilateral populations known as the anterior lateral plate mesoderm (ALPM) located just behind the MHB, and begin to express the transcription factors nkx2.5 and gata4. Studies have described a role for Fgf8 in zebrafish heart development. In embryos harboring an fgf8 mutation, both atria and ventricular cells are reduced (Marques, S. R., et al. *Dev Biol* 321, 397-406 (2008) and Reifers, F., et al. *Development* 127, 225-35 (2000)). In agreement with the notion that FGF signaling plays a role in stipulating heart size, ectopic expression of a constitutively activated FGF receptor (Fgfrl) during somitogenesis stages expanded cardiac tissue (Marques, S. R., et al. *Dev Biol* 321, 397-406 (2008)). Therefore we used BCI to test if Dusp6 limits FGF signaling and restricts cardiac progenitors and heart organ size. In BCI-treated embryos a caudal expansion of gata4 in the ALPM was observed (compare FIG. 14a & a' to 14b & b'; 81%, n=16). The gata4 caudal expansion of the ALPM corresponds to where cardiac progenitors are situated at the 10-somite stage.

Examination of nkx2.5 expression in BCI-treated embryos showed expanded cardiac progenitor pools as compared to DMSO-treated embryos, confirming a specific effect on heart precursors (compare FIGS. 14d to 15d; 91%, n=11). While we noted an expansion of cardiac progenitors, it was not clear if this event was at the expense of other lineages. Recent studies have shown that there exists a repressive interaction between the vascular and hematopoietic precursors on cardiomyocyte progenitors that determine heart organ size (Schoenebeck, J. J., et al. *Dev Cell* 13, 254-67 (2007)). We analyzed expression of scl/tall, a gene that is expressed in endothelial and blood lineages located within the rostral domain of the ALPM in BCI treated embryos from the 1-somite stage. Inhibition of Dusp6 resulted in a marked reduction in sc/expression, suggesting that activation of FGF signaling expanded cardiac tissue at the expense of blood or endothelial progenitors (compare FIGS. 14f to 14e; 93%, n=15). Likewise, etsrp, a marker for vascular fate was also reduced in BCI-treated embryos (data not shown). The loss of endothelial and hematopoietic lineages was coupled with the concomitant expansion of cardiac hand2 expression at the 10-somite stage (FIG. 14f; 32%, n=19). This surplus of cardiac progenitors was also noted at the 18-somite stage by an increase in cells positive for cardiac myosin light chain 2 (cmlc2), which specifically labels differentiated cardiomyocytes (FIG. 14h; 81% n=16). To test whether the expansion of cardiac progenitors resulted in an increase in heart tissue, we analyzed treated embryos at larval stage. Embryos were treated at 40% epiboly, with BCI or DMSO, followed by compound washout the next day and further incubation until the embryos reached 56 hpf. In BCI-treated larvae, we noted a marked expansion in cardiac tissue (FIGS. 14j & o). To define the critical period as to when Dusp6 activity limits heart organ size, we treated embryos at the 1- and 8-somite stages. We observed larger hearts at both time points, however the frequency was reduced in embryos treated at the later stage (FIG. 14o). In situ analysis with probes for ventricular myosin heavy chain (vmhc) and cmlc2 confirmed that treated embryos exhibited enlarged hearts (FIGS. 14l & n, and FIG. 15). Expansion was particularly notable for ventricular tissue, known to be sensitive to Fgf8 signaling (FIG. 14l) (Marques, S. R., et al. *Dev Biol* 321, 397-406 (2008) and Reifers, F., et al. *Development* 127, 225-35 (2000)). These results indicate that inhibition of Dusp6 by a small molecule inhibitor can induce an expansion of myocardial progenitors that ultimately increase heart size.

Discussion

The zebrafish embryo offers distinct advantages over traditional in vitro and cell-based chemical screens. With the generation of transgenic FGF reporter lines, it is possible to screen for novel compounds that modulate this pathway in vivo. In addition, live embryo screens allow for the elimination of toxic compounds and molecules that evoke non-specific effects on embryo differentiation. From a modest screen of approximately 5000 compounds, we identified BCI, a small molecule that enhanced FGF signaling. Subsequent in vitro phosphatase assays and docking simulations provided strong evidence that BCI suppressed the ERK-induced activation of Dusp6. The identification of BCI allowed us to directly probe the role of Dusp6 in heart formation during a critical period when cardiac specific transcription factors begin to be expressed and are consistent with studies when global activation of FGF signaling resulted in increased cardiac progenitors. Treatment with BCI resulted in the expansion of the cardiac field at the expense of endothelial lineages. The increase in cardiac progenitors resulted in enlarged hearts, suggesting that FGF signaling must be tightly regulated during this period to allow for proper cardiac morphogenesis to occur. The role for Dusp6 in controlling heart organ size is likely conserved with other vertebrates as disruption of Dusp6 was recently found to cause enlarged hearts (Maillet, M. et al. *J Biol Chem* 283, 31246-55 (2008)).

Previous high-throughput screens for Dusp6 and Dusp1 inhibitors involved in vitro assays with artificial substrates. Because these assays do not faithfully recapitulate phosphatase activity in a biological context, no specific Dusp6 inhibitors with in vivo activity have been identified (Ducruet, A. P., et al. *Annu Rev Pharmacol Toxicol* 45, 725-50 (2005)). The phosphatase catalytic site is highly conserved across all tyrosine phosphatases and crystal structures have revealed shallow catalytic pockets. These structural features have further hampered the identification of specific small molecule phosphatase inhibitors (Bakan, A., et al. *Curr Med Chem* 15, 2536-44 (2008)). Small molecules targeting Dusp1 identified from in vitro screens have exhibited promiscuous activity or lack potency (Lazo, J. S. et al. *Bioorg Med Chem* 14, 5643-50 (2006)). However, with the identification of a novel allosteric inhibitor and our understanding of its mechanism of action, it is possible to design new molecules based on BCI to block substrate induced Dusp function. This offers highly specific compounds to probe the role of Dusps in development, and potentially provide novel compounds for treatment of diseases that are dependent on FGF signaling such as wound repair and regeneration.

EXAMPLE 2

Synthesis of BCI

BCI was synthesized by aldol condensation of 2,3-dihydro-1H-inden-1-one with benzaldehyde, bromination and SN2 addition of cyclohexylamine for subsequent studies. (E)-2-Benzylidene-2,3-dihydro-1H-inden-1-one (BI) and 3-(cyclohexylamino)-2,3-dihydro-1H-inden-1-one (ICD) were prepared by bromination of 2,3-dihydro-1H inden-1-one and displacement of bromide with cyclohexylamine. All reactions were conducted in oven-dried glassware under a dry atmosphere. Starting materials, reagents and anhydrous solvents were purchased from commercial suppliers (Sigma-Aldrich and Fisher). Reactions were monitored by TLC on EM Science pre-coated silica gel 60 F254 plates, 250 µm layer thickness. Flash chromatography was performed over silica gel 60, 230-400 mesh. Low resolution mass spectra (MS) were obtained in electron ionization (EI) mode on a Hewlett Packard 5971 mass selective detector coupled to a Hewlett Packard 5890 Series II gas chromatograph equipped with a 30 m 5% phenyl methylsilicone capillary column from Supelco. High resolution mass spectra (HRMS) were obtained with an Applied Biosystems 4700 MALDI-TOF instrument using α-cyano-4-hydroxycinnamic acid as the matrix. Melting points were determined on a Fisher-Johns open stage apparatus and are uncorrected. $^1$H and $^{13}$C NMR spectra were recorded on a Varian Mercury spectrometer at 400 and 100 MHz, respectively, or a Bruker Avance spectrometer at 600 and 150 MHz, respectively. NMR chemical shifts were referenced to the residual CHCl$_3$ signal (7.26 ppm downfield from Me4Si) and $^{13}$C NMR chemical shifts to the solvent CDC13 signal (77.00 ppm downfield from Me4Si), respectively.

EXAMPLE 3

(E)-2-Benzylidene-2,3-dihydro-1H-inden-1-one

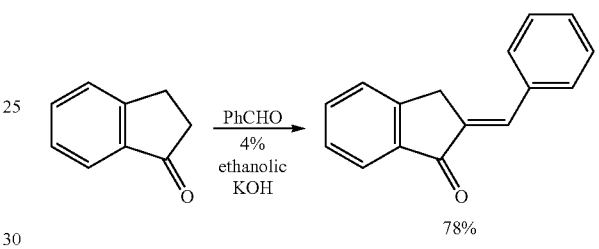

78%

(E)-2-Benzylidene-2,3-dihydro-1H-inden-1-one was synthesized as described by Hassner and Cromwell (*J Am Soc Chem* 80, 893-900 (1958)). An ice bath-cooled mixture of 2,3-dihydro-1H-indan-1-one (2.0 g, 15.1 mmol) and benzaldehyde (1.6 g, 15.1 mmol) was treated dropwise with 4% ethanolic KOH (w/v) with stirring until precipitation ceased. After an additional 1 h of stirring at room temperature, the precipitate was collected by filtration, washed with cold H$_2$O, then recrystallized from MeOH-H$_2$O to give the title compound as straw-colored crystals (2.6 g, 78% yield): M.p. 109-110° C.; $^1$H NMR (400 MHz, CDCl$_3$): δ 4.07 (s, 2H), 7.34-7.78 (m, 9H), 7.94 (d, $^1$H, J=7.6 Hz); $^{13}$C NMR (100 MHz, CDCl$_3$): δ 33.3, 125.1, 128.0, 129.1, 130.5, 131.6, 132.6, 134.8, 136.4, 137.3, 139.6, 151.4, 194.3; MS (EI) m/z (relative intensity): 220 (M$^{+\bullet}$, 55), 219 (M−1, 100). HRMS (MALDI-TOF) calc'd for m/z 221.0966 [M+H]$^+$. found 221.0970. CAS Registry No: [17434-21-8].

EXAMPLE 4

(Z)-2-Benzylidene-3-bromo-2,3-dihydro-1H-inden-1-one

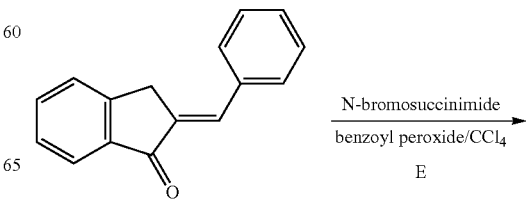

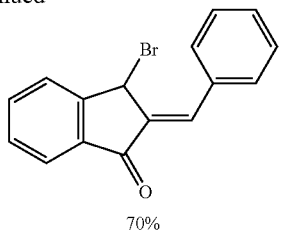

70%

(Z)-2-Benzylidene-3-bromo-2,3-dihydro-1H-inden-1-one was generated as described by Pearson et al. (*J Org Chem* 27, 3038-3044 (1962)). Briefly, (E)-2-Benzylidene-2,3-dihydro-1H-inden-1-one (1.0 g, 4.5 mmol), N-bromosuccinimide (0.8 g, 4.5 mmol) and benzoyl peroxide (61 mg, 0.25 mmol) were dissolved in 15 mL of $CCl_4$. The mixture stirred and heated to reflux for 1 h under a $N_2$ atmosphere. The mixture was cooled to r.t. and stirred an additional 1 h. After filtration and concentration from solvent under vacuum, the resulting orange solid was recrystallized three times from $CCl_4$ to give the title compound as a straw-colored solid (0.94 g, 70% yield): M.p. 118-119° C.; 1H NMR (400 MHz, $CDCl_3$): δ 6.33 (s, $^1$H, C3-H), 7.19-7.85 (m, 10H, 9 aromatic, 1 vinyl); $^{13}$C NMR (100 MHz, $CDCl_3$): δ 39.9, 127.4, 127.8, 128.4, 128.6, 128.7, 129.4, 134.1, 134.9, 135.6, 139.6, 141.9, 149.4, 192.8; MS (EI) m/z (relative intensity): 296 ($[^{77}Br]M^{+\bullet}$, 14); HRMS (MALDI-TOF) calc'd for m/z 297.0102 $[[^{77}Br]M+H]^+$. found 297.0096. CAS Registry No: [5387-50-8].

EXAMPLE 5

3-Bromo-2,3-dihydro-1H-inden-1-one

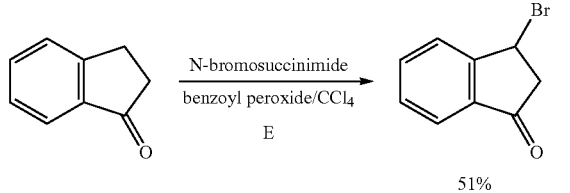

51%

3-Bromo-2,3-dihydro-1H-inden-1-one was generated as described by Treibs and Schroth 34. 2,3-Dihydro-1H-indan-1-one (528 mg, 4 mmol), N-bromosuccinimide (684 mg, 4 mmol) and benzoyl peroxide (30 mg, 0.12 mmol) were dissolved in $CCl_4$ (10 mL) and heated to reflux for 1 h under an $N_2$ atmosphere. After cooling, succinimide was removed by filtration and the filtrate concentrated under high vacuum to yield the title compound as a straw-colored oil of >99% purity as seen by GC-MS and NMR that was used without further purification (428 mg, 51% yield). $^1$H NMR (600 MHz, $CDCl_3$): δ 3.064 (dd, 1H, J=19.7, J=2.3 Hz, $CH_2$), 3.370 (dd, 1H, J=19.7 Hz, J=7.2 Hz, $CH_2$) 5.609 (dd, 1H, J=7.2 Hz, J=2.6 Hz, C3-H), 7.468-7.520 (m, 1H), 7.702-7.775 (m, 3H); $^{13}$C NMR (150 MHz, $CDCl_3$): δ 40.28, 50.30, 127.29, 128.81, 128.86, 133.72, 138.00, 204.55; MS (EI) m/z (relative intensity): 208 ($[77Br]M^{+\bullet}$, 22). CAS Registry No: [40774-41-2].

EXAMPLE 6

3-(Cyclohexylamino)-2,3-dihydro-1H-inden-1-one (ICD)

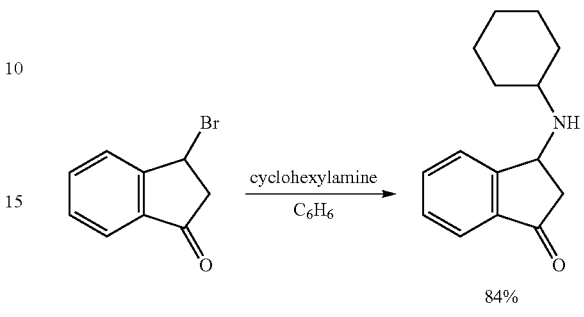

84%

3-Bromo-2,3-dihydro-1H-inden-1-one (100 mg, 475 μmol) and cyclohexylamine (94 mg, 951 μmol) were dissolved in 2 mL of dry benzene and stirred under $N_2$ until precipitation ceased (~15 min). The cyclohexylamine•HBr was removed by filtration. The filtrate was applied to a flash $SiO_2$ column that was developed with 8:1 hexanes-EtOAc to give the title compound as a clear oil (91 mg, 84% yield).

EXAMPLE 7

General Procedure for the Synthesis of 2-benzylideneindan-1-ones

Corresponding indanone (20 mmol) and corresponding benzaldehyde (20 mmol) were dissolved in methanol (50 mL). Potassium hydroxide (280 mg, 5 mmol) was added in one portion and reaction mixture was stirred at rt for 24 h. Most of solvent was removed in vacuum, and reaction was quenched with water 100 mL. Product was extracted by dichloromethane (3×100 mL), combined organic fractions were dried over $MgSO_4$, filtered and concentrated.

EXAMPLE 8

(3-Bromo-2-(4-chlorobenzylidene)indan-1-one) 14a 2-(4-chlorobenzylidene)indan-1-one (2.44 g, 9.58 mmol) was dissolved in 35 mL of $CCl_4$. N-bromosuccinimide (1.685 g, 9.58 mmol) and benzoyl peroxide (122 mg, 0.52 mmol) were added in one portion. The solution was then stirred under reflux for one hour and then filtered once cooled to room temperature. The precipitate was separated using flash column chromatography (15:1 Hexanes/EtOAc) provided 14a as white crystals.

EXAMPLE 9

(4-(1-Bromo-3-oxoindan-2-ylidenemethyl)benzonitrile) 15a 4-(1-Oxoindan-2-ylidenemethyl)benzonitrile (2.18 g, 8.9 mmol) was dissolved in carbon tetrachloride (40 mL). N-bromosuccinimide (1.58 g, 8.9 mmol) and benzoyl peroxide (100 mg) were added in one portion. Reaction mixture was reflux for 9 h, cooled down; precipitate was filtered off and washed with diethyl ether (10×30 mL) for removal of N-hydroxysuccinimide. Precipitate was dried under vacuum, provided pure 15a.

EXAMPLE 10

General Procedure for the Synthesis of Compounds 3-16 and 19-32

Corresponding 2-benzylidene-3-bromoindan-1-one 2 (299 mg, 1 mmol) or substituted analog was dissolved in benzene (10 mL). Corresponding amine (2 mmol) was added in one portion and reaction mixture was stirred for 24 h. Solvent was removed in vacuum and product was isolated by column chromatography (silica0.

EXAMPLE 11

Synthesis of 2-Benzylidene-3-cycloheptylaminoindan-1-one (5)

2-Benzylidene-3-bromoindan-1-one 2 (299 mg, 1 mmol) was dissolved in benzene (10 mL). Cycloheptylamine (255 µL, 2 mmol) was added and reaction mixture was stirred for 24 h. Solvent was removed in vacuum and 5 (271 mg, 82%) was isolated as yellow crystals by column chromatography (Hexanes/EtOAc 9:1) followed by crystallization from dichloromethane with pentane.

EXAMPLE 12

Synthesis of (2-Benzylidene-3-cyclohexylaminoindan-1-ol) 18

2-Benzylidene-3-cyclohexylamino-indan-1-one (3, BCI) (317 mg, 1 mmol) was dissolved in dry THF (15 mL) under nitrogen. Solution of LiAlH$_4$ (76 mg, 2 mmol) in dry THF (10 mL) was added dropwise at 0° C. Solution was stirred overnight and quenched with 100 µL of water followed by 100 µL of 15% NaOH followed by 300 µL of water. Precipitate was filtered off and washed with ether (3×30 mL). Combined liquid was evaporated in vacuum, and residue was separated by column chromatography on silica (DCM-MeOH—NH$_4$OH 100:1:0.5).

EXAMPLE 13

Synthesis of (5-(2-Oxohexahydrothieno[3,4-d]imidazol-4-yl)-pentanoic acid (4-amino-cyclohexyl) amide) 19b 1,4-Diaminocyclohexane (37.6 mg, 0.33 mmol) was dissolved in dry DMF (3 mL) under nitrogen. Solution of NHS-Biotin (102.3 mg, 0.3 mmol) in dry DMF (3 mL) was added to stirred solution of diamine over a 15 min period. Reaction mixture was stirred for 16 h at ambient temperature. Dilution of reaction mixture with dry Et$_2$O (50 mL) produced white precipitate. Precipitated 19b was filtered, washed with EtOAc (3×20 mL) for removing of NHS and dried in high vacuum.

EXAMPLE 14

Characterization of Compounds

Table 2 contains characterization details for the indicated compounds.

TABLE 2

Characterization of BCI analogs

| Compound | Yield | Rf | Mp (° C.) | $^1$H NMR (CDCl$_3$, 600 MHz): δ | $^{13}$C NMR (CDCl$_3$, 150 MHz): δ | HPLC/MS | HRMS |
|---|---|---|---|---|---|---|---|
| 4 VNK-I-16 | 91% | 0.20 Hex/EA 3:1 | Yellow oil | 0.98-1.07 (m, 1H), 1.22-1.64 (m, 7H), 1.79 (br.s, 1H, NH), 2.94 (quintet, J = 6.6 Hz, 1H), 5.34 (s, 1H, CHN), 7.39-7.43 (m, 1H), 7.47 (t, J = 7.2 Hz, 2H), 7.50 (d, J = 7.2 Hz, 1H), 7.66 (t, J = 7.8 Hz, 1H), 7.71 (d, J = 7.8 Hz, 1 | 23.43, 23.69, 33.24, 34.40, 55.36, 56.38, 124.04, 126.23, 128.61, 128.65, 129.69, 131.34, 134.47, 134.72, 135.93, 137.57, 138.34, 152.55, 193.54 | VNK-164 AAA >95% purity | Calcd. 304.1701 Observed 304.1699 |
| 5 VNK-I-165 | 82% | 0.25 Hex/EA 3:1 | Yellow crystals 90-92 | 1.14-1.74 (m, 13H), 2.68-2.74 (m, 1H), 5.35 (s, 1H), 7.40-7.44 (m, 1H), 7.48 (t, J = 7.2 Hz, 2H), 7.49-7.52 (m, 1H), 7.65-7.69 (m, 2H), 7.76 (s, 1H), 7.93 (d, J = 7.2 Hz, 1H), 7.96 (d, J = 7.8 Hz, 2H). | 23.77, 23.90, 28.52, 28.68, 34.24, 36.52, 54.25, 55.47, 124.21, 126.26, 128.64, 128.68, 129.75, 131.50, 134.50, 134.84, 135.93, 137.44, 138.44, 152.70, 193.71. | VNK-165 AAA >95% purity | Calcd. 332.2014 Observed 332.2007 |
| 6 VNK-I-149 | 69% | 0.25 Hex/EA 3:1 | Orange crystals 153-155 | 3.92 (br.s, 1H, NH), 6.01 (s, 1H), 6.78 (d, J = 8.4 Hz, 2H), 6.81 (t, J = 7.8 Hz, 1H), 7.24 (t, J = 7.8 Hz, 2H), 7.29-7.35 (m, 3H), 7.48 (t, J = 7.8 Hz, 1H), 7.54 (t, J = 7.8 Hz, 1H), 7.63 (d, J = 7.8 Hz, 1H), 7.68 (d, J = 6.6 Hz, 2H), 7.80 (d, J = 1.2 Hz, 1H), 7.90 (d, J = 7.2 Hz, 1H) | 53.50, 113.64, 118.53, 124.02, 125.41, 128.71, 129.15, 129.59, 130.15, 132.07, 133.68, 135.33, 136.32, 136.78, 137.16, 146.93, 152.68, 192.81 | VNK-149 >95% purity | Calcd. 312.1388 Observed 312.1390 |
| 7 VNK-I-147 | 81% | 0.55 Hex/EA 1:1 | Slightly yellow crystals 140-142 | 1.34-1.39 (m, 2H), 1.46-1.54 (m, 4H), 2.43 (br.s, 2H), 2.66-2.73 (m, 2H), 5.04 (d, J = 0.6 Hz, 1H, CHN), 7.39-7.43 (m, 1H), 7.45-7.52 (m, 3H), 7.61-7.67 (m, 2H), 7.74 (d, J = 1.2 Hz, 1H), 7.94 (d, J = 7.8 Hz, 1H), 8.08 (dd, J = 7.8 Hz, J = 1.2 Hz, 2H) | 24.69 (CH$_2$), 26.49 (CH$_2$), 50.15 (CH$_2$N), 65.04 (CHN), 124.17 (CH), 126.81 (CH), 128.39 (CH), 128.66 (CH), 129.69 (CH), 132.63 (CH), 133.96 (CH), 135.12 (C-q), 136.86 (CH), 137.83 (C-q), 138.37 (C-q), 149.68 (C-q), 193.65 (C═O) | VNK-147 >95% purity | Calcd. 304.1704 Observed 304.1700 |
| 8 VNK-I-53 | 89% | 0.4 Hex/EA 1:1 | Yellow crystals 179-181 | VNK-I-053H: 0.89 (quin.d, J = 12.6 Hz, J = 3.0 Hz, 2H), 1.05 (quin., J = 13.2 Hz, 2H), 1.24-1.31 (m, 1H), 1.40 (br.s., 9H), 1.43 (s, 1H), 1.58 (d, J = 12.6 Hz, 1H), 1.76 (dt, J = 12.0 Hz, J = 2.4 Hz, 1H), | VNK-I-053CC: 28.39, 31.80, 31.91, 32.48, 33.29, 49.15, 51.81, 55.45, 79.06, 124.10, 126.11, 128.72, 129.86, 131.31, | VNK-053 >95% purity | Calcd. 433.2491, Observed 433.2491 |

TABLE 2-continued

Characterization of BCI analogs

| Compound | Yield | Rf | Mp (° C.) | $^1$H NMR (CDCl$_3$, 600 MHz): δ | $^{13}$C NMR (CDCl$_3$, 150 MHz): δ | HPLC/ MS | HRMS |
|---|---|---|---|---|---|---|---|
| | | | | 1.83 (d, J = 12.0 Hz, 1H), 2.30 (d, J = 4.8 Hz, 1H), 3.26 (br.s., 1H), 4.34 (br.s., 1H), 5.35 (d, J = 1.2 Hz, 1H), 7.38-7.50 (m, 4H), 7.62-7.67 (m, 2H), 7.75 (d, J = 1.2 Hz, 1H), 7.85 (d, J = 7.2 Hz, 1H), 7.89 (d, J = 7.2 Hz, 1H) | 134.68, 134.74, 136.11, 137.40, 138.09, 152.78, 155.16, 193.52 | | |
| 9 VNK-I-148 | 81% | 0.45 Hex/ EA 1:1 | Yellow crystals 138-140 | 2.47 (br.s, 2H), 2.73 (br.s, 2H), 3.62 (t, J = 4.5 Hz, 4H, CH$_2$O), 5.08 (d, J = 0.6 Hz, 1H, CHN), 7.42-7.50 (m, 3H), 7.51-7.55 (m, 1H), 7.64 (t, J = 3.0 Hz, 2H), 7.76 (d, J = 1.2 Hz, 1H), 7.93 (d, J = 7.2 Hz, 1H), 7.99 (d, J = 7.2 Hz, 2H) | 49.05 (CH$_2$N), 64.41 (CHN), 67.29 (CH$_2$O), 124.31 (CH), 126.86 (CH), 128.49 (CH), 129.08 (CH), 129.96 (CH), 132.36 (CH), 134.28 (CH), 134.82 (C-q), 136.64 (C-q), 137.28 (CH), 138.38 (C-q), 148.71 (C-q), 193.17 (C=O) | VNK-148 >95% purity | Calcd. 304.1338 Observed 304.1447 |
| 10 VNK-I-177 | 87% | 0.30 Hex/EA 3:1 | Slightly yellow crystals 143-145 | 2.50-2.62 (m, 4H), 2.73-2.85 (m, 2H), 2.95-3.05 (m, 2H), 5.09 (d, J = 1.2 Hz, 1H, CHN), 7.44 (d, J = 6.6 Hz, 1H), 7.47 (t, J = 7.2 Hz, 2H), 7.52 (ddd, J = 8.4 Hz, J = 6.0 Hz, J = 3.0 Hz, 1H), 7.65-7.68 (m, 2H), 7.77 (d, J = 1.8 Hz, 1H), 7.96 (t, J = 8.4 Hz, 2H), 7.97 (s, 1H) | 28.41, 51.71, 65.80, 124.33, 126.65, 128.42, 129.01, 129.96, 132.41, 134.40, 134.66, 136.69, 137.30, 138.24, 149.04, 193.16 | VNK-177 >95% purity | Calcd. 322.1266 Observed 322.1269 |
| 11 VNK-I-187 | 42% | 0.20 DCM | Yellow crystals 245-248 | 2.20-2.70 (s, 1H, CHN), 4.97 (s, 1H), 7.28-7.33 (m, 3H), 7.42 (d, J = 7.8 Hz, 1H), 7.50 (t, J = 7.2 Hz, 1H), 7.55 (t, J = 7.2 Hz, 1H), 7.74 (d, J = 0.6 Hz, 1H), 7.91 (dd, J = 6.6 Hz, J = 1.8 Hz, 2H), 7.94 (d, J = 7.2 Hz, 1H) | 64.18, 124.20, 126.83, 128.35, 128.84, 129.74, 132.41, 134.18, 134.83, 137.09, 137.17, 138.24, 149.08, 193.39 | | Calcd. 305.1654 Observed 305.1652 |
| 12 VNK-I-178 | 92% | 0.55 DCM/ MeOH/ NH$_4$OH 90:10:1 | Yellow oil | 2.21 (s, 3H, CH$_3$), 2.25-3.00 (m, 8H), 5.08 (s, 1H, CHN), 7.42 (t, J = 7.2 Hz, 1H), 7.46 (t, J = 7.2 Hz, 2H), 7.48 (t, J = 7.2 Hz, 1H), 7.59 (td, J = 7.2 Hz, J = 1.2 Hz, 1H), 7.65 (d, J = 7.8 Hz, 1H), 7.74 (d, J = 1.2 Hz, 1H), 7.92 (d, J = 7.2 Hz, 1H), 8.01 (d, J = 1.2 Hz, 2H) | 45.99, 55.42, 64.12, 124.22, 126.95, 128.45, 128.92, 129.80, 132.49, 134.14, 134.96, 137.09, 137.20, 138.29, 149.04, 193.39 | VNK-178 >95% purity | Calcd. 319.1810 Observed 319.1800 |
| 13 VNK-I-179 | 86% | 0.20 EtOAc | Yellow oil | 1.98 (s, 3H, CH$_3$), 2.23 (t, J = 7.8 Hz, 1H), 2.57-2.62 (m, 1H), 2.65-2.69 (m, 1H), 2.77 (t, J = 7.8 Hz, 1H), 3.20 (t, J = 9.0 Hz, 1H), 3.29 (t, J = 9.0 Hz, 1H), 3.33-3.39 (m, 1H), 3.81 (d, J = 10.2 Hz, 1H), 5.16 (s, 1H, CHN), 7.41 (t, J = 6.6 Hz, 1H), 7.45 (t, J = 7.2 Hz, 2H), 7.50 (t, J = 7.2 Hz, 1H), 7.57 (d, J = 7.2 Hz, 1H), 7.63 (t, J = 7.2 Hz, 1H), 7.76 (br.s, 1H), 7.91 (d, J = 7.8 Hz, 1H), 7.95 (d, J = 7.8 Hz, 2H) | 21.28 (CH$_3$), 41.82 (CH$_2$), 46.60 (CH$_2$), 48.02 (CH$_2$), 49.36 (CH$_2$), 64.20 (CHN), 124.43 (CH), 126.69 (CH), 128.50 (CH), 129.21 (CH), 130.06 (CH), 132.29 (CH), 134.41 (CH), 134.64 (Cq), 136.43 (Cq), 137.43 (CH), 138.29 (Cq), 148.42 (Cq), 168.88 (C=O(N)), 193.01 (C=O) | VNK-179 >95% purity | Calcd. 347.1760 Observed 347.1766 |
| 14 VNK-I-183 | 93% | | 118-122 | 0.99-1.14 (m, 5H), 1.37 (d, J = 12 Hz, 2H), 1.53-1.56 (m, 3H), 1.65-1.68 (m, 1H), 1.77 (d, J = 12.6 Hz, 1H), 2.45-2.49 (m, 1H), 7.44 (dd, J = 6.6 Hz, J = 1.8 Hz, 2H), 7.51 (td, J = 7.2 Hz, J = 1.2 Hz, 1H), 7.65-7.68 (m, 3H) 7.93 (d, J = 7.8 Hz, 1H), 7.97 (d, J = 8.4 Hz, 2H). | 24.83, 24.89, 25.85, 33.60, 34.97, 124.26, 126.06, 128.73, 128.87, 133.13, 133.28, 134.72, 135.81, 137.30, 138.79, 152.71, 193.50 | VNK-183AAA >95% purity | Calcd. 352.1468 Observed 352.1466 |
| 15 VNK-I-137 | 88% | 0.50 Hex/ EA 1:1 | Yellow crystals 174-176 | 0.97-1.83 (m, 11H), 2.49 (tt, J = 9.6 Hz, J = 3.6 Hz, 1H), 5.30 (s, 1H), 7.53 (t, J = 7.2 Hz, 1H), 7.65 (d, J = 7.2 Hz, 1H), 7.69 (s, 1H), 7.71 (t, J = 7.2 Hz, 1H), 7.75 (d, J = 8.4 Hz, 2H), 7.94 (d, J = 7.8 Hz, 1H), 8.17 (d, J = 8.4 Hz, 2H) | 24.80, 25.81, 33.45, 34.95, 52.58, 55.00, 112.62, 118.67, 124.46, 126.06, 128.95, 131.29, 131.72, 132.16, 132.18, 133.65, 135.12, 137.02, 139.28, 141.44, 152.60, 193.17 | VNK-137 >95% purity | Calcd. [M + H] 343.1810 Observed 343.1763 |
| 16 VNK-I-169 | 94% | | 162-164 | 0.94 (m, 2H), 1.04 (m, 3H), 1.24 (d, J = 12.6 Hz, 2H), 1.49 (d, J = 9.0 Hz, 2H), 1.57 (d, J = 12.0 Hz, 2H), 2.28 (m, 1H), 5.41 (s, 1H), 7.47 (m, 3H), 7.76 (d, J = 8.4 Hz, 1H), 7.84 (s, 1H), 7.87 (d, J = 7.8 Hz, 2H), 7.98 (d, J = 6.6 Hz, 2H) | 24.79, 24.97, 25.83, 34.02, 34.82, 52.85, 55.41, 117.46, 118.50, 124.85, 129.98, 130.53, 130.55, 131.68, 132.35, 134.35, 137.13, 138.26, 140.47, 153.34, 192.31 | VNK-169 >95% purity | Calcd. [M + H] 343.1810 Observed 343.1808 |
| 17 WD compound data | 84% | | oil | 1.06-1.21 (m, 4H), 1.21-1.34 (m, 2H), 1.59-1.65 (m, 1H), 1.70-1.83 (m, 3H), 1.95-2.05 (m, 1H), 2.45 (dd, J = 18.6 Hz, J = 3.0 Hz, 1H), 2.60-2.68 (m, 1H), 2.95 (dd, J = 6.7 Hz, J = 18.6 Hz, 1H), 4.52 (dd, J = 6.6 Hz, J = 3.0 Hz, 1H), 7.38 (dd, J = 7.3 Hz, J = 0.9 Hz, 1H), 7.59 (dd, J = 7.2 Hz, J = 0.9 Hz, 1H), 7.63 (d, J = 7.7 Hz, 1H), 7.69 (d, J = 7.7 Hz, 1H) | 24.73, 24.92, 25.94, 33.12, 34.47, 46.01, 53.07, 55.23, 123.14, 125.83, 128.41, 134.73, 136.52, 156.61, 204.77 | | Calcd. 230.1545 Observed 230.1550 |
| 18 VNK-I-146 | 54% | 0.30 DCM/ MeOH/ NH$_4$OH 90:10:1 | oil | 1.05-1.30 (m, 6H), 1.49 (d, J = 9.6 Hz, 1H), 1.57-1.64 (m, 2H), 1.71-1.77 (m, 1H), 2.01 (d, J = 12 Hz, 1H), 2.50-2.56 (m, 1H, CHN), 5.15 (s, 1H, CH—NCy), 5.77 (s, 1H, CHOH), 6.93 (s, 1H), 7.30 (dd, J = 7.8 Hz, J = 7.2 Hz, 1H), 7.31-7.34 (m, 2H), 7.35-7.38 (m, 1H), 7.39 (t, J = 7.8 | 25.00 (CH$_2$), 25.11 (CH$_2$), 26.10 (CH$_2$), 32.74 (CH$_2$), 34.64 (CH$_2$), 53.25 (CH), 57.49 (CH), 76.25 (CHOH), 124.62 (CH), 125.25 (CH), 126.20 (CH), 127.27 (CH), | VNK-146 >95% purity | Calcd. 320.2014 Observed 320.2004 |

TABLE 2-continued

Characterization of BCI analogs

| Compound | Yield | Rf | Mp (° C.) | ¹H NMR (CDCl₃, 600 MHz): δ | ¹³C NMR (CDCl₃, 150 MHz): δ | HPLC/ MS | HRMS |
|---|---|---|---|---|---|---|---|
| | | | | Hz, 2H), 7.55 (d, J = 7.2 Hz, 1H), 7.67 (d, J = 7.2 Hz, 2H) | 128.33 (CH), 128.38 (CH), 128.98 (CH), 136.90 (C-q), 143.39 (C-q), 134.61 (C-q), 148.79 (C-q) | | |
| 19 VNK-108 | 47% | | 126-129 (decomp.) | VNK-I-114H: 0.85-1.80 (m, 15H), 2.08 (td, J = 7.2 Hz, J = 2.4 Hz, 2H), 2.25-2.32 (m, 1H), 2.69 (d, J = 12.6 Hz, 1H), 2.88 (dd, J = 13.2 Hz, J = 4.8 Hz, 1H), 3.10 (td, J = 7.2 Hz, J = 4.8 Hz, 1H), 3.52-3.59 (m, 1H), 4.26 (dd, J = 6.0 Hz, J = 4.8 Hz, 1H), 4.47 (dd, J = 7.8 Hz, J = 5.4 Hz, 1H), 5.15 (br.s, 1H), 5.37 (s, 1H), 5.55 (d, J = 6.0 Hz, 1H), 5.96 (d, J = 17.4 Hz, 1H), 7.39-7.49 (m, 4H), 7.65-7.67 (m, 2H), 7.75 (br.s, 1H), 7.86 (d, J = 7.2 Hz, 2H), 7.89 (d, J = 7.8 Hz, 1H) | VNK-I-114CC: 25.61, 28.00, 29.71, 31.51, 31.61, 32.56, 33.29, 36.02, 40.54, 47.72, 51.74, 55.41, 55.52, 60.12, 61.73, 124.09, 126.13, 128.78, 129.94, 131.36, 134.65, 134.80, 136.25, 137.45, 137.98, 138.03, 152.80 163.48, 172.20, 193.62 | VNK-108G >95% purity | Calcd. 559.2743, Observed 559.2750 |
| 19b | 91% | | >300 | VNK-MT-2_HH: (D₂O, 600 MHz): δ 1.20-1.65 (m, 7H), 1.75-1.80 (m, 2H), 1.85-1.90 (m, 1H), 1.94-1.99 (m, 1H), 2.02-2.06 (m, 1H), 2.07 (td, J = 7.2 Hz, J = 3.0 Hz, 2H), 2.09-2.13 (m, 1H), 2.54 (br.s, 4H), 2.66 (dd, J = 13.2 Hz, J = 4.2 Hz, 1H), 2.88 (dtd, J = 12.6 Hz, J = 4.8 Hz, J = 1.8 Hz, 1H), 3.08-3.14 (m, 1H), 3.19-3.26 (m, 1H), 3.61-3.65 (m, 3H), 4.32 (ddd, J = 13.8 Hz, J = 7.8 Hz, J = 4.2 Hz, 1H), 4.49 (ddd, J = 7.8 Hz, J = 5.4 Hz, J = 2.4 Hz, 1H) | VNK-I-105DC: (DMSO-d6, 150 MHz): δ 26.44, 26.62, 29.30, 29.42, 32.41, 35.37, 35.65, 36.50, 41.29, 50.81, 50.94, 56.70, 60.43, 62.29, 163.95, 174.48 | | Calcd. 341.2011, Observed 341.2011 |
| 20 VNK-I-211B | 32% | 0.20 Hex/ EA 3:1 | Orange crystals 112-113 | 1.361 (d, 1H, J = 12.00), 1.643 (dd, 1H, J = 14.40), 1.747 (d, 1H, J = 12.60), 2.444 (m, 1H), 3.901 (s, 3H), 5.342 (s, 1H), 6.993 (d, 2H, J = 9.00), 7.482 (td, 1H), 7.657 (d, 2H), 7.719 (ds, 1H), 7.918 (d, 1H, J = 7.80), 7.952 (d, 2H, J = 9.00) | 24.89 (CH₂), 25.89 (CH₂), 33.81 (CH₂), 35.01 (CH₂), 52.46 (CH), 55.41 (CH), 114.15 (CH), 124.06 (CH), 126.02 (CH), 127.44 (CR₃), 128.53 (CH), 133.82 (CH), 134.28 (CH), 135.97 (CH), 137.69 (CR₃), 152.73 (CR₃), 160.98 (CR₃), 193.72 (CO) | VNK-211 >95% purity | Calcd. [M + H]⁺ 348.1964, Observed 348.1907 |
| 21 VNK-I-212 | 48% | 0.20 Hex/ EA 9:1 | Yellow oil | 0.88-1.10 (m, 8H), 1.27 (s, 1H), 1.31-1.50 (m, 2H), 1.51-1.54 (m, 2H), 1.60-1.63 (m, 3H), 1.69-1.71 (m, 2H), 2.43 (s, 4H), 5.38 (s, 1H), 7.29 (s, 1H), 7.5 (dt, J = 1.2 Hz, 1H), 7.65-7.69 (m, 2H) 7.71-7.74 (m, 1H), 7.842 (d, J = 8.4 Hz, 2H), 7.92 (d, J = 7.8 Hz, 1H) | 10.97, 14.07, 21.59, 23.00, 23.73, 24.86, 24.99, 25.86, 28.93, 30.35, 33.85, 34.94, 38.72, 52.50, 55.33, 68.15, 76.81, 77.02, 77.23, 124.09, 126.16, 128.57, 128.81, 128.84, 129.47, 130.90, 131.42, 131.66, 131.96, 132.44, 134.45, 136.04, 137.50, 137.57, 140.25, 140.45, 152.86, 167.78, 193.77 | VNK-212 >95% purity | Calcd. [M + H]⁺ 332.2014, Observed 332.0384 |
| 22 VNK-I-215 | 66% | 0.16 Hex/ EA 9:1 | Yellow crystals 131-133 | 0.94 (m, 2H), 1.04 (m, 3H), 1.24 (d, J = 9 Hz, 1H), 1.49 (m, 2H), 1.54 (m, 2H), 1.60 (m, 1H), 2.32 (m, 1H), 5.35 (s, 1H), 7.42 (t, J = 7.2 Hz, 1H), 7.47 (t, J = 7.2 Hz, 2H), 7.62 (dd, J = 8.2 Hz, J = 1.8 Hz, 1H), 7.77 (d, J = 7.8 Hz, 2H), 7.83 (d, J = 1.2 Hz, 1H), 7.87 (d, J = 7.2 Hz, 1H) | 24.87, 25.01, 25.90, 34.04, 34.89, 52.73, 55.34, 125..54, 128.87, 129.59, 129.89, 130.09, 131.52, 132.35, 134.72, 136.32, 136.85, 137.83, 154.88, 192.66 | VNK-215 >95% purity | Calcd. [M + H]⁺ 396.0963, Observed 396.1009 |
| 23 VNK-I-216 | 88% | 0.07 Hex/ EA 5:1 | yellow oil | 0.88-1.63 (m, 11H), 2.33 (m, 1H), 3.93 (s, 3H), 5.34 (s, 1H), 7.01 (dd, J = 8.4 Hz, J = 1.8 Hz, 1H), 7.12 (d, J = 1.8 Hz), 7.39 (t, J = 7.2 Hz, 1H), 7.45 (t, J = 7.8 Hz, 2H), 7.70 (s, 1H), 8.85 (t, J = 7.8 Hz, 3H) | 11.11, 14.21, 23.14, 23.87, 24.97, 25.11, 25.93, 20.07, 30.49, 34.33, 34.95, 38.86, 52.62, 55.65, 55.93, 68.29, 109.86, 116.32, 126.05, 128.16, 128.80, 128.95, 129.58, 131.04, 131.07, 131.17, 134.74, 135.17, 139.09, 156.08, 165.33, 192.19 | VNK-216 >95% purity | Calcd. [M + H]⁺ 348.1964, Observed 348.1874 |
| 24 VNK-I-217 | 88% | | Yellow oil | Mixture of isomers CSA-1-12B-pure, CSA-1-13B-isomerized | ND | Mixture of isomers 20:72 by HPLC VNK-217 >95% purity | Calcd. [M + H]⁺ 292.1701 Observed 292.1666 |
| 25 | 86% | 0.27 Hex/ EA 1:1 | yellow solid 161-163 | 0.92-1.12 (m, 5H), 1.30-1.37 (m, 1H), 1.46-1.565 (m, 2H), 1.57-1.68 (m, 3H), 2.3702.45 (m, 1H), 3.88 (s, 3H), 3.94 (s, 3H), 5.28 (s, 1H), 6.98 (d, J = 8.4 Hz, 2H), 7.01 (d, J = 8.4 Hz, 1H), 7.11 (s, 1H), 7.65 (s, 1H), 7.86 (d, J = 8.4 | 24.92 (CH₂), 24.99 (CH₂), 25.84 (CH₂), 34.14 (CH₂), 34.99 (CH₂), 52.39 (CH or CH₃), 55.39 (CH or CH₃), 55.50 (CH or CH₃), 55.75 | | (M + H⁺): Calcd. [M + H]⁺ 378.2069, Observed |

TABLE 2-continued

Characterization of BCI analogs

| Compound | Yield | Rf | Mp (° C.) | $^1$H NMR (CDCl$_3$, 600 MHz): δ | $^{13}$C NMR (CDCl$_3$, 150 MHz): δ | HPLC/ MS | HRMS |
|---|---|---|---|---|---|---|---|
| | | | | Hz, 1H), 7.88 (d, J = 8.4 Hz, 2H) | (CH or CH$_3$), 109.76 (CH), 114.13 (CH), 115.83 (CH), 125.80 (CH), 127.59, 131.13, 133.38 (CH), 134.64 (CH), 136.51, 155.62, 160.72, 164.93, 192.17 | | 378.2180 |
| 26 | 79% | 0.22 Hex/ EA 1:1 | yellow solid 156-158 | 2.50 (br.s, 2H), 2.77 (br.s, 2H), 3.62 (br.s, 4H), 3.87 (s, 3H), 3.94 (s, 3H), 5.00 (s, 1H), 6.98 (d, J = 8.4 Hz, 2H), 7.02 (dd, J = 8.4 Hz, J = 2.4 Hz, 1H), 7.07 (d, J = 1.8 Hz, 1H), 7.65 (d, J = 0.6 Hz, 1H), 7.88 (d, J = 8.4 Hz, 1H), 7.95 (d, J = 8.4 Hz, 2H) | 48.95 (CH$_2$), 55.38 (CH$_3$), 55.76 (CH$_3$), 64.47 (CH), 67.37 (CH$_2$), 110.97 (CH), 113.92 (CH), 115.71 (CH), 125.96 (CH), 127.66, 131.96, 134.31 (CH), 134.55, 135.87 (CH), 151.15, 160.90, 164.53, 191.78 | Purity >95% by LC/MS | Calcd. [M + H]$^+$ 366.1705, Observed 366.1795 |
| 27 | 86% | 0.40 Hex/ EA 1:1 | yellow solid 175-177 | 2.49 (br.s, 2H), 2.75 (br.s, 2H), 3.62 (t, J = 4.2 Hz, 4H), 5.08 (d, J = 1.2 Hz, 1H), 7.45 (d, J = 8.4 Hz, 2H), 7.52-7.56 (m, 1H), 7.65-7.68 (m, 2H), 7.71 (d, J = 1.8 Hz, 1H), 7.95 (d, J = 8.4 Hz, 1H), 7.97 (d, J = 8.4 Hz, 2H) | 49.03, 64.38, 67.26, 124.41, 126.88, 128.76, 129.20, 133.27, 133.59, 134.42, 135.81, 136.01, 137.03, 138.32, 148.50, 192.90 | Purity >95% by LC/MS | Calcd. [M + H]$^+$ 340.1104, Observed 340.1132 |
| 28 | 77% | | yellow solid 176-178 | 0.95-1.17 (m, 5H), 1.35 (d, J = 12.6 Hz, 1H), 1.47 (s, 1H), 1.51-1.58 (m, 2H), 1.68 (t, J = 13.8 Hz, 2H), 2.41 (tt, J = 10.2 Hz, J = 3.6 Hz, 1H), 5.27 (s, 1H), 7.45 (d, J = 8.4 Hz, 2H), 7.64 (dd, J = 8.4 Hz, J = 1.2 Hz, 1H), 7.69 (d, J = 1.8 Hz, 1H), 7.78 (d, J = 8.4 Hz, 1H), 7.80 (br.s, 1H), 7.93 (d, J = 8.4 Hz, 2H) | 24.75 (CH$_2$), 24.81 (CH$_2$), 25.78 (CH$_2$), 33.67 (CH$_2$), 34.88 (CH$_2$), 52.55 (CH), 54.99 (CH), 125.52 (CH), 128.95 (CH), 129.28 (CH), 129.86 (C), 132.31 (CH), 133.02 (C), 133.10 (CH), 135.49 (CH), 136.08 (C), 137.99 (CH), 154.43 (C), 192.29 (C) | Purity >95% by LC/MS | |
| 29 | 72% | | yellow solid 222-224 | 2.49 (br.s, 2H), 2.73 (br.s, 2H), 3.62 (br.s, 4H), 5.04 (s, 1H), 7.45 (d, J = 8.4 Hz, 2H), 7.67 (d, J = 8.4 Hz, 1H), 7.71 (s, 1H), 7.80 (d, J = 8.4 Hz, 1H), 7.83 (s, 1H), 7.93 (d, J = 8.4 Hz, 2H) | 48.99 (CH$_2$), 64.16 (CH), 67.19 (CH$_2$), 125.67 (CH), 128.86 (CH), 129.68 (C), 129.96 (CH), 132.76 (CH), 132.98 (C), 133.61 (CH), 136.26 (C), 136.34 (C), 136.58 (CH), 137.14 (C), 150.06 (C), 191.65 (C) | Purity >95% by LC/MS | |
| 30 | ??? | 0.1 Hex/ EA 9:1 | 183-184 | 2.51 (br s, 2H), 2.74 (br.s, 2H), 3.62 (t, J = 4.2 Hz, 4H), 5.09 (s, 1H), 7.44-7.50 (m, 3H), 7.66 (d, J = 1.8 Hz, 1H), 7.79 (d, J = .6 Hz, 1H), 7.81 (d, J = 8.4 Hz, 1H), 7.84 (d, J = .6 Hz, 1H), 7.98 (d, J = 6.6 Hz, 2H) | 30.96, 64.22, 67.23, 125.61, 128.57, 129.51, 129.92, 130.22, 132.38, 132.64, 134.57, 135.88, 137.22, 138.09, 150.28, ~192 | | |
| 31 | 74% | | | | | | |
| 32 | 72% | | | | | | |

TABLE 3

Characterization of bromobenzylidene indanones

| Compound | Yield | Rf | Mp, ° C. | $^1$H NMR (CDCl$_3$, 600 MHz): δ | $^{13}$C NMR (CDCl$_3$, 150 MHz): δ | HRMS |
|---|---|---|---|---|---|---|
| 14a | 57% | | 168-170° C. | 6.38 (s, 1H), 7.55 (d, J = 1.2 Hz, 2H), 7.57 (t, J = 0.6 Hz, 1H), 7.74 (s, 1H), 7.74-7.77 (m, 4H), 7.93 (d, J = 7.8 Hz, 1H) | 42.52, 124.26, 127.07, 129.35, 130.11, 131.93, 133.73, 135.39, 135.67, 135.76, 136.27, 136.94, 150.44, 190.63 | Calcd. (M − Br) 253.0420 Observed 253.0339 |
| 15a VNK-I-132 | 83% | 0.60 DCM | Colorless crystals 197-199 (decomp.) | $^1$H NMR (DMSO-d6, 600 MHz): δ 7.16 (s, 1H), 7.65 (t, J = 7.2 Hz, 1H), 7.74 (s, 1H), 7.83-7.90 (m, 3H), 8.03 (d, J = 8.4 Hz, 2H), 8.11 (d, J = 8.4 Hz, 2H) | $^{13}$C NMR (DMSO-d6, 150 MHz): δ 43.04, 112.44, 118.49, 123.72, 127.54, 130.44, 132.49, 132.70, 133.83, 135.37, 136.47, 137.54, 138.55, 150.89, 189.90 | Calcd. 324.0024, Observed 324.0060 |
| 20a VNK-I-211A | 28% | | colorless crystals | 2.79 (s, 4.6H), 3.92 (s, 3H), 6.397 (s, 1H), 7.06 (d, J = 8.4 Hz, 2H), 7.78 (d, J = 7.8 Hz, 1H), 7.84 (d, J = 9.0 Hz, 2H), 7.91 (d, J = 7.8 Hz, 1H); 7.53 (t, 1H), 7.72 (t, 2H) | ND | Calcd. [M − Br]$^+$ 249.0916 Observed 249.0723 |
| 22a VNK-I-215a | 10% | 0.20 Hex/ EA 15:1 | colorless crystals 188-190 | 6.33 (s, 1H), 7.53 (m, 3H), 7.67 (dd, J = 7.8 Hz, J = 1.2 Hz, 1H), 7.76 (t, J = 5.4 Hz, 2H), 7.82 (d, J = 7.2 Hz, 2H), 7.92 (s, 1H) | 41.72, 125.59, 129.22, 130.44, 130.54, 131.09, 132.85, 133.39, 133.73, 134.88, 135.26, 137.83, 152.23, 189.87 | Calcd. [M + H]$^+$ 376.9171 Observed 376.9174 |

TABLE 3-continued

Characterization of bromobenzylidene indanones

| Compound | Yield | Rf | Mp, °C. | $^1$H NMR (CDCl$_3$, 600 MHz): δ | $^{13}$C NMR (CDCl$_3$, 150 MHz): δ | HRMS |
|---|---|---|---|---|---|---|
| 23a VNK-I-216a | 89% | 0.40 Hex/ EA 3:1 | Yellow crystals 146-148 | 3.95 (s, 3H), 6.34 (s, 1H), 6.05 (dd, J = 8.4 Hz, J = 1.8 Hz, 1H), 7.16 (d, J = 2.4 Hz, 1H), 7.47 (t, J = 7.2 Hz, 1H), 7.52 (t, J = 7.2 Hz, 2H), 7.68 (s, 1H), 7.81 (d, J = 7.8 Hz, 2H), 7.84 (d, J = 8.4 Hz, 1H) | 43.08, 56.08, 110.25, 118.17, 126.14, 129.08, 129.88, 130.54, 132.54, 133.78, 135.85, 136.01, 153.52, 165.89, 189.41 | Calcd. [M + H]$^+$ 329.0177 Observed 329.0183 |
| 25a | 91% | | Yellow solid 171-173 | 3.91 (s, 3H), 3.96 (s, 3H), 6.32 (s, 1H), 7.03-7.08 (m, 3H), 7.18 (d, J = 1.8 Hz, 1H), 7.65 (s, 1H), 7.79 (d, J = 8.4 Hz, 2H), 7.84 (d, J = 8.4 Hz, 1H) | 43.89, 55.48, 55.91, 110.16, 114.52, 117.81, 125.82, 126.32, 129.96, 133.24, 134.69, 135.62, 153.19, 161.52, 165.52, 189.38 | |
| 28a | 78% | | White solid 199-201 | 6.29 (s, 1H), 7.52 (d, J = 8.4 Hz, 2H), 7.68 (d, J = 8.4 Hz, 1H), 7.71 (s, 1H), 7.75 (d, J = 8.4 Hz, 2H), 7.78 (d, J = 8.4 hz, 1H), 7.93 (s, 1H) | 41.23, 125.47, 129.42, 130.33, 130.58, 131.67, 133.70, 133.77, 135.04, 135.11, 136.13, 137.23, 151.90, 189.46 | |
| 31a | 74% | | White solid 216-219 | 6.35 (s, 1H), 7.57 (t, J = 7.2 Hz, 1H), 7.61 (d, J = 8.4 Hz, 1H), 7.64 (d, J = 0.6 Hz, 1H), 7.66 (dd, J = 8.4 Hz, J = 2.4 Hz, 1H), 7.76 (td, J = 7.8 Hz, J = 0.6 Hz, 1H), 7.79 (d, J = 7.8 Hz, 1H), 7.91-7.95 (m, 2H) | 41.90, 124.33, 127.12, 130.22, 130.96, 131.27, 133.38, 133.41, 133.79, 134.86, 135.88, 136.13, 136.91, 150.35, 190.34 | |

TABLE 4

Characterization of benzylidene indanones

| Compound | Yield | Rf | Mp, °C. | $^1$H NMR (CDCl$_3$, 600 MHz): δ | $^{13}$C NMR (CDCl$_3$, 150 MHz): δ | HRMS |
|---|---|---|---|---|---|---|
| 25b | 99% | | slightly yellow solid, mp = 146-148° C. | 3.88 (s, 3H), 3.93 (s, 3H), 3.99 (s, 2H, CH$_2$), 6.95-7.05 (m, 4H), 7.60 (t, J = 1.8 Hz, 1H), 7.64 (d, J = 9.0 Hz, 2H), 7.86 (d, J = 8.4 Hz, 1H) | 32.56, 55.40, 55.68, 109.75, 114.41, 115.08, 126.07, 128.33, 131.67, 132.35, 132.53, 132.94, 152.35, 160.62, 165.03, 192.91 | |
| 28b | 97% | | white solid 251-254 | 4.02 (s, 2H), 7.46 (d, J = 8.4 Hz, 2H), 7.57-7.62 (m, 3H), 7.65 (t, J = 2.4 Hz, 1H), 7.75 (br.s, 1H), 7.79 (d, J = 8.4 Hz, 1H) | 32.04, 125.75, 129.33, 129.48, 129.90, 131.46, 131.83, 133.25, 133.58, 134.39, 135.98, 136.76, 150.95, 192.92 | |

EXAMPLE 15

Structure-Activity Relationship of BCI Analogs

We tested a series of structurally related analogs of BCI in an in vivo assay. As described in Molina et al. (Nature Chemical Biology, 2009), Tg(Dusp6:dsEGFP) embryos were treated at 24 hours post fertilization with increasing doses of compounds. After 6 hours treatment, embryos were imaged by the IXU ImageXpress (Molecular Devices), and images were processed by Definiens Software. The software identified bright head structures and measured fluorescence.

In a dose-dependent manner, BCI expanded GFP expression in transgenic embryos and the EC$_{50}$ was measured as 11.4 μM (FIG. 16). Under similar conditions, BCI-related analogs were tested and EC$_{50}$ values measured. In these studies, MT9 was at least 2.5 fold more potent than BCI, while other analogs were equipotent to BCI (FIG. 17).

We next addressed if BCI and related analogs are detrimental to zebrafish embryo survival after prolong exposure. Embryos soaked in BCI at high doses (>10 μM) for 24 hours resulted in embryo defects, such as tail necrosis and even death (FIG. 17). The percentage of embryos that died after 24 hours treatment was 100% at 20 μM. Treatment with the highly potent MT9 resulted in 100% lethality at lower doses (10 μM) than BCI. In contrast VNK215, which had similar activity to BCI was non-toxic, even as high as 40 μM (FIG. 17 and not shown).

Thus, the cyclohexoamino group of BCI appears important for that compound's potency in inhibiting Dusp6 and the addition of a bromine to the indanone group suppresses toxicity.

EXAMPLE 16

BCI Structure-Activity Relationship Studies

Transgenic zebrafish embryos (24 hpf) were treated with 20 μM solution of BCI analogs in 0.5% aq DMSO and fluorescence photomicrographs were taken after 6 h. The effectiveness of BCI analogs was evaluated by densitometry (ImageJ) of d2EGFP intensity in the dorsal region.

TABLE 5

| Compound | Activity (BCI = 100) |
|---|---|
| 1 | 0 |
| 3 (BCI) | 100 |
| (−)-BCI | 156 |
| (+)-BCI | 82 |
| 4 | 123 |
| 5 | 127 |
| 6 | 7 |
| 7 | 114 |
| 8 | Less than BCI |
| 9 | 114 |
| 10 | 27 |
| 11 | 22 |
| 12 | 0 |

TABLE 5-continued

| Compound | Activity (BCI = 100) |
|---|---|
| 13 | 47 |
| 14 | 52 |
| 15 | 20 |
| 16 | Less than BCI |
| 17 (ICD) | 0 |
| 18 | 26 |
| 19 | No activity, trapped in yolk |

Table 5 shows the in vivo activity of eighteen BCI analogs. First, the structural features required for the activity of BCI were determined. Analog 1, lacking the cyclohexylamine group, and analog 17 (ICD), lacking the benzylidene group, were inactive. Reduction of the carbonyl group to an alcohol in analog 18 resulted in a significant loss of activity. Thus, for BCI, the amino group and benzylidene are important for the activity of BCI, and the carbonyl group is desirable.

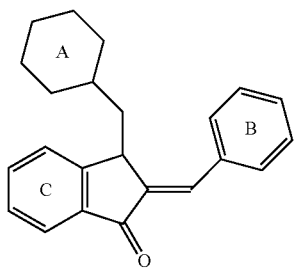

Second, analogs 4-6, comprising different secondary amines were tested. In reference to the structure above, replacement of ring A of BCI with a cyclopentyl or cyloheptyl ring resulted in a significant increase of activity, whereas replacement of the flexible cyclohexylamine ring with a rigid phenyl group (analog 6) dramatically decreased activity. Molecular modeling suggested that the NH at C3 of the indanone forms a hydrogen bond with Trp264 in the binding site of Dusp6. To test this hypothesis, we synthesized compound 7, comprising a piperidine at C3. Unexpectedly, 7 was more active than BCI, despite the lack of a hydrogen bond donor.

Since we established that the group at the C3 of the indanone in the general scaffold can be a secondary or tertiary amine, we studied the effect of additional hydrogen bond donors/acceptors in the 4' position of Ring B of BCI. Introduction of an additional amine in compound 8 resulted in significant loss of activity. Morpholine analog 9 had the same activity as piperidine analog 7. Thiomorpholine analog 10 and the three piperazine analogs 11-13, however, had much less activity.

A study of the structure-activity relationship on the periphery of other rings was then undertaken. Molecular modeling suggested that ring B is oriented out of the binding pocket, and substituents on this ring could affect activity only indirectly. We found that introduction of chloride in the p-position of ring B resulted in a loss of activity for 14 (52% as compared to BCI), whereas a more electron withdrawing cyano group at this position in 15 decreased activity even further (to 20%). Introduction of a cyano group to ring C in 16 also resulted in a decrease in activity. Finally, biotin-linked analog 19 was completely trapped in the yolk and showed no effect on FGF signaling.

We have separated the enantiomers of BCI by supercritical fluid chromatography over commercially available chiral columns (See, Cole, J., et al. Profiling the isomerization of biologically relevant (E)-(Z) isomers by supercritical fluid chromatography (SFC). LCGC *The Application Notebook—Chromatography Online,* 2009, Jun. 1, 1-6 [erratum in September 2009, 51]) and determined that the activity of the levorotatory enantiomer is twice that of the dextrorotatory form. Establishment of the absolute configuration of each enantiomer is in progress.

Having described this invention above, it will be understood to those of ordinary skill in the art that the same can be performed within a wide and equivalent range of conditions, formulations and other parameters without affecting the scope of the invention or any embodiment thereof. Any document incorporated herein by reference is only done so to the extent of its technical disclosure and to the extent it is consistent with the present application and the disclosure provided herein. Deference is to be given to definitions, descriptions, wording, language, data, statements, etc. provided in the present document where any material disclosed in such incorporated references, to include definitions, descriptions, data and statements, conflicts with material provided in the present application.

We claim:

1. A compound having the formula:

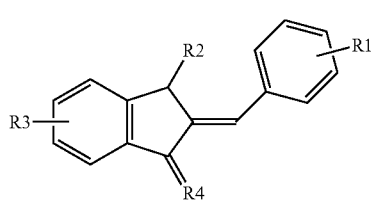

in which R1 represents one or more independently of H, halo, $C_{1-3}$ alkyl, $C_{1-3}$ alkoxyl or —CN; R2 is a secondary or tertiary amine group; R3 is one or more independently of halo, $C_{1-3}$ alkyl, $C_{1-3}$ alkoxyl or —CN; and R4 is =O or OH, or a pharmaceutically acceptable salt thereof.

2. The compound of claim 1 in which R3 is halo.

3. The compound of claim 2 in which R3 is Br.

4. The compound of claim 1 in which R2 is a $C_{4-10}$ cycloalkylamine.

5. The compound of claim 1 in which R2 is one of cyclopentylamine and cycloheptylamine.

6. The compound of claim 1 in which R1 is H, R2 is one of cyclopentylamine, cyclohexylamine, and cycloheptylamine, and R3 is Br.

7. The compound of claim 6 in which R2 is cyclohexylamine.

8. The compound of claim 1 consisting essentially of a (−) enantiomer of the compound.

9. The compound of claim 1 having the formula:

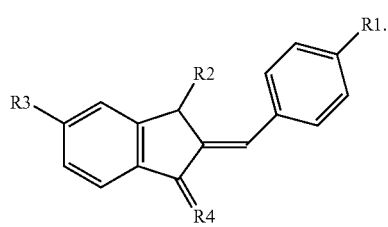

10. The compound of claim 1 in which R4 is =O.

11. The compound of claim 10 in which R2 is one of 4-t-Boc-cyclohexylamine, thiamorpholine, piperazine, methyl piperazine, acetyl piperazine, cyclopentylamine, cycloheptylamine and di-$C_{1-4}$-alkylamine.

12. The compound of claim 1 in which R4 is —OH.

13. The compound of claim 1, wherein R1 is 3,4-di-halo.

14. The compound of claim 1, wherein R1 is 3,4-dichloro.

15. The compound of claim 1, having the structure:

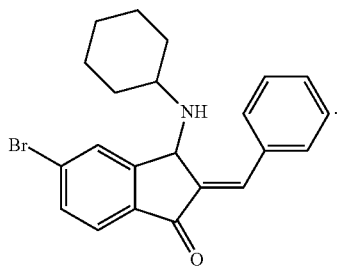 [SMILES: O=C1/C(=C/c2ccccc2)C(NC2CCCCC2)c2cc(Br)ccc21]

16. A compound consisting of a (−) enantiomer of a compound having the formula:

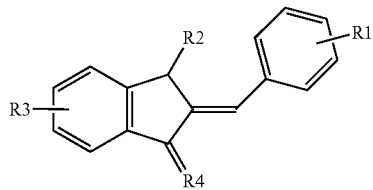

in which R1 represents one or more independently of H, halo, $C_{1-3}$ alkyl, $C_{1-3}$ alkoxyl or —CN; R2 is a primary or secondary amine; R3 is one or more independently of H, halo, $C_{1-3}$ alkyl, $C_{1-3}$ alkoxyl or —CN; and R4 is =O or —OH.

17. A composition comprising one or more compounds of claim 1 and a pharmaceutically acceptable excipient.

18. A method of stimulating cell growth in a population of cells, comprising contacting the cell population with compound having the formula:

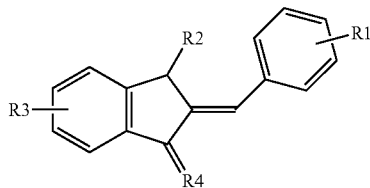

in which R1 represents one or more independently of H, halo, $C_{1-3}$ alkyl, $C_{1-3}$ alkoxyl or —CN; R2 is a secondary or tertiary amine group; R3 is one or more independently of halo, $C_{1-3}$ alkyl, $C_{1-3}$ alkoxyl or —CN; and R4 is =O or —OH, or a pharmaceutically acceptable salt thereof, in an amount effective to increase FGF secretion by the cell.

19. The method of claim 18, comprising applying the compound to a tissue in an organism.

20. The method of claim 19 in which the tissue of the organism is damaged or deficient.

21. The method of claim 18 comprising obtaining cells from a patient and contacting the cells in vitro with the compound to expand the population of cells.

22. The compound of claim 1 in which R2 is one of $C_{4-10}$ cycloalkylamine, 4-t-Boc-cyclohexylamine, thiamorpholine, piperazine, methyl piperazine, acetyl piperazine, phenylamine, piperidine, morpholine, biotin, and di-$C_{1-4}$-alkylamine.

* * * * *

UNITED STATES PATENT AND TRADEMARK OFFICE
CERTIFICATE OF CORRECTION

| | |
|---|---|
| PATENT NO. | : 9,127,016 B2 |
| APPLICATION NO. | : 13/256584 |
| DATED | : September 8, 2015 |
| INVENTOR(S) | : Billy W. Day et al. |

It is certified that error appears in the above-identified patent and that said Letters Patent is hereby corrected as shown below:

Title Page

Item (56), OTHER PUBLICATIONS, Line 26, delete "Stucture-" and insert -- Structure- --

Claims

Column 45, Line 57, Claim 1, delete "OH," and insert -- —OH, --

Signed and Sealed this
Eighth Day of March, 2016

Michelle K. Lee
*Director of the United States Patent and Trademark Office*

SEQUENCE LISTING

<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: Dusp5 Forward Primer

<400> SEQUENCE: 1
aactcgaggc catgaaggtc tccagcatag attgccg                37

<210> SEQ ID NO 2
<211> LENGTH: 33
<212> TYPE: DNA
<213> ORGANISM: Artificial Sequence
<220> FEATURE:
<223> OTHER INFORMATION: Dusp5 Reverse Primer

```
<400> SEQUENCE: 2
aatctagatt aaggcagcgc agttattgga ctc                              33

<210> SEQ ID NO 3
<211> LENGTH: 37
<212> TYPE: DNA
<213> ORGANISM: Artificial Sequence
<220> FEATURE:
<223> OTHER INFORMATION: Spry4 Forward Primer

<400> SEQUENCE: 3
actcgagcca tggagtcaag ggttcctcac cacattc                          37

<210> SEQ ID NO 4
<211> LENGTH: 34
<212> TYPE: DNA
<213> ORGANISM: Artificial Sequence
<220> FEATURE:
<223> OTHER INFORMATION: Spry4 Reverse Primer

<400> SEQUENCE: 4
aatctagatc atgaggcttg tttttctggc tgac                             34

<210> SEQ ID NO 5
<211> LENGTH: 19
<212> TYPE: DNA
<213> ORGANISM: Artificial Sequence
<220> FEATURE:
<223> OTHER INFORMATION: Dusp6 Primer

<400> SEQUENCE: 5
cgttcagagg ggttgtccg                                              19

<210> SEQ ID NO 6
<211> LENGTH: 20
<212> TYPE: DNA
<213> ORGANISM: Artificial Sequence
<220> FEATURE:
<223> OTHER INFORMATION: Dusp6 Primer

<400> SEQUENCE: 6
cttccctgaa caggagaccc                                             20

<210> SEQ ID NO 7
<211> LENGTH: 20
<212> TYPE: DNA
<213> ORGANISM: Artificial Sequence
<220> FEATURE:
<223> OTHER INFORMATION: Spry4 Primer

<400> SEQUENCE: 7
gcggagcagc ccaagatact                                             20

<210> SEQ ID NO 8
<211> LENGTH: 22
<212> TYPE: DNA
<213> ORGANISM: Artificial Sequence
<220> FEATURE:
<223> OTHER INFORMATION: Spry4 Primer

<400> SEQUENCE: 8
caggcagggc aaaaccaatg ag                                          22

<210> SEQ ID NO 9
<211> LENGTH: 21
```

```
<212> TYPE: DNA
<213> ORGANISM: Artificial Sequence
<220> FEATURE:
<223> OTHER INFORMATION: Sef Primer

<400> SEQUENCE: 9
ccagtcagga cgcgggttca t                                         21

<210> SEQ ID NO 10
<211> LENGTH: 24
<212> TYPE: DNA
<213> ORGANISM: Artificial Sequence
<220> FEATURE:
<223> OTHER INFORMATION: Sef Primer

<400> SEQUENCE: 10
gttaaagtgg cgctgcgagt ggag                                      24

<210> SEQ ID NO 11
<211> LENGTH: 21
<212> TYPE: DNA
<213> ORGANISM: Artificial Sequence
<220> FEATURE:
<223> OTHER INFORMATION: Histone H4 Primer

<400> SEQUENCE: 11
cacgaaaccc gccatccgtc g                                         21

<210> SEQ ID NO 12
<211> LENGTH: 21
<212> TYPE: DNA
<213> ORGANISM: Artificial Sequence
<220> FEATURE:
<223> OTHER INFORMATION: Histone H4 Primer

<400> SEQUENCE: 12
gtacagagtg cgtccctgcc g                                         21
```